(12) United States Patent
Withers et al.

(10) Patent No.: US 10,583,167 B2
(45) Date of Patent: Mar. 10, 2020

(54) MAMMALIAN GLUCOSIDASE INHIBITORS, METHODS FOR THEIR USE AND PHARMACEUTICAL COMPOSITIONS THEREOF

(71) Applicant: THE UNIVERSITY OF BRITISH COLUMBIA, Vancouver (CA)

(72) Inventors: Stephen G. Withers, Vancouver (CA); Andrew Tarling, Vancouver (CA); Raymond J. Andersen, Vancouver (CA); Gary D. Brayer, Richmond (CA); Robert Keyzers, Wellington (NZ); Christina Rose Tysoe, Vancouver (CA); Leslie Karen Williams, Surrey (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 15/740,494

(22) PCT Filed: Jun. 29, 2016

(86) PCT No.: PCT/CA2016/000183
§ 371 (c)(1),
(2) Date: Dec. 28, 2017

(87) PCT Pub. No.: WO2017/000060
PCT Pub. Date: Jan. 5, 2017

(65) Prior Publication Data
US 2018/0193413 A1 Jul. 12, 2018

Related U.S. Application Data

(60) Provisional application No. 62/185,931, filed on Jun. 29, 2015, provisional application No. 62/332,600, filed on May 6, 2016.

(51) Int. Cl.
| | | |
|---|---|---|
| *A61K 38/17* | (2006.01) | |
| *A61K 9/00* | (2006.01) | |
| *A61P 1/16* | (2006.01) | |
| *A61P 3/00* | (2006.01) | |
| *A61P 31/12* | (2006.01) | |

(52) U.S. Cl.
CPC .......... *A61K 38/17* (2013.01); *A61K 9/0053* (2013.01); *A61P 1/16* (2018.01); *A61P 3/00* (2018.01); *A61P 31/12* (2018.01)

(58) Field of Classification Search
CPC ...................................... A61K 38/17
See application file for complete search history.

(56) References Cited

U.S. PATENT DOCUMENTS 7,317,077 B2 * 1/2008 Averback ........... C07K 14/4711
530/300
2004/0214272 A1 * 10/2004 La Rosa ............... C07H 21/04
435/69.1

OTHER PUBLICATIONS

Numao, S. et al., "In Situ Extension as an Approach for Identifying Novel α-Amylase Inhibitors." The Journal of Biological Chemistry, Nov. 2004, 279(46): 48282-48291.
Playford, R. J. et al., "Use of the alpha-glucosidase inhibitor acarbose in patients with 'Middleton syndrome': Normal gastric anatomy but with accelerated gastric emptying causing postprandial reactive hypoglycemia and diarrhea." Can. J. Gastroenterol., Jul. 2013, 27(7): 403-404.
Tysoe, C. et al., "Potent human α-Amylase Inhibition by the β-Defensin-like Protein Helianthamide." ASC Central Science, 2016, 2(3): 154-161.

* cited by examiner

*Primary Examiner* — Amber D Steele
(74) *Attorney, Agent, or Firm* — Saliwanchik, Lloyd & Eisenschenk

(57) ABSTRACT

Provided are methods, uses and pharmaceutical compositions for inhibition of mammalian alpha-amylase in a subject, with a Helianthamide peptide or a derivative thereof in a biologically effective amount. The subject in need of alpha-amylase inhibition, may have or be at risk of developing one or more of the following: Middleton syndrome; a motility disorder of the gastrointestinal tract; postprandial reactive hypoglycemia; postprandial syndrome; irritable bowel syndrome; diabetes mellitus type 1; diabetes mellitus type 2; pre-diabetes; obesity, dumping syndrome; infant dumping syndrome; polycystic ovary syndrome; steatohepatitis; and viral infection.

35 Claims, 6 Drawing Sheets
Specification includes a Sequence Listing.

A.

B.

SEQUENCE LISTING

<160> NUMBER OF SEQ ID NOS: 49

<210> SEQ ID NO 1
<211> LENGTH: 44
<212> TYPE: PRT
<213> ORGANISM: Stichodactyla helianthus

<400> SEQUENCE: 1

Glu Ser Gly Asn Ser Cys Tyr Ile Tyr His Gly Val Ser Gly Ile Cys
1               5                   10                  15

Lys Ala Ser Cys Ala Glu Asp Glu Lys Ala Met Ala Gly Met Gly Val
            20                  25                  30

Cys Glu Gly His Leu Cys Cys Tyr Lys Thr Pro Trp
        35                  40

<210> SEQ ID NO 2
<211> LENGTH: 45
<212> TYPE: PRT
<213> ORGANISM: Stichodactyla helianthus -continued

<400> SEQUENCE: 2

Ser Glu Ser Gly Asn Ser Cys Tyr Ile Tyr His Gly Val Ser Gly Ile
1               5                   10                  15

Cys Lys Ala Ser Cys Ala Glu Asp Glu Lys Ala Met Ala Gly Met Gly
                20                  25                  30

Val Cys Glu Gly His Leu Cys Cys Tyr Lys Thr Pro Trp
            35                  40                  45

<210> SEQ ID NO 3
<211> LENGTH: 45
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (1)..(1)
<223> OTHER INFORMATION: Ser (S) or Thr (T) or absent
<220> FEATURE:
<221> NAME/KEY: MISC_FEATURE
<222> LOCATION: (2)..(2)
<223> OTHER INFORMATION: Asp(D) or Glu (E) or absent
<220> FEATURE:
<221> NAME/KEY: MISC_FEATURE
<222> LOCATION: (3)..(3)
<223> OTHER INFORMATION: Ser (S) or Thr (T) or absent
<220> FEATURE:
<221> NAME/KEY: MISC_FEATURE
<222> LOCATION: (4)..(4)
<223> OTHER INFORMATION: Gly (G) or Ala (A) or absent
<220> FEATURE:
<221> NAME/KEY: MISC_FEATURE
<222> LOCATION: (5)..(5)
<223> OTHER INFORMATION: Asn (N) or Gln (Q) or absent
<220> FEATURE:
<221> NAME/KEY: MISC_FEATURE
<222> LOCATION: (6)..(6)
<223> OTHER INFORMATION: Ser (S) or Thr (T) or absent
<220> FEATURE:
<221> NAME/KEY: MISC_FEATURE
<222> LOCATION: (12)..(12)
<223> OTHER INFORMATION: Gly (G) or Ala (A) or absent
<220> FEATURE:
<221> NAME/KEY: MISC_FEATURE
<222> LOCATION: (13)..(13)
<223> OTHER INFORMATION: Val (V), Ala (A), Ile (I) or Leu (L) or absent
<220> FEATURE:
<221> NAME/KEY: MISC_FEATURE
<222> LOCATION: (14)..(14)
<223> OTHER INFORMATION: Ser (S) or Thr (T) or absent
<220> FEATURE:
<221> NAME/KEY: MISC_FEATURE
<222> LOCATION: (15)..(15)
<223> OTHER INFORMATION: Gly (G) or Ala (A) or absent
<220> FEATURE:
<221> NAME/KEY: MISC_FEATURE
<222> LOCATION: (16)..(16)
<223> OTHER INFORMATION: Val (V), Ala (A), Ile (I) or Leu (L) or absent
<220> FEATURE:
<221> NAME/KEY: MISC_FEATURE
<222> LOCATION: (17)..(17)
<223> OTHER INFORMATION: Cys (C) or absent
<220> FEATURE:
<221> NAME/KEY: MISC_FEATURE
<222> LOCATION: (18)..(18)
<223> OTHER INFORMATION: Lys (K), Arg (R) or His (H) or absent
<220> FEATURE:
<221> NAME/KEY: MISC_FEATURE
<222> LOCATION: (19)..(19)
<223> OTHER INFORMATION: Val (V), Ala (A), Ile (I) or Leu (L) or absent
<220> FEATURE:
<221> NAME/KEY: MISC_FEATURE
<222> LOCATION: (20)..(20)
<223> OTHER INFORMATION: Ser (S) or Thr (T) or absent
<220> FEATURE:

```
<221> NAME/KEY: MISC_FEATURE
<222> LOCATION: (21)..(21)
<223> OTHER INFORMATION: Cys (C) or absent
<220> FEATURE:
<221> NAME/KEY: MISC_FEATURE
<222> LOCATION: (22)..(22)
<223> OTHER INFORMATION: Val (V), Ala (A), Ile (I) or Leu (L) or absent
<220> FEATURE:
<221> NAME/KEY: MISC_FEATURE
<222> LOCATION: (23)..(23)
<223> OTHER INFORMATION: Asp(D) or Glu (E) or absent
<220> FEATURE:
<221> NAME/KEY: MISC_FEATURE
<222> LOCATION: (24)..(24)
<223> OTHER INFORMATION: Asp(D) or Glu (E) or absent
<220> FEATURE:
<221> NAME/KEY: MISC_FEATURE
<222> LOCATION: (25)..(25)
<223> OTHER INFORMATION: Asp(D) or Glu (E) or absent
<220> FEATURE:
<221> NAME/KEY: MISC_FEATURE
<222> LOCATION: (26)..(26)
<223> OTHER INFORMATION: Lys (K), Arg (R) or His (H) or absent
<220> FEATURE:
<221> NAME/KEY: MISC_FEATURE
<222> LOCATION: (27)..(27)
<223> OTHER INFORMATION: Val (V), Ala (A), Ile (I) or Leu (L) or absent
<220> FEATURE:
<221> NAME/KEY: MISC_FEATURE
<222> LOCATION: (28)..(28)
<223> OTHER INFORMATION: Met (M) or Leu (L) or absent
<220> FEATURE:
<221> NAME/KEY: MISC_FEATURE
<222> LOCATION: (29)..(29)
<223> OTHER INFORMATION: Val (V), Ala (A), Ile (I) or Leu (L) or absent
<220> FEATURE:
<221> NAME/KEY: MISC_FEATURE
<222> LOCATION: (30)..(30)
<223> OTHER INFORMATION: Gly (G) or Ala (A) or absent
<220> FEATURE:
<221> NAME/KEY: MISC_FEATURE
<222> LOCATION: (31)..(31)
<223> OTHER INFORMATION: Met (M) or Leu (L) or absent
<220> FEATURE:
<221> NAME/KEY: MISC_FEATURE
<222> LOCATION: (32)..(32)
<223> OTHER INFORMATION: Gly (G) or Ala (A) or absent
<220> FEATURE:
<221> NAME/KEY: MISC_FEATURE
<222> LOCATION: (33)..(33)
<223> OTHER INFORMATION: Val (V), Ala (A), Ile (I) or Leu (L) or absent
<220> FEATURE:
<221> NAME/KEY: MISC_FEATURE
<222> LOCATION: (34)..(34)
<223> OTHER INFORMATION: Cys (C) or absent
<220> FEATURE:
<221> NAME/KEY: MISC_FEATURE
<222> LOCATION: (35)..(35)
<223> OTHER INFORMATION: Asp(D) or Glu (E) or absent
<220> FEATURE:
<221> NAME/KEY: MISC_FEATURE
<222> LOCATION: (36)..(36)
<223> OTHER INFORMATION: Gly (G) or Ala (A) or absent
<220> FEATURE:
<221> NAME/KEY: MISC_FEATURE
<222> LOCATION: (37)..(37)
<223> OTHER INFORMATION: Lys (K), Arg (R) or His (H) or absent
<220> FEATURE:
<221> NAME/KEY: MISC_FEATURE
<222> LOCATION: (38)..(38)
<223> OTHER INFORMATION: Val (V), Ala (A), Ile (I) or Leu (L) or absent
<220> FEATURE:
<221> NAME/KEY: MISC_FEATURE
<222> LOCATION: (39)..(39)
<223> OTHER INFORMATION: Cys (C) or absent
<220> FEATURE:
<221> NAME/KEY: MISC_FEATURE
<222> LOCATION: (40)..(40)
<223> OTHER INFORMATION: Ser (S) or Thr (T) or absent
```

```
<220> FEATURE:
<221> NAME/KEY: MISC_FEATURE
<222> LOCATION: (41)..(41)
<223> OTHER INFORMATION: Tyr (Y) or Phe (F) or absent
<220> FEATURE:
<221> NAME/KEY: MISC_FEATURE
<222> LOCATION: (42)..(42)
<223> OTHER INFORMATION: Lys (K), Arg (R) or His (H) or absent
<220> FEATURE:
<221> NAME/KEY: MISC_FEATURE
<222> LOCATION: (43)..(43)
<223> OTHER INFORMATION: Ser (S) or Thr (T) or absent
<220> FEATURE:
<221> NAME/KEY: MISC_FEATURE
<222> LOCATION: (44)..(44)
<223> OTHER INFORMATION: Pro (P) or absent
<220> FEATURE:
<221> NAME/KEY: MISC_FEATURE
<222> LOCATION: (45)..(45)
<223> OTHER INFORMATION: Trp (W) or Tyr (Y) or absent

<400> SEQUENCE: 3

Xaa Xaa Xaa Xaa Xaa Xaa Cys Tyr Ile Tyr His Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

<210> SEQ ID NO 4
<211> LENGTH: 9
<212> TYPE: PRT
<213> ORGANISM: Stichodactyla helianthus

<400> SEQUENCE: 4

Tyr Ile Tyr His Gly Val Ser Gly Ile
1               5

<210> SEQ ID NO 5
<211> LENGTH: 6
<212> TYPE: PRT
<213> ORGANISM: Stichodactyla helianthus

<400> SEQUENCE: 5

Tyr Ile Tyr His Gly Val
1               5

<210> SEQ ID NO 6
<211> LENGTH: 4
<212> TYPE: PRT
<213> ORGANISM: Stichodactyla helianthus

<400> SEQUENCE: 6

Tyr Ile Tyr His
1

<210> SEQ ID NO 7
<211> LENGTH: 10
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (6)..(6)
<223> OTHER INFORMATION: Gly (G) or Ala (A)
<220> FEATURE:
<221> NAME/KEY: MISC_FEATURE
<222> LOCATION: (7)..(7)
```

```
<223> OTHER INFORMATION: Val (V), Ala (A), Ile (I) or Leu (L)
<220> FEATURE:
<221> NAME/KEY: MISC_FEATURE
<222> LOCATION: (8)..(8)
<223> OTHER INFORMATION: Ser (S) or Thr (T)
<220> FEATURE:
<221> NAME/KEY: MISC_FEATURE
<222> LOCATION: (9)..(9)
<223> OTHER INFORMATION: Gly (G) or Ala (A)
<220> FEATURE:
<221> NAME/KEY: MISC_FEATURE
<222> LOCATION: (10)..(10)
<223> OTHER INFORMATION: Val (V), Ala (A), Ile (I) or Leu (L)

<400> SEQUENCE: 7

Cys Tyr Ile Tyr His Xaa Xaa Xaa Xaa Xaa
1               5                   10

<210> SEQ ID NO 8
<211> LENGTH: 11
<212> TYPE: PRT
<213> ORGANISM: Stichodactyla helianthus

<400> SEQUENCE: 8

Cys Tyr Ile Tyr His Gly Val Ser Gly Ile Cys
1               5                   10

<210> SEQ ID NO 9
<211> LENGTH: 16
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (1)..(1)
<223> OTHER INFORMATION: Ser (S) or Thr (T) or absent
<220> FEATURE:
<221> NAME/KEY: MISC_FEATURE
<222> LOCATION: (2)..(2)
<223> OTHER INFORMATION: Asp(D) or Glu (E)
<220> FEATURE:
<221> NAME/KEY: MISC_FEATURE
<222> LOCATION: (3)..(3)
<223> OTHER INFORMATION: Ser (S) or Thr (T)
<220> FEATURE:
<221> NAME/KEY: MISC_FEATURE
<222> LOCATION: (4)..(4)
<223> OTHER INFORMATION: Gly (G) or Ala (A)
<220> FEATURE:
<221> NAME/KEY: MISC_FEATURE
<222> LOCATION: (5)..(5)
<223> OTHER INFORMATION: Asn (N) or Gln (Q)
<220> FEATURE:
<221> NAME/KEY: MISC_FEATURE
<222> LOCATION: (6)..(6)
<223> OTHER INFORMATION: Ser (S) or Thr (T)
<220> FEATURE:
<221> NAME/KEY: MISC_FEATURE
<222> LOCATION: (12)..(12)
<223> OTHER INFORMATION: Gly (G) or Ala (A)
<220> FEATURE:
<221> NAME/KEY: MISC_FEATURE
<222> LOCATION: (13)..(13)
<223> OTHER INFORMATION: Val (V), Ala (A), Ile (I) or Leu (L)
<220> FEATURE:
<221> NAME/KEY: MISC_FEATURE
<222> LOCATION: (14)..(14)
<223> OTHER INFORMATION: Ser (S) or Thr (T)
<220> FEATURE:
<221> NAME/KEY: MISC_FEATURE
<222> LOCATION: (15)..(15)
<223> OTHER INFORMATION: Gly (G) or Ala (A)
<220> FEATURE:
<221> NAME/KEY: MISC_FEATURE
```

```
<222> LOCATION: (16)..(16)
<223> OTHER INFORMATION: Val (V), Ala (A), Ile (I) or Leu (L)

<400> SEQUENCE: 9

Xaa Xaa Xaa Xaa Xaa Xaa Cys Tyr Ile Tyr His Xaa Xaa Xaa Xaa Xaa
1               5                   10                  15

<210> SEQ ID NO 10
<211> LENGTH: 44
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (1)..(1)
<223> OTHER INFORMATION: Asp(D) or Glu (E)
<220> FEATURE:
<221> NAME/KEY: MISC_FEATURE
<222> LOCATION: (2)..(2)
<223> OTHER INFORMATION: Ser (S) or Thr (T)
<220> FEATURE:
<221> NAME/KEY: MISC_FEATURE
<222> LOCATION: (3)..(3)
<223> OTHER INFORMATION: Gly (G) or Ala (A)
<220> FEATURE:
<221> NAME/KEY: MISC_FEATURE
<222> LOCATION: (4)..(4)
<223> OTHER INFORMATION: Asn (N) or Gln (Q)
<220> FEATURE:
<221> NAME/KEY: MISC_FEATURE
<222> LOCATION: (5)..(5)
<223> OTHER INFORMATION: Ser (S) or Thr (T)
<220> FEATURE:
<221> NAME/KEY: MISC_FEATURE
<222> LOCATION: (11)..(11)
<223> OTHER INFORMATION: Gly (G) or Ala (A)
<220> FEATURE:
<221> NAME/KEY: MISC_FEATURE
<222> LOCATION: (12)..(12)
<223> OTHER INFORMATION: Val (V), Ala (A), Ile (I) or Leu (L)
<220> FEATURE:
<221> NAME/KEY: MISC_FEATURE
<222> LOCATION: (13)..(13)
<223> OTHER INFORMATION: Ser (S) or Thr (T)
<220> FEATURE:
<221> NAME/KEY: MISC_FEATURE
<222> LOCATION: (14)..(14)
<223> OTHER INFORMATION: Gly (G) or Ala (A)
<220> FEATURE:
<221> NAME/KEY: MISC_FEATURE
<222> LOCATION: (15)..(15)
<223> OTHER INFORMATION: Val (V), Ala (A), Ile (I) or Leu (L)
<220> FEATURE:
<221> NAME/KEY: MISC_FEATURE
<222> LOCATION: (17)..(17)
<223> OTHER INFORMATION: Lys (K), Arg (R) or His (H)
<220> FEATURE:
<221> NAME/KEY: MISC_FEATURE
<222> LOCATION: (18)..(18)
<223> OTHER INFORMATION: Val (V), Ala (A), Ile (I) or Leu (L)
<220> FEATURE:
<221> NAME/KEY: MISC_FEATURE
<222> LOCATION: (19)..(19)
<223> OTHER INFORMATION: Ser (S) or Thr (T)
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Val (V), Ala (A), Ile (I) or Leu (L)
<220> FEATURE:
<221> NAME/KEY: MISC_FEATURE
<222> LOCATION: (22)..(22)
<223> OTHER INFORMATION: Asp(D) or Glu (E)
```

```
<220> FEATURE:
<221> NAME/KEY: MISC_FEATURE
<222> LOCATION: (23)..(23)
<223> OTHER INFORMATION: Asp(D) or Glu (E)
<220> FEATURE:
<221> NAME/KEY: MISC_FEATURE
<222> LOCATION: (24)..(24)
<223> OTHER INFORMATION: Asp(D) or Glu (E)
<220> FEATURE:
<221> NAME/KEY: MISC_FEATURE
<222> LOCATION: (25)..(25)
<223> OTHER INFORMATION: Lys (K), Arg (R) or His (H)
<220> FEATURE:
<221> NAME/KEY: MISC_FEATURE
<222> LOCATION: (26)..(26)
<223> OTHER INFORMATION: Val (V), Ala (A), Ile (I) or Leu (L)
<220> FEATURE:
<221> NAME/KEY: MISC_FEATURE
<222> LOCATION: (27)..(27)
<223> OTHER INFORMATION: Met (M) or Leu (L)
<220> FEATURE:
<221> NAME/KEY: MISC_FEATURE
<222> LOCATION: (28)..(28)
<223> OTHER INFORMATION: Val (V), Ala (A), Ile (I) or Leu (L)
<220> FEATURE:
<221> NAME/KEY: MISC_FEATURE
<222> LOCATION: (29)..(29)
<223> OTHER INFORMATION: Gly (G) or Ala (A)
<220> FEATURE:
<221> NAME/KEY: MISC_FEATURE
<222> LOCATION: (30)..(30)
<223> OTHER INFORMATION: Met (M) or Leu (L)
<220> FEATURE:
<221> NAME/KEY: MISC_FEATURE
<222> LOCATION: (31)..(31)
<223> OTHER INFORMATION: Gly (G) or Ala (A)
<220> FEATURE:
<221> NAME/KEY: MISC_FEATURE
<222> LOCATION: (32)..(32)
<223> OTHER INFORMATION: Val (V), Ala (A), Ile (I) or Leu (L)
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: MISC_FEATURE
<222> LOCATION: (34)..(34)
<223> OTHER INFORMATION: Asp(D) or Glu (E)
<220> FEATURE:
<221> NAME/KEY: MISC_FEATURE
<222> LOCATION: (35)..(35)
<223> OTHER INFORMATION: Gly (G) or Ala (A)
<220> FEATURE:
<221> NAME/KEY: MISC_FEATURE
<222> LOCATION: (36)..(36)
<223> OTHER INFORMATION: Lys (K), Arg (R) or His (H)
<220> FEATURE:
<221> NAME/KEY: MISC_FEATURE
<222> LOCATION: (37)..(37)
<223> OTHER INFORMATION: Val (V), Ala (A), Ile (I) or Leu (L)
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: MISC_FEATURE
<222> LOCATION: (40)..(40)
<223> OTHER INFORMATION: Tyr (Y) or Phe (F)
<220> FEATURE:
<221> NAME/KEY: MISC_FEATURE
<222> LOCATION: (41)..(41)
<223> OTHER INFORMATION: Lys (K), Arg (R) or His (H)
<220> FEATURE:
<221> NAME/KEY: MISC_FEATURE
<222> LOCATION: (42)..(42)
<223> OTHER INFORMATION: Ser (S) or Thr (T)
<220> FEATURE:
<221> NAME/KEY: MISC_FEATURE
<222> LOCATION: (44)..(44)
```

<223> OTHER INFORMATION: Trp (W) or Tyr (Y)

<400> SEQUENCE: 10

```
Xaa Xaa Xaa Xaa Xaa Cys Tyr Ile Tyr His Xaa Xaa Xaa Xaa Xaa Cys
1               5                   10                  15
Xaa Xaa Xaa Cys Xaa Xaa Xaa Xaa Xaa Xaa Xaa Xaa Xaa Xaa Xaa Xaa
            20                  25                  30
Cys Xaa Xaa Xaa Xaa Cys Cys Xaa Xaa Xaa Pro Xaa
        35                  40
```

<210> SEQ ID NO 11
<211> LENGTH: 44
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (1)..(1)
<223> OTHER INFORMATION: Asp(D) or Glu (E)
<220> FEATURE:
<221> NAME/KEY: MISC_FEATURE
<222> LOCATION: (2)..(2)
<223> OTHER INFORMATION: Ser (S) or Thr (T)
<220> FEATURE:
<221> NAME/KEY: MISC_FEATURE
<222> LOCATION: (3)..(3)
<223> OTHER INFORMATION: Gly (G) or Ala (A)
<220> FEATURE:
<221> NAME/KEY: MISC_FEATURE
<222> LOCATION: (4)..(4)
<223> OTHER INFORMATION: Asn (N) or Gln (Q)
<220> FEATURE:
<221> NAME/KEY: MISC_FEATURE
<222> LOCATION: (5)..(5)
<223> OTHER INFORMATION: Ser (S) or Thr (T)
<220> FEATURE:
<221> NAME/KEY: MISC_FEATURE
<222> LOCATION: (11)..(11)
<223> OTHER INFORMATION: Gly (G) or Ala (A)
<220> FEATURE:
<221> NAME/KEY: MISC_FEATURE
<222> LOCATION: (12)..(12)
<223> OTHER INFORMATION: Val (V), Ala (A), Ile (I) or Leu (L)
<220> FEATURE:
<221> NAME/KEY: MISC_FEATURE
<222> LOCATION: (13)..(13)
<223> OTHER INFORMATION: Ser (S) or Thr (T)
<220> FEATURE:
<221> NAME/KEY: MISC_FEATURE
<222> LOCATION: (14)..(14)
<223> OTHER INFORMATION: Gly (G) or Ala (A)
<220> FEATURE:
<221> NAME/KEY: MISC_FEATURE
<222> LOCATION: (15)..(15)
<223> OTHER INFORMATION: Val (V), Ala (A), Ile (I) or Leu (L)
<220> FEATURE:
<221> NAME/KEY: MISC_FEATURE
<222> LOCATION: (17)..(17)
<223> OTHER INFORMATION: Lys (K), Arg (R) or His (H)
<220> FEATURE:
<221> NAME/KEY: MISC_FEATURE
<222> LOCATION: (18)..(18)
<223> OTHER INFORMATION: Val (V), Ala (A), Ile (I) or Leu (L)
<220> FEATURE:
<221> NAME/KEY: MISC_FEATURE
<222> LOCATION: (19)..(19)
<223> OTHER INFORMATION: Ser (S) or Thr (T)
<220> FEATURE:
<221> NAME/KEY: MISC_FEATURE
<222> LOCATION: (21)..(21)
<223> OTHER INFORMATION: Val (V), Ala (A), Ile (I) or Leu (L)
<220> FEATURE:
<221> NAME/KEY: MISC_FEATURE
<222> LOCATION: (22)..(22)

```
<223> OTHER INFORMATION: Asp(D) or Glu (E)
<220> FEATURE:
<221> NAME/KEY: MISC_FEATURE
<222> LOCATION: (23)..(23)
<223> OTHER INFORMATION: Asp(D) or Glu (E)
<220> FEATURE:
<221> NAME/KEY: MISC_FEATURE
<222> LOCATION: (24)..(24)
<223> OTHER INFORMATION: Asp(D) or Glu (E)
<220> FEATURE:
<221> NAME/KEY: MISC_FEATURE
<222> LOCATION: (25)..(25)
<223> OTHER INFORMATION: Lys (K), Arg (R) or His (H)
<220> FEATURE:
<221> NAME/KEY: MISC_FEATURE
<222> LOCATION: (26)..(26)
<223> OTHER INFORMATION: Val (V), Ala (A), Ile (I) or Leu (L)
<220> FEATURE:
<221> NAME/KEY: MISC_FEATURE
<222> LOCATION: (27)..(27)
<223> OTHER INFORMATION: Met (M) or Leu (L)
<220> FEATURE:
<221> NAME/KEY: MISC_FEATURE
<222> LOCATION: (28)..(28)
<223> OTHER INFORMATION: Val (V), Ala (A), Ile (I) or Leu (L)
<220> FEATURE:
<221> NAME/KEY: MISC_FEATURE
<222> LOCATION: (29)..(29)
<223> OTHER INFORMATION: Gly (G) or Ala (A)
<220> FEATURE:
<221> NAME/KEY: MISC_FEATURE
<222> LOCATION: (30)..(30)
<223> OTHER INFORMATION: Met (M) or Leu (L)
<220> FEATURE:
<221> NAME/KEY: MISC_FEATURE
<222> LOCATION: (31)..(31)
<223> OTHER INFORMATION: Gly (G) or Ala (A)
<220> FEATURE:
<221> NAME/KEY: MISC_FEATURE
<222> LOCATION: (32)..(32)
<223> OTHER INFORMATION: Val (V), Ala (A), Ile (I) or Leu (L)
<220> FEATURE:
<221> NAME/KEY: MISC_FEATURE
<222> LOCATION: (34)..(34)
<223> OTHER INFORMATION: Asp(D) or Glu (E)
<220> FEATURE:
<221> NAME/KEY: MISC_FEATURE
<222> LOCATION: (35)..(35)
<223> OTHER INFORMATION: Gly (G) or Ala (A)
<220> FEATURE:
<221> NAME/KEY: MISC_FEATURE
<222> LOCATION: (36)..(36)
<223> OTHER INFORMATION: Lys (K), Arg (R) or His (H)
<220> FEATURE:
<221> NAME/KEY: MISC_FEATURE
<222> LOCATION: (37)..(37)
<223> OTHER INFORMATION: Val (V), Ala (A), Ile (I) or Leu (L)
<220> FEATURE:
<221> NAME/KEY: MISC_FEATURE
<222> LOCATION: (40)..(40)
<223> OTHER INFORMATION: Tyr (Y) or Phe (F)
<220> FEATURE:
<221> NAME/KEY: MISC_FEATURE
<222> LOCATION: (41)..(41)
<223> OTHER INFORMATION: Lys (K), Arg (R) or His (H)
<220> FEATURE:
<221> NAME/KEY: MISC_FEATURE
<222> LOCATION: (42)..(42)
<223> OTHER INFORMATION: Ser (S) or Thr (T)
<220> FEATURE:
<221> NAME/KEY: MISC_FEATURE
<222> LOCATION: (44)..(44)
<223> OTHER INFORMATION: Trp (W) or Tyr (Y)

<400> SEQUENCE: 11

Xaa Xaa Xaa Xaa Xaa Cys Tyr Ile Tyr His Xaa Xaa Xaa Xaa Xaa Cys
1               5                   10                  15
```

```
Xaa Xaa Xaa Cys Xaa Xaa Xaa Xaa Xaa Xaa Xaa Xaa Xaa Xaa Xaa
            20                  25                  30

Cys Xaa Xaa Xaa Xaa Cys Cys Xaa Xaa Xaa Pro Xaa
        35                  40
```

```
<210> SEQ ID NO 12
<211> LENGTH: 44
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (1)..(1)
<223> OTHER INFORMATION: Asp(D) or Glu (E)
<220> FEATURE:
<221> NAME/KEY: MISC_FEATURE
<222> LOCATION: (3)..(3)
<223> OTHER INFORMATION: Gly (G) or Ala (A)
<220> FEATURE:
<221> NAME/KEY: MISC_FEATURE
<222> LOCATION: (4)..(4)
<223> OTHER INFORMATION: Asn (N) or Gln (Q)
<220> FEATURE:
<221> NAME/KEY: MISC_FEATURE
<222> LOCATION: (11)..(11)
<223> OTHER INFORMATION: Gly (G) or Ala (A)
<220> FEATURE:
<221> NAME/KEY: MISC_FEATURE
<222> LOCATION: (12)..(12)
<223> OTHER INFORMATION: Val (V), Ala (A), Ile (I) or Leu (L)
<220> FEATURE:
<221> NAME/KEY: MISC_FEATURE
<222> LOCATION: (13)..(13)
<223> OTHER INFORMATION: Ser (S) or Thr (T)
<220> FEATURE:
<221> NAME/KEY: MISC_FEATURE
<222> LOCATION: (14)..(14)
<223> OTHER INFORMATION: Gly (G) or Ala (A)
<220> FEATURE:
<221> NAME/KEY: MISC_FEATURE
<222> LOCATION: (15)..(15)
<223> OTHER INFORMATION: Val (V), Ala (A), Ile (I) or Leu (L)
<220> FEATURE:
<221> NAME/KEY: MISC_FEATURE
<222> LOCATION: (17)..(17)
<223> OTHER INFORMATION: Lys (K), Arg (R) or His (H)
<220> FEATURE:
<221> NAME/KEY: MISC_FEATURE
<222> LOCATION: (18)..(18)
<223> OTHER INFORMATION: Val (V), Ala (A), Ile (I) or Leu (L)
<220> FEATURE:
<221> NAME/KEY: MISC_FEATURE
<222> LOCATION: (21)..(21)
<223> OTHER INFORMATION: Val (V), Ala (A), Ile (I) or Leu (L)
<220> FEATURE:
<221> NAME/KEY: MISC_FEATURE
<222> LOCATION: (22)..(22)
<223> OTHER INFORMATION: Asp(D) or Glu (E)
<220> FEATURE:
<221> NAME/KEY: MISC_FEATURE
<222> LOCATION: (23)..(23)
<223> OTHER INFORMATION: Asp(D) or Glu (E)
<220> FEATURE:
<221> NAME/KEY: MISC_FEATURE
<222> LOCATION: (24)..(24)
<223> OTHER INFORMATION: Asp(D) or Glu (E)
<220> FEATURE:
<221> NAME/KEY: MISC_FEATURE
<222> LOCATION: (25)..(25)
<223> OTHER INFORMATION: Lys (K), Arg (R) or His (H)
<220> FEATURE:
<221> NAME/KEY: MISC_FEATURE
<222> LOCATION: (26)..(26)
<223> OTHER INFORMATION: Val (V), Ala (A), Ile (I) or Leu (L)
<220> FEATURE:
<221> NAME/KEY: MISC_FEATURE
```

```
<222> LOCATION: (28)..(28)
<223> OTHER INFORMATION: Val (V), Ala (A), Ile (I) or Leu (L)
<220> FEATURE:
<221> NAME/KEY: MISC_FEATURE
<222> LOCATION: (29)..(29)
<223> OTHER INFORMATION: Gly (G) or Ala (A)
<220> FEATURE:
<221> NAME/KEY: MISC_FEATURE
<222> LOCATION: (31)..(31)
<223> OTHER INFORMATION: Gly (G) or Ala (A)
<220> FEATURE:
<221> NAME/KEY: MISC_FEATURE
<222> LOCATION: (32)..(32)
<223> OTHER INFORMATION: Val (V), Ala (A), Ile (I) or Leu (L)
<220> FEATURE:
<221> NAME/KEY: MISC_FEATURE
<222> LOCATION: (34)..(34)
<223> OTHER INFORMATION: Asp(D) or Glu (E)
<220> FEATURE:
<221> NAME/KEY: MISC_FEATURE
<222> LOCATION: (35)..(35)
<223> OTHER INFORMATION: Gly (G) or Ala (A)
<220> FEATURE:
<221> NAME/KEY: MISC_FEATURE
<222> LOCATION: (36)..(36)
<223> OTHER INFORMATION: Lys (K), Arg (R) or His (H)
<220> FEATURE:
<221> NAME/KEY: MISC_FEATURE
<222> LOCATION: (37)..(37)
<223> OTHER INFORMATION: Val (V), Ala (A), Ile (I) or Leu (L)
<220> FEATURE:
<221> NAME/KEY: MISC_FEATURE
<222> LOCATION: (40)..(40)
<223> OTHER INFORMATION: Tyr (Y) or Phe (F)
<220> FEATURE:
<221> NAME/KEY: MISC_FEATURE
<222> LOCATION: (41)..(41)
<223> OTHER INFORMATION: Lys (K), Arg (R) or His (H)
<220> FEATURE:
<221> NAME/KEY: MISC_FEATURE
<222> LOCATION: (42)..(42)
<223> OTHER INFORMATION: Ser (S) or Thr (T)

<400> SEQUENCE: 12

Xaa Ser Xaa Xaa Ser Cys Tyr Ile Tyr His Xaa Xaa Xaa Xaa Xaa Cys
1               5                   10                  15

Xaa Xaa Ser Cys Xaa Xaa Xaa Xaa Xaa Xaa Met Xaa Xaa Met Xaa Xaa
            20                  25                  30

Cys Xaa Xaa Xaa Xaa Cys Cys Xaa Xaa Xaa Pro Trp
        35                  40

<210> SEQ ID NO 13
<211> LENGTH: 44
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (1)..(1)
<223> OTHER INFORMATION: Asp(D) or Glu (E)
<220> FEATURE:
<221> NAME/KEY: MISC_FEATURE
<222> LOCATION: (3)..(3)
<223> OTHER INFORMATION: Gly (G) or Ala (A)
<220> FEATURE:
<221> NAME/KEY: MISC_FEATURE
<222> LOCATION: (4)..(4)
<223> OTHER INFORMATION: Asn (N) or Gln (Q)
<220> FEATURE:
<221> NAME/KEY: MISC_FEATURE
<222> LOCATION: (11)..(11)
<223> OTHER INFORMATION: Gly (G) or Ala (A)
<220> FEATURE:
<221> NAME/KEY: MISC_FEATURE
```

```
<222> LOCATION: (14)..(14)
<223> OTHER INFORMATION: Gly (G) or Ala (A)
<220> FEATURE:
<221> NAME/KEY: MISC_FEATURE
<222> LOCATION: (15)..(15)
<223> OTHER INFORMATION: Val (V), Ala (A), Ile (I) or Leu (L)
<220> FEATURE:
<221> NAME/KEY: MISC_FEATURE
<222> LOCATION: (17)..(17)
<223> OTHER INFORMATION: Lys (K), Arg (R) or His (H)
<220> FEATURE:
<221> NAME/KEY: MISC_FEATURE
<222> LOCATION: (18)..(18)
<223> OTHER INFORMATION: Val (V), Ala (A), Ile (I) or Leu (L)
<220> FEATURE:
<221> NAME/KEY: MISC_FEATURE
<222> LOCATION: (21)..(21)
<223> OTHER INFORMATION: Val (V), Ala (A), Ile (I) or Leu (L)
<220> FEATURE:
<221> NAME/KEY: MISC_FEATURE
<222> LOCATION: (22)..(22)
<223> OTHER INFORMATION: Asp(D) or Glu (E)
<220> FEATURE:
<221> NAME/KEY: MISC_FEATURE
<222> LOCATION: (23)..(23)
<223> OTHER INFORMATION: Asp(D) or Glu (E)
<220> FEATURE:
<221> NAME/KEY: MISC_FEATURE
<222> LOCATION: (24)..(24)
<223> OTHER INFORMATION: Asp(D) or Glu (E)
<220> FEATURE:
<221> NAME/KEY: MISC_FEATURE
<222> LOCATION: (25)..(25)
<223> OTHER INFORMATION: Lys (K), Arg (R) or His (H)
<220> FEATURE:
<221> NAME/KEY: MISC_FEATURE
<222> LOCATION: (26)..(26)
<223> OTHER INFORMATION: Val (V), Ala (A), Ile (I) or Leu (L)
<220> FEATURE:
<221> NAME/KEY: MISC_FEATURE
<222> LOCATION: (29)..(29)
<223> OTHER INFORMATION: Gly (G) or Ala (A)
<220> FEATURE:
<221> NAME/KEY: MISC_FEATURE
<222> LOCATION: (31)..(31)
<223> OTHER INFORMATION: Gly (G) or Ala (A)
<220> FEATURE:
<221> NAME/KEY: MISC_FEATURE
<222> LOCATION: (32)..(32)
<223> OTHER INFORMATION: Val (V), Ala (A), Ile (I) or Leu (L)
<220> FEATURE:
<221> NAME/KEY: MISC_FEATURE
<222> LOCATION: (34)..(34)
<223> OTHER INFORMATION: Asp(D) or Glu (E)
<220> FEATURE:
<221> NAME/KEY: MISC_FEATURE
<222> LOCATION: (35)..(35)
<223> OTHER INFORMATION: Gly (G) or Ala (A)
<220> FEATURE:
<221> NAME/KEY: MISC_FEATURE
<222> LOCATION: (35)..(35)
<223> OTHER INFORMATION: Gly (G) or Ala (A)
<220> FEATURE:
<221> NAME/KEY: MISC_FEATURE
<222> LOCATION: (36)..(36)
<223> OTHER INFORMATION: Lys (K), Arg (R) or His (H)
<220> FEATURE:
<221> NAME/KEY: MISC_FEATURE
<222> LOCATION: (37)..(37)
<223> OTHER INFORMATION: Val (V), Ala (A), Ile (I) or Leu (L)
<220> FEATURE:
<221> NAME/KEY: MISC_FEATURE
<222> LOCATION: (40)..(40)
<223> OTHER INFORMATION: Tyr (Y) or Phe (F)
<220> FEATURE:
<221> NAME/KEY: MISC_FEATURE
<222> LOCATION: (41)..(41)
<223> OTHER INFORMATION: Lys (K), Arg (R) or His (H)
<220> FEATURE:
```

<221> NAME/KEY: MISC_FEATURE
<222> LOCATION: (42)..(42)
<223> OTHER INFORMATION: Ser (S) or Thr (T)

<400> SEQUENCE: 13

Xaa Ser Xaa Xaa Ser Cys Tyr Ile Tyr His Xaa Val Ser Xaa Xaa Cys
1               5                   10                  15

Xaa Xaa Ser Cys Xaa Xaa Xaa Xaa Xaa Met Ala Xaa Met Xaa Xaa
            20                  25                  30

Cys Xaa Xaa Xaa Xaa Cys Cys Xaa Xaa Xaa Pro Trp
        35                  40

<210> SEQ ID NO 14
<211> LENGTH: 44
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (3)..(3)
<223> OTHER INFORMATION: Ser (S) or Thr (T)
<220> FEATURE:
<221> NAME/KEY: MISC_FEATURE
<222> LOCATION: (4)..(4)
<223> OTHER INFORMATION: Asn (N) or Gln (Q)
<220> FEATURE:
<221> NAME/KEY: MISC_FEATURE
<222> LOCATION: (11)..(11)
<223> OTHER INFORMATION: Ser (S) or Thr (T)
<220> FEATURE:
<221> NAME/KEY: MISC_FEATURE
<222> LOCATION: (14)..(14)
<223> OTHER INFORMATION: Ser (S) or Thr (T)
<220> FEATURE:
<221> NAME/KEY: MISC_FEATURE
<222> LOCATION: (15)..(15)
<223> OTHER INFORMATION: Val (V), Ala (A), Ile (I) or Leu (L)
<220> FEATURE:
<221> NAME/KEY: MISC_FEATURE
<222> LOCATION: (18)..(18)
<223> OTHER INFORMATION: Val (V), Ala (A), Ile (I) or Leu (L)
<220> FEATURE:
<221> NAME/KEY: MISC_FEATURE
<222> LOCATION: (21)..(21)
<223> OTHER INFORMATION: Val (V), Ala (A), Ile (I) or Leu (L)
<220> FEATURE:
<221> NAME/KEY: MISC_FEATURE
<222> LOCATION: (26)..(26)
<223> OTHER INFORMATION: Val (V), Ala (A), Ile (I) or Leu (L)
<220> FEATURE:
<221> NAME/KEY: MISC_FEATURE
<222> LOCATION: (29)..(29)
<223> OTHER INFORMATION: Ser (S) or Thr (T)
<220> FEATURE:
<221> NAME/KEY: MISC_FEATURE
<222> LOCATION: (31)..(31)
<223> OTHER INFORMATION: Ser (S) or Thr (T)
<220> FEATURE:
<221> NAME/KEY: MISC_FEATURE
<222> LOCATION: (32)..(32)
<223> OTHER INFORMATION: Val (V), Ala (A), Ile (I) or Leu (L)
<220> FEATURE:
<221> NAME/KEY: MISC_FEATURE
<222> LOCATION: (35)..(35)
<223> OTHER INFORMATION: Ser (S) or Thr (T)
<220> FEATURE:
<221> NAME/KEY: MISC_FEATURE
<222> LOCATION: (37)..(37)
<223> OTHER INFORMATION: Val (V), Ala (A), Ile (I) or Leu (L)
<220> FEATURE:
<221> NAME/KEY: MISC_FEATURE
<222> LOCATION: (40)..(40)
<223> OTHER INFORMATION: Tyr (Y) or Phe (F)
<220> FEATURE:

<221> NAME/KEY: MISC_FEATURE
<222> LOCATION: (42)..(42)
<223> OTHER INFORMATION: Ser (S) or Thr (T)

<400> SEQUENCE: 14

Glu Ser Xaa Xaa Ser Cys Tyr Ile Tyr His Xaa Val Ser Xaa Xaa Cys
1               5                   10                  15

Lys Xaa Ser Cys Xaa Glu Asp Glu Lys Xaa Met Ala Xaa Met Xaa Xaa
            20                  25                  30

Cys Glu Xaa His Xaa Cys Cys Xaa Lys Xaa Pro Trp
        35                  40

<210> SEQ ID NO 15
<211> LENGTH: 44
<212> TYPE: PRT
<213> ORGANISM: Artificial Sequence
<220> FEATURE:
<223> OTHER INFORMATION: helianthamide motif
<220> FEATURE:
<221> NAME/KEY: MISC_FEATURE
<222> LOCATION: (3)..(3)
<223> OTHER INFORMATION: Gly (G) or Ala (A)
<220> FEATURE:
<221> NAME/KEY: MISC_FEATURE
<222> LOCATION: (4)..(4)
<223> OTHER INFORMATION: Asn (N) or Gln (Q)
<220> FEATURE:
<221> NAME/KEY: MISC_FEATURE
<222> LOCATION: (11)..(11)
<223> OTHER INFORMATION: Gly (G) or Ala (A)
<220> FEATURE:
<221> NAME/KEY: MISC_FEATURE
<222> LOCATION: (14)..(14)
<223> OTHER INFORMATION: Gly (G) or Ala (A)
<220> FEATURE:
<221> NAME/KEY: MISC_FEATURE
<222> LOCATION: (15)..(15)
<223> OTHER INFORMATION: Ile (I) or Leu (L)
<220> FEATURE:
<221> NAME/KEY: MISC_FEATURE
<222> LOCATION: (18)..(18)
<223> OTHER INFORMATION: Ile (I) or Leu (L)
<220> FEATURE:
<221> NAME/KEY: MISC_FEATURE
<222> LOCATION: (21)..(21)
<223> OTHER INFORMATION: Ile (I) or Leu (L)
<220> FEATURE:
<221> NAME/KEY: MISC_FEATURE
<222> LOCATION: (26)..(26)
<223> OTHER INFORMATION: Ile (I) or Leu (L)
<220> FEATURE:
<221> NAME/KEY: MISC_FEATURE
<222> LOCATION: (29)..(29)
<223> OTHER INFORMATION: Gly (G) or Ala (A)
<220> FEATURE:
<221> NAME/KEY: MISC_FEATURE
<222> LOCATION: (31)..(31)
<223> OTHER INFORMATION: Gly (G) or Ala (A)
<220> FEATURE:
<221> NAME/KEY: MISC_FEATURE
<222> LOCATION: (32)..(32)
<223> OTHER INFORMATION: Ile (I) or Leu (L)
<220> FEATURE:
<221> NAME/KEY: MISC_FEATURE
<222> LOCATION: (35)..(35)
<223> OTHER INFORMATION: Gly (G) or Ala (A)
<220> FEATURE:
<221> NAME/KEY: MISC_FEATURE
<222> LOCATION: (37)..(37)
<223> OTHER INFORMATION: Ile (I) or Leu (L)
<220> FEATURE:
<221> NAME/KEY: MISC_FEATURE
<222> LOCATION: (42)..(42)
<223> OTHER INFORMATION: Ser (S) or Thr (T)

<400> SEQUENCE: 15

```
Glu Ser Xaa Xaa Ser Cys Tyr Ile Tyr His Xaa Val Ser Xaa Xaa Cys
1               5                   10                  15

Lys Xaa Ser Cys Xaa Glu Asp Glu Lys Xaa Met Ala Xaa Met Xaa Xaa
            20                  25                  30

Cys Glu Xaa His Xaa Cys Cys Tyr Lys Xaa Pro Trp
            35                  40
```

<210> SEQ ID NO 16
<211> LENGTH: 251
<212> TYPE: PRT
<213> ORGANISM: Artificial Sequence
<220> FEATURE:
<223> OTHER INFORMATION: Sequence of the barnase-helianthamide gene optimized for expression in E. coli; PRT1

<400> SEQUENCE: 16

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Tyr Val Glu Phe Asp Tyr Lys
                85                  90                  95

Asp Asp Asp Asp Lys Gly His His His His His Gly Gly Ser Asp
            100                 105                 110

Ser Glu Val Asn Gln Glu Ala Lys Pro Glu Val Lys Pro Glu Val Lys
            115                 120                 125

Pro Glu Thr His Ile Asn Leu Lys Val Ser Asp Gly Ser Ser Glu Ile
130                 135                 140

Phe Phe Lys Ile Lys Lys Thr Thr Pro Leu Arg Arg Leu Met Glu Ala
145                 150                 155                 160

Phe Ala Lys Arg Gln Gly Lys Glu Met Asp Ser Leu Thr Phe Leu Tyr
                165                 170                 175

Asp Gly Ile Glu Ile Gln Ala Asp Gln Thr Pro Glu Asp Leu Asp Met
            180                 185                 190

Glu Asp Asn Asp Ile Ile Glu Ala His Arg Glu Gln Ile Gly Gly Glu
            195                 200                 205

Ser Gly Asn Ser Cys Tyr Ile Tyr His Gly Val Ser Gly Ile Cys Lys
        210                 215                 220

Ala Ser Cys Ala Glu Asp Glu Lys Ala Met Ala Gly Met Gly Val Cys
225                 230                 235                 240

Glu Gly His Leu Cys Cys Tyr Lys Thr Pro Trp
                245                 250
```

<210> SEQ ID NO 17
<211> LENGTH: 166
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE

```
<222> LOCATION: (9)..(16)
<223> OTHER INFORMATION: FLAG TAG
<220> FEATURE:
<221> NAME/KEY: MISC_FEATURE
<222> LOCATION: (18)..(23)
<223> OTHER INFORMATION: HIS TAG
<220> FEATURE:
<221> NAME/KEY: MISC_FEATURE
<222> LOCATION: (26)..(122)
<223> OTHER INFORMATION: SUMO
<220> FEATURE:
<221> NAME/KEY: MISC_FEATURE
<222> LOCATION: (123)..(166)
<223> OTHER INFORMATION: HELIANTHAMIDE

<400> SEQUENCE: 17
```

| | | | | | | | | | | | | | | | |
|---|---|---|---|---|---|---|---|---|---|---|---|---|---|---|---|
| Glu | Ala | Glu | Ala | Tyr | Val | Glu | Phe | Asp | Tyr | Lys | Asp | Asp | Asp | Lys | |
| 1 | | | | 5 | | | | | 10 | | | | | 15 | |
| Gly | His | His | His | His | His | Gly | Gly | Ser | Asp | Ser | Glu | Val | Asn | Gln | |
| | | | 20 | | | | | 25 | | | | | 30 | | |
| Glu | Ala | Lys | Pro | Glu | Val | Lys | Pro | Glu | Val | Lys | Pro | Glu | Thr | His | Ile |
| | | 35 | | | | | 40 | | | | | 45 | | | |
| Asn | Leu | Lys | Val | Ser | Asp | Gly | Ser | Ser | Glu | Ile | Phe | Phe | Lys | Ile | Lys |
| | 50 | | | | | 55 | | | | | 60 | | | | |
| Lys | Thr | Thr | Pro | Leu | Arg | Arg | Leu | Met | Glu | Ala | Phe | Ala | Lys | Arg | Gln |
| 65 | | | | | 70 | | | | | 75 | | | | | 80 |
| Gly | Lys | Glu | Met | Asp | Ser | Leu | Thr | Phe | Leu | Tyr | Asp | Gly | Ile | Glu | Ile |
| | | | | 85 | | | | | 90 | | | | | 95 | |
| Gln | Ala | Asp | Gln | Thr | Pro | Glu | Asp | Leu | Asp | Met | Glu | Asp | Asn | Asp | Ile |
| | | | 100 | | | | | 105 | | | | | 110 | | |
| Ile | Glu | Ala | His | Arg | Glu | Gln | Ile | Gly | Gly | Glu | Ser | Gly | Asn | Ser | Cys |
| | | 115 | | | | | 120 | | | | | 125 | | | |
| Tyr | Ile | Tyr | His | Gly | Val | Ser | Gly | Ile | Cys | Lys | Ala | Ser | Cys | Ala | Glu |
| | 130 | | | | | 135 | | | | | 140 | | | | |
| Asp | Glu | Lys | Ala | Met | Ala | Gly | Met | Gly | Val | Cys | Glu | Gly | His | Leu | Cys |
| 145 | | | | | 150 | | | | | 155 | | | | | 160 |
| Cys | Tyr | Lys | Thr | Pro | Trp | | | | | | | | | | |
| | | | | 165 | | | | | | | | | | | |

```
<210> SEQ ID NO 18
<211> LENGTH: 576
<212> TYPE: DNA
<213> ORGANISM: Stichodactyla helianthus

<400> SEQUENCE: 18
atgaaacaat ccaccatcgc actggccctg ctgccgctgc tgttcacgcc ggttacaaag      60
ccgctggtgc atcatcatca tcatcactcg agtggcgcac aggttattaa cacctttgat     120
ggtgttgctg actatctgca aacgtaccat aaactgccgg ataattatat caccaaatca     180
gaagcacagg ccctggggtt ggtcgcatcg aaaggtaacc tggcagatgt ggctccgggc     240
aaaagtattg gcggtgacat cttctccaat cgtgaaggta aactgccggg caaatctggt     300
cgtacctggc gcgaagcgga tattaactat acgtcaggct ttcgtaattc ggatcgcatt     360
ctgtacagct ctgactggct gatctataaa accacgacg cctaccaaac cttcacgaaa      420
attcgtatcg aaggccgcga agtggtaac tcctgctata tttaccacgg cgttagcggt      480
atctgcaaag cgtcttgtgc cgaagatgaa aaagcaatgg caggcatggg cgtgtgtgaa     540
ggtcatctgt gttgttacaa accccgtgg tgatag                                576
```

<210> SEQ ID NO 19
<211> LENGTH: 36
<212> TYPE: PRT
<213> ORGANISM: homo sapiens

<400> SEQUENCE: 19

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 20
<211> LENGTH: 40
<212> TYPE: PRT
<213> ORGANISM: homo sapiens

<400> SEQUENCE: 20

Leu Gln Lys Tyr Tyr Cys Arg Val Arg Gly Gly Arg Cys Ala Val Leu
1               5                   10                  15

Ser Cys Leu Pro Lys Glu Glu Gln Ile Gly Lys Cys Ser Thr Arg Gly
            20                  25                  30

Arg Lys Cys Cys Arg Arg Lys Lys
        35                  40

<210> SEQ ID NO 21
<211> LENGTH: 48
<212> TYPE: PRT
<213> ORGANISM: Stichodactyla helianthus

<400> SEQUENCE: 21

Ala Ala Cys Lys Cys Asp Asp Glu Gly Pro Asp Ile Arg Thr Ala Pro
1               5                   10                  15

Leu Thr Gly Thr Val Asp Leu Gly Ser Cys Asn Ala Gly Trp Glu Lys
            20                  25                  30

Cys Ala Ser Tyr Tyr Thr Ile Ile Ala Asp Cys Cys Arg Lys Lys Lys
        35                  40                  45

<210> SEQ ID NO 22
<211> LENGTH: 29
<212> TYPE: PRT
<213> ORGANISM: homo sapiens

<400> SEQUENCE: 22

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 23
<211> LENGTH: 32
<212> TYPE: PRT
<213> ORGANISM: Amaranthus hypochondriacus

<400> SEQUENCE: 23

Cys Ile Pro Lys Trp Asn Arg Cys Gly Pro Lys Met Asp Gly Val Pro
1               5                   10                  15

Cys Cys Glu Pro Tyr Thr Cys Thr Ser Asp Tyr Tyr Gly Asn Cys Ser
            20                  25                  30

```
<210> SEQ ID NO 24
<211> LENGTH: 8
<212> TYPE: PRT
<213> ORGANISM: Artificial Sequence
<220> FEATURE:
<223> OTHER INFORMATION: MS/MS sequence for disulfide analysis of
      helianthamide

<400> SEQUENCE: 24

Cys Ala Glu Asp Glu Lys Ala Met
1               5

<210> SEQ ID NO 25
<211> LENGTH: 5
<212> TYPE: PRT
<213> ORGANISM: Artificial Sequence
<220> FEATURE:
<223> OTHER INFORMATION: MS/MS sequence for disulfide analysis of
      helianthamide

<400> SEQUENCE: 25

Ser Gly Asn Ser Cys
1               5

<210> SEQ ID NO 26
<211> LENGTH: 9
<212> TYPE: PRT
<213> ORGANISM: Artificial Sequence
<220> FEATURE:
<223> OTHER INFORMATION: MS/MS sequence for disulfide analysis of
      helianthamide

<400> SEQUENCE: 26

His Gly Val Ser Gly Ile Cys Lys Ala
1               5

<210> SEQ ID NO 27
<211> LENGTH: 4
<212> TYPE: PRT
<213> ORGANISM: Artificial Sequence
<220> FEATURE:
<223> OTHER INFORMATION: MS/MS sequence for disulfide analysis of
      helianthamide

<400> SEQUENCE: 27

Met Gly Val Cys
1

<210> SEQ ID NO 28
<211> LENGTH: 4
<212> TYPE: PRT
<213> ORGANISM: Stichodactyla helianthus
<220> FEATURE:
<221> NAME/KEY: MISC_FEATURE
<222> LOCATION: (1)..(4)
<223> OTHER INFORMATION: inhibitory motif

<400> SEQUENCE: 28

Tyr Ile Tyr His
1

<210> SEQ ID NO 29
<211> LENGTH: 9
<212> TYPE: PRT
<213> ORGANISM: Stichodactyla helianthus
<220> FEATURE:
<221> NAME/KEY: MISC_FEATURE
<222> LOCATION: (1)..(9)
<223> OTHER INFORMATION: LC-MS/MS peak
```

```
<400> SEQUENCE: 29

Ile Tyr His Gly Val Ser Gly Ile Cys
1               5

<210> SEQ ID NO 30
<211> LENGTH: 4
<212> TYPE: PRT
<213> ORGANISM: Stichodactyla helianthus
<220> FEATURE:
<221> NAME/KEY: MISC_FEATURE
<222> LOCATION: (1)..(4)
<223> OTHER INFORMATION: LC-MS/MS peak

<400> SEQUENCE: 30

Gly Ile Cys Lys
1

<210> SEQ ID NO 31
<211> LENGTH: 9
<212> TYPE: PRT
<213> ORGANISM: Stichodactyla helianthus
<220> FEATURE:
<221> NAME/KEY: MISC_FEATURE
<222> LOCATION: (1)..(9)
<223> OTHER INFORMATION: LC-MS/MS peak

<400> SEQUENCE: 31

Lys Ala Met Ala Gly Met Gly Val Cys
1               5

<210> SEQ ID NO 32
<211> LENGTH: 7
<212> TYPE: PRT
<213> ORGANISM: Stichodactyla helianthus
<220> FEATURE:
<221> NAME/KEY: MISC_FEATURE
<222> LOCATION: (1)..(7)
<223> OTHER INFORMATION: LC-MS/MS peak

<400> SEQUENCE: 32

Cys Tyr Ile Tyr His Gly Val
1               5

<210> SEQ ID NO 33
<211> LENGTH: 8
<212> TYPE: PRT
<213> ORGANISM: Stichodactyla helianthus
<220> FEATURE:
<221> NAME/KEY: MISC_FEATURE
<222> LOCATION: (1)..(8)
<223> OTHER INFORMATION: LC-MS/MS peak

<400> SEQUENCE: 33

Ile Cys Lys Ala Ser Cys Ala Glu
1               5

<210> SEQ ID NO 34
<211> LENGTH: 5
<212> TYPE: PRT
<213> ORGANISM: Stichodactyla helianthus
<220> FEATURE:
<221> NAME/KEY: MISC_FEATURE
<222> LOCATION: (1)..(5)
<223> OTHER INFORMATION: LC-MS/MS peak

<400> SEQUENCE: 34

Asn Ser Cys Tyr Ile
```

```
<210> SEQ ID NO 35
<211> LENGTH: 5
<212> TYPE: PRT
<213> ORGANISM: Stichodactyla helianthus
<220> FEATURE:
<221> NAME/KEY: MISC_FEATURE
<222> LOCATION: (1)..(5)
<223> OTHER INFORMATION: LC-MS/MS peak

<400> SEQUENCE: 35

Leu Cys Cys Tyr Lys
1               5

<210> SEQ ID NO 36
<211> LENGTH: 11
<212> TYPE: PRT
<213> ORGANISM: Stichodactyla helianthus
<220> FEATURE:
<221> NAME/KEY: MISC_FEATURE
<222> LOCATION: (1)..(11)
<223> OTHER INFORMATION: LC-MS/MS peak

<400> SEQUENCE: 36

Glu Lys Ala Met Ala Gly Met Gly Val Cys Glu
1               5                   10

<210> SEQ ID NO 37
<211> LENGTH: 7
<212> TYPE: PRT
<213> ORGANISM: Stichodactyla helianthus
<220> FEATURE:
<221> NAME/KEY: MISC_FEATURE
<222> LOCATION: (1)..(7)
<223> OTHER INFORMATION: LC-MS/MS peak

<400> SEQUENCE: 37

Glu Gly His Leu Cys Cys Tyr
1               5

<210> SEQ ID NO 38
<211> LENGTH: 4
<212> TYPE: PRT
<213> ORGANISM: Stichodactyla helianthus
<220> FEATURE:
<221> NAME/KEY: MISC_FEATURE
<222> LOCATION: (1)..(4)
<223> OTHER INFORMATION: LC-MS/MS peak

<400> SEQUENCE: 38

Ser Cys Ala Glu
1

<210> SEQ ID NO 39
<211> LENGTH: 6
<212> TYPE: PRT
<213> ORGANISM: Stichodactyla helianthus
<220> FEATURE:
<221> NAME/KEY: MISC_FEATURE
<222> LOCATION: (1)..(6)
<223> OTHER INFORMATION: LC-MS/MS peak

<400> SEQUENCE: 39

Glu Ser Gly Asn Ser Cys
1               5

<210> SEQ ID NO 40
```

```
<211> LENGTH: 5
<212> TYPE: PRT
<213> ORGANISM: Stichodactyla helianthus
<220> FEATURE:
<221> NAME/KEY: MISC_FEATURE
<222> LOCATION: (1)..(5)
<223> OTHER INFORMATION: LC-MS/MS peak

<400> SEQUENCE: 40

Gly His Leu Cys Cys
1               5

<210> SEQ ID NO 41
<211> LENGTH: 4
<212> TYPE: PRT
<213> ORGANISM: Stichodactyla helianthus
<220> FEATURE:
<221> NAME/KEY: MISC_FEATURE
<222> LOCATION: (1)..(4)
<223> OTHER INFORMATION: LC-MS/MS peak

<400> SEQUENCE: 41

Gly Asn Ser Cys
1

<210> SEQ ID NO 42
<211> LENGTH: 6
<212> TYPE: PRT
<213> ORGANISM: Stichodactyla helianthus
<220> FEATURE:
<221> NAME/KEY: MISC_FEATURE
<222> LOCATION: (1)..(6)
<223> OTHER INFORMATION: LC-MS/MS peak

<400> SEQUENCE: 42

Gly His Leu Cys Cys Tyr
1               5

<210> SEQ ID NO 43
<211> LENGTH: 5
<212> TYPE: PRT
<213> ORGANISM: Stichodactyla helianthus
<220> FEATURE:
<221> NAME/KEY: MISC_FEATURE
<222> LOCATION: (1)..(5)
<223> OTHER INFORMATION: LC-MS/MS peak

<400> SEQUENCE: 43

Lys Ala Ser Cys Ala
1               5

<210> SEQ ID NO 44
<211> LENGTH: 8
<212> TYPE: PRT
<213> ORGANISM: Stichodactyla helianthus
<220> FEATURE:
<221> NAME/KEY: MISC_FEATURE
<222> LOCATION: (1)..(8)
<223> OTHER INFORMATION: LC-MS/MS peak

<400> SEQUENCE: 44

Gly Val Cys Glu Gly His Leu Cys
1               5

<210> SEQ ID NO 45
<211> LENGTH: 5
<212> TYPE: PRT
<213> ORGANISM: Stichodactyla helianthus
<220> FEATURE:
```

```
<221> NAME/KEY: MISC_FEATURE
<222> LOCATION: (1)..(5)
<223> OTHER INFORMATION: LC-MS/MS peak

<400> SEQUENCE: 45

Ser Gly Ile Cys Lys
1               5

<210> SEQ ID NO 46
<211> LENGTH: 7
<212> TYPE: PRT
<213> ORGANISM: Stichodactyla helianthus
<220> FEATURE:
<221> NAME/KEY: MISC_FEATURE
<222> LOCATION: (1)..(7)
<223> OTHER INFORMATION: LC-MS/MS peak

<400> SEQUENCE: 46

Ser Glu Ser Gly Asn Ser Cys
1               5

<210> SEQ ID NO 47
<211> LENGTH: 6
<212> TYPE: PRT
<213> ORGANISM: Stichodactyla helianthus
<220> FEATURE:
<221> NAME/KEY: MISC_FEATURE
<222> LOCATION: (1)..(6)
<223> OTHER INFORMATION: LC-MS/MS peak

<400> SEQUENCE: 47

Leu Cys Cys Tyr Lys Thr
1               5

<210> SEQ ID NO 48
<211> LENGTH: 6
<212> TYPE: PRT
<213> ORGANISM: Stichodactyla helianthus
<220> FEATURE:
<221> NAME/KEY: MISC_FEATURE
<222> LOCATION: (1)..(6)
<223> OTHER INFORMATION: LC-MS/MS peak

<400> SEQUENCE: 48

Ser Cys Ala Glu Asp Glu
1               5

<210> SEQ ID NO 49
<211> LENGTH: 12
<212> TYPE: PRT
<213> ORGANISM: Stichodactyla helianthus
<220> FEATURE:
<221> NAME/KEY: MISC_FEATURE
<222> LOCATION: (1)..(12)
<223> OTHER INFORMATION: LC-MS/MS peak

<400> SEQUENCE: 49

Ser Glu Ser Gly Asn Ser Cys Tyr Ile Tyr His Gly
1               5                   10
```

MAMMALIAN GLUCOSIDASE INHIBITORS, METHODS FOR THEIR USE AND PHARMACEUTICAL COMPOSITIONS THEREOF

CROSS REFERENCE TO RELATED APPLICATIONS

This application is a national phase application corresponding to International Application No. PCT/CA2016/000183, filed Jun. 29, 2016; which claims the benefit of U.S. Provisional Patent Application Ser. No. 62/185,931, filed Jun. 29, 2015, and U.S. Provisional Patent Application Ser. No. 62/332,600 filed May 6, 2016.

The Sequence Listing for this application is labeled "SeqList-14Nov19-ST25.txt", which was created on Nov. 14, 2019, and is 35 KB. The entire content is incorporated herein by reference in its entirety.

TECHNICAL FIELD

The present invention relates to methods for inhibiting of alpha-glucosidases in subjects. In particular, the invention relates to the use of human pancreatic alpha-amylase inhibitors to reduce starch hydrolysis in subjects and further relates to the treatment of conditions associated therewith.

BACKGROUND

Diabetes mellitus is a metabolic disorder caused by the inability to produce adequate levels of insulin or effectively use insulin being produced. The result is abnormally high blood glucose levels, which can lead to a number of serious consequences, such as nerve and blood vessel damage, heart disease, kidney disease, stroke, and blindness (6). Obesity associated type II diabetes, in particular, has become increasingly common in our industrial world and accounts for 90% of all diabetes cases (7, 8). Type II diabetes results from pancreatic β-cell impairment and a gradual loss of cellular responsiveness to insulin. While certain genetic factors are linked to an increased risk for type II diabetes, dietary and lifestyle choices have been shown to strongly impact the onset of this disease in all individuals (7, 8). As type II diabetes cases are associated with insulin insensitivity, and because high levels of insulin have been linked to obesity (9), therapeutic interventions that act independently of this hormone are preferred. This can be done through controlling the influx of glucose into the bloodstream from either the liver (e.g. metformin) or from one's diet (e.g. acarbose) (10, 11).

Starch is a prominent source of glucose and calories in many people's diets. The digestion of starch is a multistep process that begins in the oral cavity with the hydrolysis of insoluble starch polymers into shorter oligomers by salivary α-amylase (12). Upon reaching the small intestine, pancreatic α-amylase provides a more extensive hydrolysis, cleaving the starch into a mixture of gluco-oligosaccharides, primarily maltose and maltotriose. The resulting mixture then passes into the brush border of the small intestine where it is processed into glucose by the resident α-glucosidases maltase/glucoamylase and sucrose/isomaltase. The currently used therapeutics were developed primarily as inhibitors of these α-glucosidases rather than α-amylase since in this way it was possible to limit the processing into glucose both of starch and of dietary sugars such as sucrose (13, 14). The α-glucosidase inhibitors currently in medical use, miglitol, voglibose and acarbose, are all small molecule azasugar-based inhibitors, and unfortunately all are associated with deleterious side effects, ranging from diarrhea to hepatotoxicity (15, 16). While this is in part due to the natural consequences of displacement of sugars to the lower gut where anaerobic fermentation can take place, the problems are also due to systemic absorption and a lack of specificity. As a consequence of these side effects these drugs suffer from relatively poor patient compliance, hence there is a need for more targeted therapeutics of this general class.

Human pancreatic α-amylase, which catalyzes the endohydrolysis of (1-4)-α-D-glucosidic linkages in starch, represents a good therapeutic target within the starch degradation pathway since it is the enzyme at the top of the starch digestion pyramid (1, 2). It is active within the lumen of the duodenum, thus orally administered inhibitors that stay within the gastro-intestinal tract will be optimally localized for amylase inhibition and will be less likely to cause undesirable side-effects. Specific inhibition of this enzyme over the brush border α-glucosidases limits starch digestion, while allowing oligosaccharides to be processed thereby minimizing the gastrointestinal effects seen with currently used therapeutic inhibitors (3). Achieving such a level of specificity with mechanism-based inhibitors is challenging since these digestive glycosidases use the same mechanism. However, it seemed possible that more specific inhibitors might have evolved in the context of anti-feedant strategies in the natural world. Specific and potent inhibitors of human pancreatic alpha amylase (HPA), the enzyme that hydrolyses the (1-4)-α-D-glucosidic linkages of ingested starch, show promise in the control of blood glucose levels in diabetic and pre-diabetic individuals while minimizing the side effects of more general alpha glucosidase.

SUMMARY

The present invention is based, in part, on the surprising discovery that the peptides described herein have alpha-amylase inhibitory activity. Furthermore, the peptides described herein appear to be specific for mammalian alpha-amylase, whereby they show no activity on Human maltase-glucoamylase, *Roseburia inulinivorans* α-amylase A, *Butyrivibrio fibrisolvens* α-amylase B, *Bacillus licheniformis* α-amylase, Bovine liver β-galactosidase, Green coffee bean α-galactosidase, Jack bean α-mannosidase, Brewer's yeast α-glucosidase, and Almond β-glucosidase. Accordingly, the present peptides are promising candidates for the selective inhibition of mammalian alpha-amylase.

In accordance with a first embodiment, there is provided a composition including: (a) a peptide including a contiguous stretch of amino acids having the consensus amino acid sequence: Xaa.1a-Xaa.1b-Xaa.2-Xaa.3-Xaa.4-Xaa.5-C-Y-I-Y-H-Xaa.6-Xaa.7-Xaa.8-Xaa.9-Xaa.10a-Xaa.10b-Xaa.11-Xaa.12-Xaa.13a-Xaa.13b-Xaa.14-Xaa.15-Xaa.16-Xaa.17-Xaa.18-Xaa.19-Xaa.20-Xaa.21-Xaa.22-Xaa.23-Xaa.24-Xaa.25a-Xaa.25b-Xaa.26-Xaa.27-Xaa.28-Xaa.29a-Xaa.29b-Xaa.29c-Xaa.30-Xaa.31-Xaa.32a-Xaa.32b-Xaa.33 (SEQ ID NO: 3), wherein the peptide may be up to 85 amino acids in length, and wherein Xaa.1a may be Ser (S) or Thr (T) or absent, Xaa.1b may be Asp(D) or Glu (E) or absent, Xaa.2 may be Ser (S) or Thr (T) or absent, Xaa.3 may be Gly (G) or Ala (A) or absent, Xaa.4 may be Asn (N) or Gln (Q) or absent, Xaa.5 may be Ser (S) or Thr (T) or absent, Xaa.6 may be Gly (G) or Ala (A) or absent, Xaa.7 may be Val (V), Ala (A), Ile (I) or Leu (L) or absent, Xaa.8 may be Ser (S) or Thr (T) or absent, Xaa.9 may be Gly (G) or Ala (A) or absent, Xaa.10a may be Val (V), Ala (A), Ile (I) or Leu (L) or absent, Xaa.10b may be Cys (C) or absent, Xaa.11 may be Lys (K), Arg (R) or His (H) or absent, Xaa.12 may be Val (V), Ala (A), Ile (I) or Leu (L) or absent, Xaa.13a may be Ser (S) or Thr (T) or absent, Xaa.13b may be Cys (C) or absent, Xaa.14 may be Val (V), Ala (A), Ile (I) or Leu (L) or absent, Xaa.15 may be Asp(D) or Glu (E) or absent, Xaa.16 may be Asp(D) or Glu (E) or absent, Xaa.17 may be Asp(D) or Glu (E) or absent, Xaa.18 may be Lys (K), Arg (R) or His (H) or absent, Xaa.19 may be Val (V), Ala (A), Ile (I) or Leu (L) or absent, Xaa.20 may be Met (M) or Leu (L) or absent, Xaa.21 may be Val (V), Ala (A), Ile (I) or Leu (L) or absent, Xaa.22 may be Gly (G) or Ala (A) or absent, Xaa.23 may be Met (M) or Leu (L) or absent, Xaa.24 may be Gly (G) or Ala (A) or absent, Xaa.25a may be Val (V), Ala (A), Ile (I) or Leu (L) or absent, Xaa.25b may be Cys (C) or absent, Xaa.26 may be Asp(D) or Glu (E) or absent, Xaa.27 may be Gly (G) or Ala (A) or absent, Xaa.28 may be Lys (K), Arg (R) or His (H) or absent, Xaa.29a may be Val (V), Ala (A), Ile (I) or Leu (L) or absent, Xaa.29b may be Cys (C) or absent, Xaa.29c may be Cys (C) or absent, Xaa.30 may be Tyr (Y) or Phe (F) or absent, Xaa.31 may be Lys (K), Arg (R) or His (H) or absent, Xaa.32a may be Ser (S) or Thr (T) or absent, Xaa.32b may be Pro (P) or absent, and Xaa.33 may be Trp (W) or Tyr (Y) or absent; and (b) a pharmaceutically acceptable excipient.

The peptide may be up to 285 amino acids in length. The peptide may be up to 185 amino acids in length. The peptide may be up to 150 amino acids in length. The peptide may be up to 100 amino acids in length. The peptide may be up to 85 amino acids in length. The peptide may be up to 80 amino acids in length. The peptide may be up to 75 amino acids in length. The peptide may be up to 70 amino acids in length. The peptide may be up to 65 amino acids in length. The peptide may be up to 500 amino acids in length. The peptide may be up to 45 amino acids in length. The peptide may be up to 44 amino acids in length. The peptide may be up to 40 amino acids in length.

In accordance with a further embodiment, there is provided a composition including: (a) a peptide including a contiguous stretch of amino acids having the consensus amino acid sequence: Y-I-Y-H-G-V-S-G-I (SEQ ID NO: 4); and (b) a pharmaceutically acceptable excipient.

In accordance with a further embodiment, there is provided a composition including: (a) a peptide including a contiguous stretch of amino acids having the consensus amino acid sequence: Y-I-Y-H-G-V (SEQ ID NO: 5); and (b) a pharmaceutically acceptable excipient.

In accordance with a further embodiment, there is provided a composition including: (a) a peptide including a contiguous stretch of amino acids having the consensus amino acid sequence: C-Y-I-Y-H-Xaa.6-Xaa.7-Xaa.8-Xaa.9-Xaa.10 (SEQ ID NO: 7); and (b) a pharmaceutically acceptable excipient, wherein the peptide may be up to 10 amino acids in length, and wherein Xaa.6 may be Gly (G) or Ala (A), Xaa.7 may be Val (V), Ala (A), Ile (I) or Leu (L), Xaa.8 may be Ser (S) or Thr (T), Xaa.9 may be Gly (G) or Ala (A) and Xaa.10 may be Val (V), Ala (A), Ile (I) or Leu (L).

In accordance with a further embodiment, there is provided a composition including: (a) a peptide including a contiguous stretch of amino acids having the consensus amino acid sequence: C-Y-I-Y-H-G-V-S-G-I-C(SEQ ID NO: 8); and (b) a pharmaceutically acceptable excipient.

In accordance with a further embodiment, there is provided a composition including: (a) a peptide including a contiguous stretch of amino acids having the consensus amino acid sequence: Xaa.1a-Xaa.1b-Xaa.2-Xaa.3-Xaa.4-Xaa.5-C-Y-I-Y-H-Xaa.6-Xaa.7-Xaa.8-Xaa.9-Xaa.10 (SEQ ID NO: 9), wherein the peptide may be up to 16 amino acids in length, and wherein Xaa.1a may be Ser (S) or Thr (T) or absent, Xaa.1b may be Asp(D) or Glu (E), Xaa.2 may be Ser (S) or Thr (T), Xaa.3 may be Gly (G) or Ala (A), Xaa.4 may be Asn (N) or Gln (Q), Xaa.5 may be Ser (S) or Thr (T), Xaa.6 may be Gly (G) or Ala (A), Xaa.7 may be Val (V), Ala (A), Ile (I) or Leu (L), Xaa.8 may be Ser (S) or Thr (T), Xaa.9 may be Gly (G) or Ala (A) and Xaa.10 may be Val (V), Ala (A), Ile (I) or Leu (L).

In accordance with a further embodiment, there is provided a composition including: (a) a peptide including a contiguous stretch of amino acids having the consensus amino acid sequence: Xaa.1-Xaa.2-Xaa.3-Xaa.4-Xaa.5-C-Y-I-Y-H-Xaa.6-Xaa.7-Xaa.8-.Xaa.9-Xaa.10-C-Xaa.11-Xaa.12-Xaa.13-C-Xaa.14-Xaa.15-Xaa.16-Xaa.17-Xaa.18-Xaa.19-Xaa.20-Xaa.21-Xaa.22-Xaa.23-Xaa.24-Xaa.25-C-Xaa.26-Xaa.27-Xaa.28-Xaa.29-C-C-Xaa.3-Xaa.31-Xaa32-P-Xaa.33 (SEQ ID NO: to), wherein the peptide may be up to 44 amino acids in length, and wherein Xaa.1 may be Asp(D) or Glu (E), Xaa.2 may be Ser (S) or Thr (T), Xaa.3 may be Gly (G) or Ala (A), Xaa.4 may be Asn (N) or Gin (Q), Xaa.5 may be Ser (S) or Thr (T), Xaa.6 may be Gly (G) or Ala (A), Xaa.7 may be Val (V), Ala (A), Ile (I) or Leu (L), Xaa.8 may be Ser (S) or Thr (T), Xaa.9 may be Gly (G) or Ala (A), Xaa.10 may be Val (V), Ala (A), Ile (I) or Leu (L), Xaa.1 may be Lys (K), Arg (R) or His (H), Xaa.12 may be Val (V), Ala (A), Ile (I) or Leu (L), Xaa.13 may be Ser (S) or Thr (T), Xaa.14 may be Val (V), Ala (A), Ile (I) or Leu (L), Xaa.15 may be Asp(D) or Glu (E), Xaa.16 may be Asp(D) or Glu (E), Xaa.17 may be Asp(D) or Glu (E), Xaa.18 may be Lys (K), Arg (R) or His (H), Xaa.19 may be Val (V), Ala (A), Ile (I) or Leu (L), Xaa.20 may be Met (M) or Leu (L), Xaa.21 may be Val (V), Ala (A), Ile (I) or Leu (L), Xaa.22 may be Gly (G) or Ala (A), Xaa.23 may be Met (M) or Leu (L), Xaa.24 may be Gly (G) or Ala (A), Xaa.25 may be Val (V), Ala (A), lie (I) or Leu (L), Xaa.26 may be Asp(D) or Glu (E), Xaa.27 may be Gly (G) or Ala (A), Xaa.28 may be Lys (K), Arg (R) or His (H), Xaa.29 may be Val (V), Ala (A), Ile (I) or Leu (L), Xaa.30 may be Tyr (Y) or Phe (F), Xaa.31 may be Lys (K), Arg (R) or His (H), Xaa.32 may be Ser (S) or Thr (T) and Xaa.33 may be Trp (W) or Tyr (Y); and (b) a pharmaceutically acceptable excipient.

In accordance with a further embodiment, there is provided a composition including: (a) a peptide including a contiguous stretch of amino acids having the consensus amino acid sequence: Xaa.1-Xaa.2-Xaa.3-Xaa.4-Xaa.5-C-Y-I-Y-H-Xaa.6-Xaa7-Xaa.8-Xaa.9-Xaa.10-C-Xaa.11-Xaa.12-Xaa.13-C-Xaa.14-Xaa.15-Xaa.16-Xaa.17-Xaa.18-Xaa.19-Xaa.20-Xaa.21-Xaa.22-Xaa.23-Xaa.24-Xaa.25-C-Xaa.26-Xaa.27-Xaa.28-Xaa.29-C-C-Xaa.30-Xaa.31-Xaa.32-P-Xaa.33 (SEQ ID NO: 11), wherein the peptide may be up to 44 amino acids in length, and wherein Xaa.1 may be Asp(D) or Glu (E), Xaa.2 may be Ser (S) or Thr (T), Xaa.3 may be Gly (G) or Ala (A), Xaa.4 may be Asn (N) or Gln (Q), Xaa.5 may be Ser (S) or Thr (T), Xaa.6 may be Gly (G) or Ala (A), Xaa.7 may be Val (V), Ala (A), Ile (I) or Leu (L), Xaa.8 may be Ser (S) or Thr (T), Xaa.9 may be Gly (G) or Ala (A), Xaa.10 may be Val (V), Ala (A), Ile (I) or Leu (L), Xaa.11 may be Lys (K), Arg (R) or His (H), Xaa.12 may be Val (V), Ala (A), Ile (I) or Leu (L), Xaa.13 may be Ser (S) or Thr (T), Xaa.14 may be Val (V), Ala (A), Ile (I) or Leu (L), Xaa.15 may be Asp(D) or Glu (E), Xaa.16 may be Asp(D) or Glu (E), Xaa.17 may be Asp(D) or Glu (E), Xaa.18 may be Lys (K), Arg (R) or His (H), Xaa.19 may be Val (V), Ala (A), Ile (I) or Leu (L), Xaa.20 may be Met (M) or Leu (L), Xaa.21 may be Val (V), Ala (A), Ile (I) or Leu (L), Xaa.22 may be Gly (G) or Ala (A), Xaa.23 may be Met (M) or Leu (L), Xaa.24 may be Gly (G) or Ala (A), Xaa.25 may be Val (V), Ala (A), Ile (I) or Leu (L), Xaa.26 may be Asp(D) or Glu (E), Xaa.27 may be Gly (G) or Ala (A), Xaa.28 may be Lys (K), Arg (R) or His (H), Xaa.29 may be Val (V), Ala (A), Ile (I) or Leu (L), Xaa.30 may be Tyr (Y) or Phe (F), Xaa.31 may be Lys (K), Arg (R) or His (H), Xaa.32 may be Ser (S) or Thr (T) and Xaa.33 may be Trp (W) or Tyr (Y); and (b) a pharmaceutically acceptable excipient.

In accordance with a further embodiment, there is provided a composition including: (a) a peptide including a contiguous stretch of amino acids having the consensus amino acid sequence: Xaa.1-S-Xaa.3-Xaa.4-S-C-Y-I-Y-H-Xaa.6-Xaa.7-Xaa.8-Xaa.9-Xaa.10-C-Xaa.11-Xaa.12-S-C-Xaa.14-Xaa.15-Xaa.16-Xaa.17-Xaa.18-Xaa.19-M-Xaa.21-Xaa.22-M-Xaa24-Xaa.25-C-Xaa.26-Xaa.27-Xaa.28-Xaa.29-C-C-Xaa.30-Xaa.31-Xaa.32-P-W (SEQ ID NO: 12), wherein the peptide may be up to 44 amino acids in length, and wherein Xaa.1 may be Asp(D) or Glu (E), Xaa.3 may be Gly (G) or Ala (A), Xaa.4 may be Asn (N) or Gin (Q), Xaa.6 may be Gly (G) or Ala (A), Xaa.7 may be Val (V), Ala (A), Ile (I) or Leu (L), Xaa.8 may be Ser (S) or Thr (T), Xaa.9 may be Gly (G) or Ala (A), Xaa.10 may be Val (V), Ala (A), Ile (I) or Leu (L), Xaa.11 may be Lys (K), Arg (R) or His (H), Xaa.12 may be Val (V), Ala (A), Ile (I) or Leu (L), Xaa.14 may be Val (V), Ala (A), Ile (I) or Leu (L), Xaa.15 may be Asp(D) or Glu (E), Xaa.16 may be Asp(D) or Glu (E), Xaa.17 may be Asp(D) or Glu (E), Xaa.18 may be Lys (K), Arg (R) or His (H), Xaa.19 may be Val (V), Ala (A), Ile (I) or Leu (L), Xaa.21 may be Val (V), Ala (A), Ile (I) or Leu (L), Xaa.22 may be Gly (G) or Ala (A), Xaa.24 may be Gly (G) or Ala (A), Xaa.25 may be Val (V), Ala (A), Ile (I) or Leu (L), Xaa.26 may be Asp(D) or Glu (E), Xaa.27 may be Gly (G) or Ala (A), Xaa.28 may be Lys (K), Arg (R) or His (H), Xaa.29 may be Val (V), Ala (A), Ile (I) or Leu (L), Xaa.30 may be Tyr (Y) or Phe (F), Xaa.31 may be Lys (K), Arg (R) or His (H), and Xaa.32 may be Ser (S) or Thr (T); and (b) a pharmaceutically acceptable excipient.

In accordance with a further embodiment, there is provided a composition including: (a) a peptide including a contiguous stretch of amino acids having the consensus amino acid sequence: Xaa.1-S-Xaa.3-Xaa.4-S-C-Y-I-Y-H-Xaa.6-V-S-Xaa.9-Xaa.10-C-Xaa.11-Xaa.12-S-C-Xaa.14-Xaa.15-Xaa.16-Xaa.17-Xaa.18-Xaa.19-M-A-Xaa.22-M-Xaa.24-Xaa.25-C-Xaa.26-Xaa.27-Xaa.28-Xaa.29-C-C-Xaa.30-Xaa.31-Xaa.32-P-W (SEQ ID NO: 13), wherein the peptide may be up to 44 amino acids in length, and wherein Xaa.1 may be Asp(D) or Glu (E), Xaa.3 may be Gly (G) or Ala (A), Xaa.4 may be Asn (N) or Gin (Q), Xaa.6 may be Gly (G) or Ala (A), Xaa.9 may be Gly (G) or Ala (A), Xaa.10 may be Val (V), Ala (A), Ile (I) or Leu (L), Xaa.11 may be Lys (K), Arg (R) or His (H), Xaa.12 may be Val (V), Ala (A), Ile (I) or Leu (L), Xaa.14 may be Val (V), Ala (A), Ile (I) or Leu (L), Xaa.15 may be Asp(D) or Glu (E), Xaa.16 may be Asp(D) or Glu (E), Xaa.17 may be Asp(D) or Glu (E), Xaa.18 may be Lys (K), Arg (R) or His (H), Xaa.19 may be Val (V), Ala (A), Ile (I) or Leu (L), Xaa.22 may be Gly (G) or Ala (A), Xaa.24 may be Gly (G) or Ala (A), Xaa.25 may be Val (V), Ala (A), Ile (I) or Leu (L), Xaa.26 may be Asp(D) or Glu (E), Xaa.27 may be Gly (G) or Ala (A), Xaa.28 may be Lys (K), Arg (R) or His (H), Xaa.29 may be Val (V), Ala (A), Ile (I) or Leu (L), Xaa.30 may be Tyr (Y) or Phe (F), Xaa.31 may be Lys (K), Arg (R) or His (H), and Xaa.32 may be Ser (S) or Thr (T); and (b) a pharmaceutically acceptable excipient.

In accordance with a further embodiment, there is provided a composition including: (a) a peptide including a contiguous stretch of amino acids having the consensus amino acid sequence: E-S-Xaa.3-Xaa.4-S-C-Y-I-Y-H-Xaa.6-V-S-Xaa.9-Xaa.10-C-K-Xaa.12-S-C-Xaa.14-E-D-E-K-Xaa.19-M-A-Xaa.22-M-Xaa.24-Xaa25-C-E-Xaa.27-H-Xaa.29-C-C-Xaa.30-K-Xaa32-P-W (SEQ ID NO: 14), wherein the peptide may be up to 44 amino acids in length, and wherein Xaa.3 may be Gly (G) or Ala (A), Xaa.4 may be Asn (N) or Gin (Q), Xaa.6 may be Gly (G) or Ala (A), Xaa.9 may be Gly (G) or Ala (A), Xaa.10 may be Val (V), Ala (A), Ile (I) or Leu (L), Xaa.12 may be Val (V), Ala (A), Ile (I) or Leu (L), Xaa.14 may be Val (V), Ala (A), Ile (I) or Leu (L), Xaa.19 may be Val (V), Ala (A), Ile (I) or Leu (L), Xaa.21 may be Val (V), Ala (A), Ile (I) or Leu (L), Xaa.22 may be Gly (G) or Ala (A), Xaa.24 may be Gly (G) or Ala (A), Xaa.25 may be Val (V), Ala (A), Ile (I) or Len (L), Xaa.27 may be Gly (G) or Ala (A), Xaa.29 may be Val (V), Ala (A), Ile (I) or Leu (L), Xaa.30 may be Tyr (Y) or Phe (F), and Xaa.32 may be Ser (S) or Thr (T); and (b) a pharmaceutically acceptable excipient.

In accordance with a further embodiment, there is provided a composition including: (a) a peptide including a contiguous stretch of amino acids having the consensus amino acid sequence: E-S-Xaa.3-Xaa.4-S-C-Y-I-Y-H-Xaa.6-V-S-Xaa.9-Xaa.10-C-K-Xaa2-S-C-Xaa.4-E-D-E-K-Xaa.19-M-A-Xaa.22-M-Xaa.24-Xaa.25-C-E-Xaa.27-H-Xaa.29-C-C-Y-K-Xaa.32-P-W (SEQ ID NO: 15), wherein the peptide may be up to 44 amino acids in length, and wherein Xaa.3 may be Gly (G) or Ala (A), Xaa.4 may be Asn (N) or Gin (Q), Xaa.6 may be Gly (G) or Ala (A), Xaa.9 may be Gly (G) or Ala (A), Xaa.10 may be Ile (I) or Leu (L), Xaa.12 may be Ile (I) or Leu (L), Xaa.14 may be Ile (I) or Leu (L), Xaa.19 may be Ile (I) or Leu (L), Xaa.21 may be Ile (I) or Leu (L), Xaa.22 may be Gly (G) or Ala (A), Xaa.24 may be Gly (G) or Ala (A), Xaa.25 may be lie (I) or Leu (L), Xaa.27 may be Gly (G) or Ala (A), Xaa.29 may be Ile (I) or Leu (L), and Xaa.32 is Ser (S) or Thr (T); and (b) a pharmaceutically acceptable excipient.

In accordance with a further embodiment, there is provided a composition including: (a) a peptide including a contiguous stretch of amino acids having the consensus amino acid sequence: ESGNSCYIYHGVSGICKASCAE-DEKAMAGMGVCEGHLCCYKTPW (SEQ ID NO: 1); and (b) a pharmaceutically acceptable excipient.

In accordance with a further embodiment, there is provided a composition including: (a) a peptide including a contiguous stretch of amino acids having the consensus amino acid sequence: SESGNSCYIYHGVSGICKASCAE-DEKAMAGMGVCEGHLCCYKTPW (SEQ ID NO: 2); and (b) a pharmaceutically acceptable excipient.

In accordance with another embodiment, there is provided a peptide including a contiguous stretch of amino acids having the consensus amino acid sequence Xaa.1a-Xaa.1b-Xaa.2-Xaa.3-Xaa.4-Xaa.5-C-Y-I-Y-H-Xaa.6-Xaa.7-Xaa.8-Xaa.9-Xaa.10a-Xaa.10b-Xaa.11-Xaa.12-Xaa.13a-Xaa.13b-Xaa.14-Xaa.15-Xaa.16-Xaa.17-Xaa.18-Xaa.19-Xaa.20-Xaa.21-Xaa.22-Xaa.23-Xaa.24-Xaa.25a-Xaa.25b-Xaa.26-Xaa.27-Xaa.28-Xaa.29a-Xaa.29b-Xaa.29c-Xaa.30-Xaa.31-Xaa.32a-Xaa.32b-Xaa.33 (SEQ ID NO: 3), wherein Xaa.1a may be Ser (S) or Thr (T) or absent, Xaa.1b may be Asp(D) or Glu (E) or absent, Xaa.2 may be Ser (S) or Thr (T) or absent, Xaa.3 may be Gly (G) or Ala (A) or absent, Xaa.4 may be Asn (N) or Gin (Q) or absent, Xaa.5 may be Ser (S) or Thr (T) or absent, Xaa.6 may be Gly (G) or Ala (A) or absent, Xaa.7 may be Val (V), Ala (A), Ile (I) or Leu (L) or absent, Xaa.8 may be Ser (S) or Thr (T) or absent, Xaa.9 may be Gly (G) or Ala (A) or absent, Xaa.10a may be Val (V), Ala (A), Ile (I) or Leu (L) or absent, Xaa.10b may be Cys (C) or absent, Xaa.11 may be Lys (K), Arg (R) or His (H) or absent, Xaa.12 may be Val (V), Ala (A), Ile (I) or Leu (L) or absent, Xaa.13a may be Ser (S) or Thr (T) or absent, Xaa.13b may be Cys (C) or absent, Xaa.14 may be Val (V), Ala (A), Ile (I) or Leu (L) or absent, Xaa.15 may be Asp(D) or Glu (E) or absent, Xaa.16 may be Asp(D) or Glu (E) or absent, Xaa.17 may be Asp(D) or Glu (E) or absent, Xaa.18 may be Lys (K), Arg (R) or His (H) or absent, Xaa.19 may be Val (V), Ala (A), Ile (I) or Leu (L) or absent, Xaa.20 may be Met (M) or Leu (L) or absent, Xaa.21 may be Val (V), Ala (A), Ile (I) or Leu (L) or absent, Xaa.22 may be Gly (G) or Ala (A) or absent, Xaa.23 may be Met (M) or Leu (L) or absent, Xaa.24 may be Gly (G) or Ala (A) or absent, Xaa.25a may be Val (V), Ala (A), Ile (I) or Leu (L) or absent, Xaa.25b may be Cys (C) or absent, Xaa.26 may be Asp(D) or Glu (E) or absent, Xaa.27 may be Gly (G) or Ala (A) or absent, Xaa.28 may be Lys (K), Arg (R) or His (H) or absent, Xaa.29a may be Val (V), Ala (A), Ile (I) or Leu (L) or absent, Xaa.29b may be Cys (C) or absent, Xaa.29c may be Cys (C) or absent, Xaa.30 may be Tyr (Y) or Phe (F) or absent, Xaa.31 may be Lys (K), Arg (R) or His (H) or absent, Xaa.32a may be Ser (S) or Thr (T) or absent, Xaa.32b may be Pro (P) or absent, and Xaa.33 may be Trp (W) or Tyr (Y) or absent; wherein the peptide has mammalian alpha-amylase inhibitory activity.

In accordance with another embodiment, there is provided a peptide having the amino acid sequence: Y-I-Y-H-G-V-S-G-I (SEQ ID NO: 4).

In accordance with another embodiment, there is provided a peptide having the amino acid sequence: Y-I-Y-H-G-V (SEQ ID NO: 5).

In accordance with another embodiment, there is provided a peptide having the amino acid sequence: C-Y-I-Y-H-Xaa.6-Xaa.7-Xaa.8-Xaa.9-Xaa.10 (SEQ ID NO: 7), wherein the peptide may be up to 10 amino acids in length, and wherein Xaa.6 may be Gly (G) or Ala (A), Xaa7 may be Val (V), Ala (A), Ile (I) or Leu (L), Xaa.8 may be Ser (S) or Thr (T), Xaa.9 may be Gly (G) or Ala (A) and Xaa.10 may be Val (V), Ala (A), Ile (I) or Leu (L).

In accordance with another embodiment, there is provided a peptide having the amino acid sequence: C-Y-I-Y-H-G-V-S-G-I-C(SEQ ID NO: 8).

In accordance with another embodiment, there is provided a peptide having the amino acid sequence: Xaa.1a-Xaa.1b-Xaa.2-Xaa.3-Xaa.4-Xaa.5-C-Y-I-Y-H-Xaa.6-Xaa.7-Xaa.8-Xaa.9-Xaa.10 (SEQ ID NO: 9), wherein the peptide may be up to 16 amino acids in length, and wherein Xaa.1a may be Ser (S) or Thr (T) or absent, Xaa.1b may be Asp(D) or Glu (E), Xaa.2 may be Ser (S) or Thr (T), Xaa.3 may be Gly (G) or Ala (A), Xaa.4 may be Asn (N) or Gin (Q), Xaa.5 may be Ser (S) or Thr (T), Xaa.6 may be Gly (G) or Ala (A), Xaa.7 may be Val (V), Ala (A), Ile (I) or Leu (L), Xaa.8 may be Ser (S) or Thr (T), Xaa.9 may be Gly (G) or Ala (A) and Xaa.10 may be Val (V), Ala (A), Ile (I) or Leu (L).

In accordance with another embodiment, there is provided a peptide having the amino acid sequence: Xaa.1-Xaa.2-Xaa.3-Xaa.4-Xaa.5-C-Y-I-Y-H-Xaa.6-Xaa.7-Xaa.8-Xaa.9-Xaa.10-C-Xaa.11-Xaa.12-Xaa.13-C-Xaa.14-Xaa.15-Xaa.16-Xaa.17-Xaa.18-Xaa.19-Xaa.20-Xaa.21-Xaa.22-Xaa.23-Xaa.24-Xaa.25-C-Xaa.26-Xaa.27-Xaa.28-Xaa.29-C-C-Xaa.30-Xaa.31-Xaa.32-P-Xaa.33 (SEQ ID NO: 10), wherein the peptide may be up to 44 amino acids in length, and wherein Xaa.1 may be Asp(D) or Glu (E), Xaa.2 may be Ser (S) or Thr (T), Xaa.3 may be Gly (G) or Ala (A), Xaa.4 may be Asn (N) or Gin (Q), Xaa.5 may be Ser (S) or Thr (T), Xaa.6 may be Gly (G) or Ala (A), Xaa.7 may be Val (V), Ala (A), Ile (I) or Leu (L), Xaa.8 may be Ser (S) or Thr (T), Xaa.9 may be Gly (G) or Ala (A), Xaa.10 may be Val (V), Ala (A), Ile (I) or Leu (L), Xaa.1 may be Lys (K), Arg (R) or His (H), Xaa.12 may be Val (V), Ala (A), Ile (I) or Leu (L), Xaa.13 may be Ser (S) or Thr (T), Xaa.14 may be Val (V), Ala (A), Ile (I) or Leu (L), Xaa.15 may be Asp(D) or Glu (E), Xaa.16 may be Asp(D) or Glu (E), Xaa.17 may be Asp(D) or Glu (E), Xaa.18 may be Lys (K), Arg (R) or His (H), Xaa.19 may be Val (V), Ala (A), Ile (I) or Leu (L), Xaa.20 may be Met (M) or Leu (L), Xaa.21 may be Val (V), Ala (A), Ile (I) or Leu (L), Xaa.22 may be Gly (G) or Ala (A), Xaa.23 may be Met (M) or Leu (L), Xaa.24 may be Gly (G) or Ala (A), Xaa.25 may be Val (V), Ala (A), Ile (I) or Leu (L), Xaa.26 may be Asp(D) or Glu (E), Xaa.27 may be Gly (G) or Ala (A), Xaa.28 may be Lys (K), Arg (R) or His (H), Xaa.29 may be Val (V), Ala (A), Ile (I) or Leu (L), Xaa.30 may be Tyr (Y) or Phe (F), Xaa.31 may be Lys (K), Arg (R) or His (H), Xaa.32 may be Ser (S) or Thr (T) and Xaa.33 may be Trp (W) or Tyr (Y).

In accordance with another embodiment, there is provided a peptide having the amino acid sequence: Xaa.1-Xaa.2-Xaa.3-Xaa.4-Xaa.5-C-Y-I-Y-H-Xaa.6-Xaa.7-Xaa.8-Xaa.9-Xaa.10-C-Xaa.11-Xaa.12-Xaa.13-C-Xaa.14-Xaa.15-Xaa.16-Xaa.17-Xaa.18-Xaa.19-Xaa.20-Xaa.21-Xaa.22-Xaa.23-Xaa.24-Xaa.25-C-Xaa.26-Xaa.27-Xaa.28-Xaa.29-C-C-Xaa.30-Xaa.31-Xaa.32-P-Xaa.33 (SEQ ID NO: 11), wherein the peptide may be up to 44 amino acids in length, and wherein Xaa.1 may be Asp(D) or Glu (E), Xaa.2 may be Ser (S) or Thr (T), Xaa.3 may be Gly (G) or Ala (A), Xaa.4 may be Asn (N) or Gln (Q), Xaa.5 may be Ser (S) or Thr (T), Xaa.6 may be Gly (G) or Ala (A), Xaa.7 may be Val (V), Ala (A), Ile (1) or Leu (L), Xaa.8 may be Ser (S) or Thr (T), Xaa.9 may be Gly (G) or Ala (A), Xaa.10 may be Val (V), Ala (A), Ile (I) or Leu (L), Xaa.1 may be Lys (K), Arg (R) or His (H), Xaa.12 may be Val (V), Ala (A), Ile (I) or Leu (L), Xaa.13 may be Ser (S) or Thr (T), Xaa.14 may be Val (V), Ala (A), Ile (I) or Leu (L), Xaa.15 may be Asp(D) or Glu (E), Xaa.16 may be Asp(D) or Glu (E), Xaa.17 may be Asp(D) or Glu (E), Xaa.18 may be Lys (K), Arg (R) or His (H), Xaa.19 may be Val (V), Ala (A), Ile (I) or Leu (L), Xaa.20 may be Met (M) or Leu (L), Xaa.21 may be Val (V), Ala (A), Ile (I) or Leu (L), Xaa.22 may be Gly (G) or Ala (A), Xaa.23 may be Met (M) or Leu (L), Xaa.24 may be Gly (G) or Ala (A), Xaa.25 may be Val (V), Ala (A), Ile (I) or Leu (L), Xaa.26 may be Asp(D) or Glu (E), Xaa.27 may be Gly (G) or Ala (A), Xaa.28 may be Lys (K), Arg (R) or His (H), Xaa.29 may be Val (V), Ala (A), Ile (I) or Leu (L), Xaa.300 may be Tyr (Y) or Phe (F), Xaa.31 may be Lys (K), Arg (R) or His (H), Xaa.32 may be Ser (S) or Thr (T) and Xaa.33 may be Trp (W) or Tyr (Y).

In accordance with another embodiment, there is provided a peptide having the amino acid sequence: Xaa.1-S-Xaa.3-Xaa.4-S-C-Y-I-Y-H-Xaa.6-Xaa.7-Xaa.8-Xaa.9-Xaa.10-C-Xaa.11-Xaa.12-S-C-Xaa.14-Xaa.15-Xaa.16-Xaa.17-Xaa.18-Xaa.19-M-Xaa.21-Xaa.22-M-Xaa.24-Xaa.25-C-Xaa.26-Xaa.27-Xaa.28-Xaa.29-C-C-Xaa.30-Xaa.32-P-W (SEQ ID NO: 12), wherein the peptide may be up to 44 amino acids in length, and wherein Xaa.1 may be Asp(D) or Glu (E), Xaa.3 may be Gly (G) or Ala (A), Xaa.4 may be Asn (N) or Gln (Q), Xaa.6 may be Gly (G) or Ala (A), Xaa.7 may be Val (V), Ala (A), Ile (I) or Leu (L), Xaa.8 may be Ser (S) or Thr (T), Xaa.9 may be Gly (G) or Ala (A), Xaa.10 may be Val (V), Ala (A), Ile (I) or Leu (L), Xaa.1 may be Lys (K), Arg (R) or His (H), Xaa.12 may be Val (V), Ala (A), Ile (I) or Leu (L), Xaa.14 may be Val (V), Ala (A), Ile (I) or Leu (L), Xaa.15 may be Asp(D) or Glu (E), Xaa.16 may be Asp(D) or Glu (E), Xaa.17 may be Asp(D) or Glu (E), Xaa.18 may be Lys (K), Arg(R) or His (H), Xaa.19 may be Val (V), Ala (A), Ile (I) or Leu (L), Xaa.21 may be Val (V), Ala (A), Ile (I) or Leu (L), Xaa.22 may be Gly (G) or Ala (A), Xaa.24 may be Gly (G) or Ala (A), Xaa.25 may be Val (V), Ala (A), Ile (I) or Leu (L), Xaa.26 may be Asp(D) or Glu (E), Xaa.27 may be Gly (G) or Ala (A), Xaa.28 may be Lys (K), Arg (R) or His (H), Xaa.29 may be Val (V), Ala (A), Ile (I) or Leu (L), Xaa.30 may be Tyr (Y) or Phe (F), Xaa.31 may be Lys (K), Arg (R) or His (H), and Xaa.32 may be Ser (S) or Thr (T).

In accordance with another embodiment, there is provided a peptide having the amino acid sequence: Xaa.1-S-Xaa.3-Xaa.4-S-C-Y-I-Y-H-Xaa.6-V-S-Xaa.9-Xaa.10-C-Xaa.11-Xaa.12-S-C-Xaa.14-Xaa.15-Xaa.16-Xaa.17-Xaa.18-Xaa.19-M-A-Xaa.22-M-Xaa.24-Xaa.25-C-Xaa.26-Xaa.27-Xaa.28-Xaa.29-C-C-Xaa.30-Xaa.31-Xaa.32-P-W (SEQ ID NO: 13), wherein the peptide may be up to 44 amino acids in length, and wherein Xaa.1 may be Asp(D) or Glu (E), Xaa.3 may be Gly (G) or Ala (A), Xaa.4 may be Asn (N) or Gln (Q), Xaa.6 may be Gly (G) or Ala (A), Xaa.9 may be Gly (G) or Ala (A), Xaa.10 may be Val (V), Ala (A), Ile (I) or Leu (L), Xaa.11 may be Lys (K), Arg (R) or His (H), Xaa.12 may be Val (V), Ala (A), Ile (I) or Leu (L), Xaa.14 may be Val (V), Ala (A), Ile (I) or Leu (L), Xaa.15 may be Asp(D) or Glu (E), Xaa.16 may be Asp(D) or Glu (E), Xaa.17 may be Asp(D) or Glu (E), Xaa.18 may be Lys (K), Arg (R) or His (H), Xaa.19 may be Val (V), Ala (A), Ile (I) or Leu (L), Xaa.22 may be Gly (G) or Ala (A), Xaa.24 may be Gly (G) or Ala (A), Xaa.25 may be Val (V), Ala (A), Ile (I) or Leu (L), Xaa.26 may be Asp(D) or Glu (E), Xaa.27 may be Gly (G) or Ala (A), Xaa.28 may be Lys (K), Arg (R) or His (H), Xaa.29 may be Val (V), Ala (A), Ile (I) or Leu (L), Xaa.30 may be Tyr (Y) or Phe (F), Xaa.31 may be Lys (K), Arg (R) or His (H), and Xaa.32 may be Ser (S) or Thr (T).

In accordance with another embodiment, there is provided a peptide having the amino acid sequence: E-S-Xaa.3-Xaa.4-S-C-Y-I-Y-H-Xaa.6-V-S-Xaa.9-Xaa.10-C-K-Xaa.12-S-C-Xaa.14-E-D-E-K-Xaa.19-M-A-Xaa.22-M-Xaa.24-Xaa.25-C-E-Xaa.27-H-Xaa.29-C-C-Xaa.30-K-Xaa.32-P-W (SEQ ID NO: 14), wherein the peptide may be up to 44 amino acids in length, and wherein Xaa.3 may be Gly (G) or Ala (A), Xaa.4 may be Asn (N) or Gin (Q), Xaa.6 may be Gly (G) or Ala (A), Xaa.9 may be Gly (G) or Ala (A), Xaa.10 may be Val (V), Ala (A), Ile (I) or Leu (L), Xaa.12 may be Val (V), Ala (A), Ile (I) or Leu (L), Xaa.14 may be Val (V), Ala (A), Ile (I) or Leu (L), Xaa.19 may be Val (V), Ala (A), Ile (I) or Leu (L), Xaa.21 may be Val (V), Ala (A), Ile (I) or Leu (L), Xaa.22 may be Gly (G) or Ala (A), Xaa24 may be Gly (G) or Ala (A), Xaa.25 may be Val (V), Ala (A), Ile (I) or Leu (L), Xaa.27 may be Gly (G) or Ala (A), Xaa.29 may be Val (V), Ala (A), Ile (I) or Leu (L), Xaa.30 may be Tyr (Y) or Phe (F), and Xaa.32 may be Ser (S) or Thr (T).

In accordance with another embodiment, there is provided a peptide having the amino acid sequence: E-S-Xaa.3-Xaa.4-S-C-Y-I-Y-H-Xaa.6-V-S-Xaa.9-Xaa.10-C-K-Xaa.12-S-C-Xaa.14-E-D-E-K-Xaa.19-M-A-Xaa.22-M-Xaa.24-Xaa.25-C-E-Xaa.27-H-Xaa.29-C-C-Y-K-Xaa.32-P-W (SEQ ID NO: 15), wherein the peptide may be up to 44 amino acids in length, and wherein Xaa.3 may be Gly (G) or Ala (A), Xaa.4 may be Asn (N) or Gln (Q), Xaa.6 may be Gly (G) or Ala (A), Xaa.9 may be Gly (G) or Ala (A), Xaa.10 may be Ile (I) or Leu (L), Xaa.12 may be Ile (I) or Leu (L), Xaa.14 may be Ile (I) or Leu (L), Xaa.19 may be Ile (I) or Leu (L), Xaa.21 may be Ile (I) or Leu (L), Xaa.22 may be Gly (G) or Ala (A), Xaa.24 may be Gly (G) or Ala (A), Xaa.25 may be Ile (I) or Leu (L), Xaa.27 may be Gly (G) or Ala (A), Xaa.29 may be Ile (I) or Leu (L), and Xaa.32 may be Ser (S) or Thr (T).

In accordance with another embodiment, there is provided a peptide having the amino acid sequence: ESGNSCYIYHGVSGICKASCAEDEKAMAGMGVCEGHLCCYKTPW (SEQ ID NO: 1).

In accordance with another embodiment, there is provided a peptide having the amino acid sequence: SESGNSCYIYHGVSGICKASCAEDEKAMAGMGVCEGHLCCYKTPW (SEQ ID NO: 2).

The Cys (C) amino acids may form disulfide bridges. The Cys (C) amino acids C6 and C38 may form a disulfide bridge, C16 and C33 may form a disulfide bridge and C20 and C39 may form a disulfide bridge.

In accordance with another embodiment, there is provided a substantially purified peptide, wherein the peptide comprises a contiguous stretch of amino acids having the amino acid sequence: ESGNSCYIYHGVSGICKASCAEDEKAMAGMGVCEGHLCCYKTPW (SEQ ID NO: 1).

In accordance with another embodiment, there is provided a method of inhibiting mammalian alpha-amylase activity, the method comprising: administering a peptide as described herein to a subject, wherein the subject is in need of alpha-amylase inhibition, wherein the peptide has alpha-amylase inhibitory activity.

In accordance with another embodiment, there is provided a use of a peptide described herein for the curative or prophylactic treatment of a subject, wherein the subject is in need of alpha-amylase inhibition, wherein the peptide has alpha-amylase inhibitory activity.

In accordance with another embodiment, there is provided a use of peptide described herein or a pharmaceutical composition containing the peptide, for the manufacture of a medicament for the curative or prophylactic treatment of a subject, wherein the subject is in need of alpha-amylase inhibition, and wherein the peptide has alpha-amylase inhibitory activity.

In accordance with another embodiment, there is provided a pharmaceutical composition for the inhibition of alpha-amylase, the pharmaceutical composition comprising a peptide described herein, together with a pharmaceutically acceptable diluent or carrier, wherein the peptide has alpha-amylase inhibitory activity.

In accordance with another embodiment, there is provided a commercial package containing, as active pharmaceutical ingredient, a peptide described herein, wherein the peptide has alpha-amylase inhibitory activity, together with instructions for alpha-amylase inhibition in a subject.

The subject in need of alpha-amylase inhibition, may have or may be at risk of developing one or more of the following: Middleton syndrome; a motility disorder of the gastrointestinal tract; postprandial reactive hypoglycemia; postprandial syndrome; irritable bowel syndrome; diabetes mellitus type 1; diabetes mellitus type 2; pre-diabetes; obesity; dumping syndrome; infant dumping syndrome; polycystic ovary syndrome; steatohepatitis; and viral infection. The motility disorder may be gastroesophageal reflux disease or gastroparesis. The viral infection may be HIV infection or hepatitis B infection. The steatohepatitis may be non-alcoholic fatty liver disease. The subject in need of alpha-amylase inhibition may have had a gastric bypass or a gastrectomy. The peptide or the medicament may be adapted for oral treatment.

10,000 extracts from the UBC Marine Natural Products Library were tested in duplicate against HPA. Crude extracts with a residual activity of 80% or lower of uninhibited activity (within the dashed box) were selected for further purification and analysis.

Figure 2:
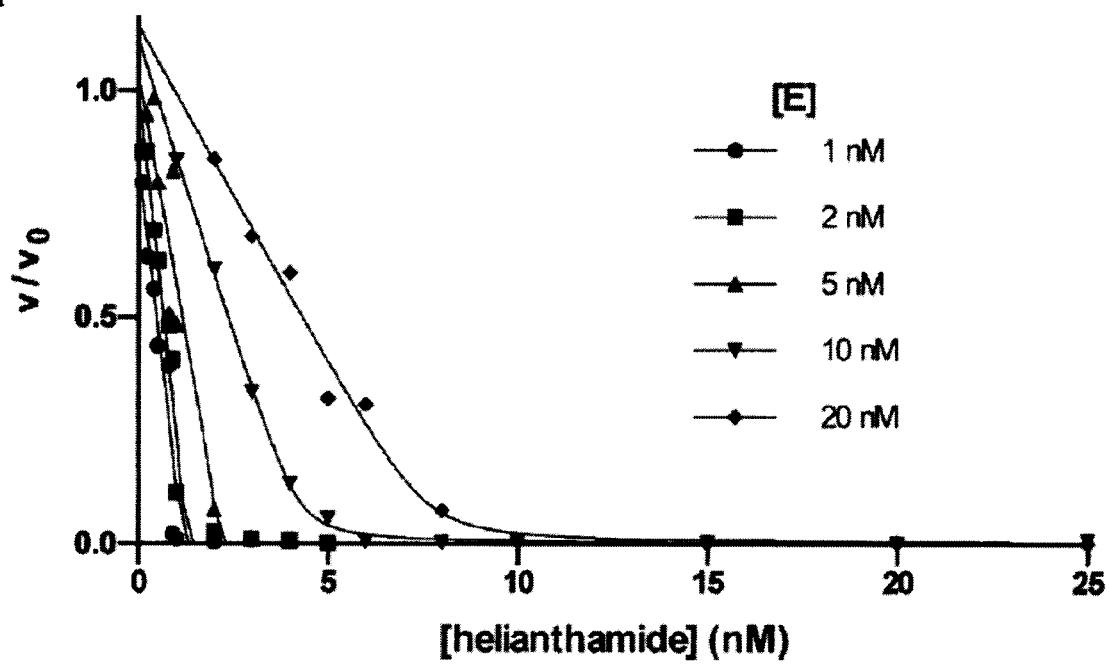
Figure 2:
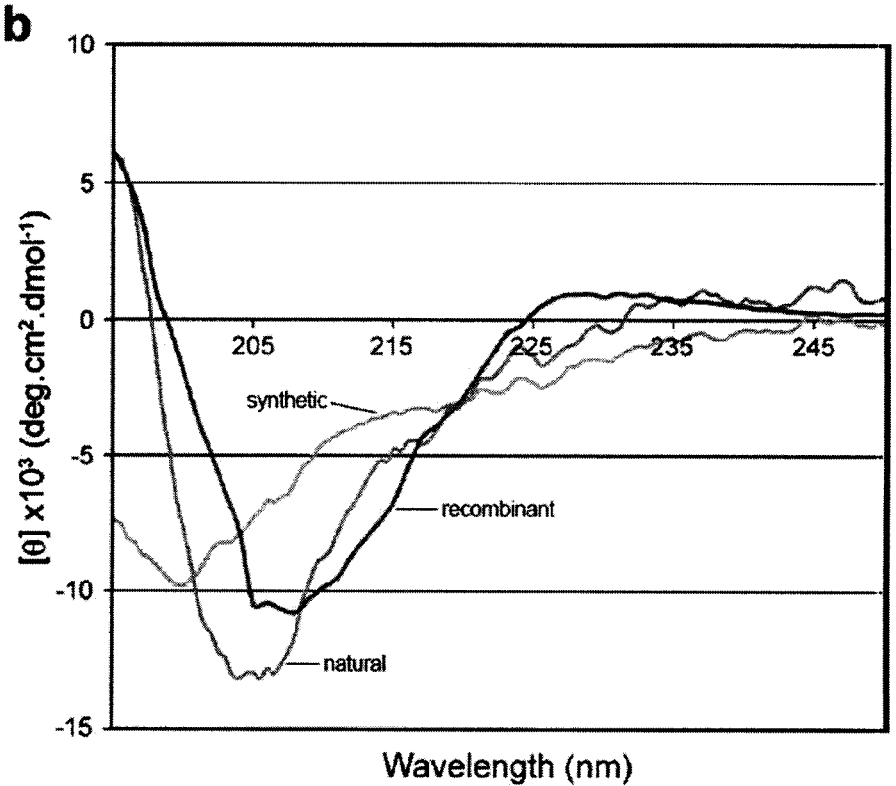

FIG. 2a shows kinetic analysis of recombinant Helianthamide versus HPA. Dose response curves of $v/v_o$ (observed rate over uninhibited rate) versus [helianthamide] were constructed for various enzyme concentrations at [CNP-G3]=5 mM. The curves were fit to the Morrison equation of tight-binding inhibition (equation 1) via a least mean squares method to give values for $K_{i\text{-}app}$ which were averaged and used to calculate $K_i$ by equation 2, which is the relationship between these two values for competitive inhibitors.

FIG. 2b shows CD spectrophotometric analysis of natural and synthetic and recombinant Helianthamide, wherein characterization was by circular dichroism spectroscopy and the remaining material was used for preliminary inhibitory studies, in which reversible inhibition of HPA was observed with a low nano-molar inhibition constant.

Figure 3:
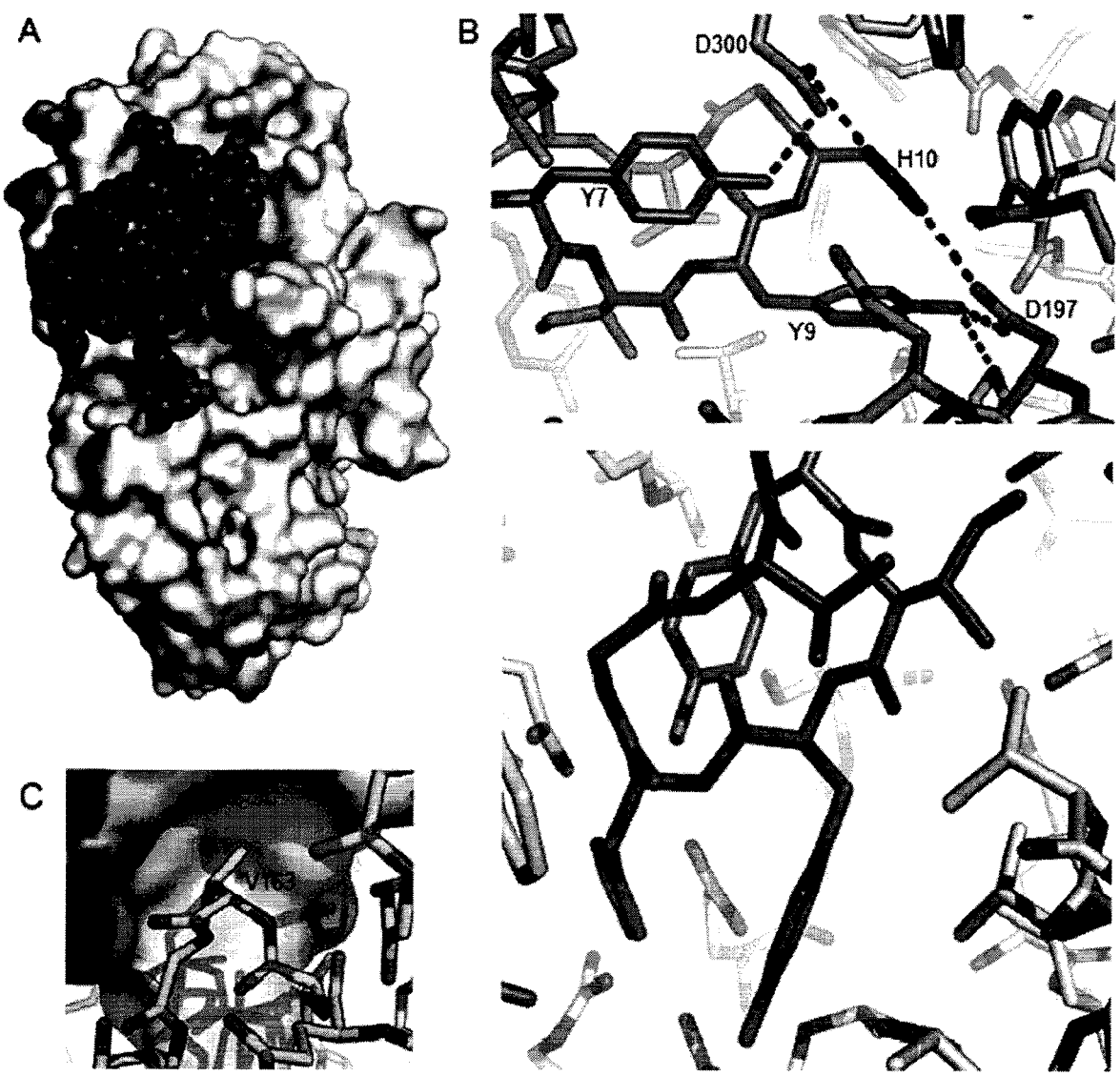

FIG. 3 shows crystal structure of Helianthamide and PPA. (A) Helianthamide (dark grey spheres) is observed within the active site cleft of PPA. (B) A closer examination of the amylase active site (light grey) reveals three residues of Helianthamide, Y7, Y9, and H10, interacting with the catalytic residues of PPA. I8 and V12 interact with the hydrophobic ridges surrounding the amylase active site. (C) Hydrophobic interactions play a large part in Helianthamide binding. A large hydrophobic pocket of Helianthamide (amorphous shape) is observed around V163 of PPA (branched cylinders) adjacent to the enzyme active site.

Figure 4:
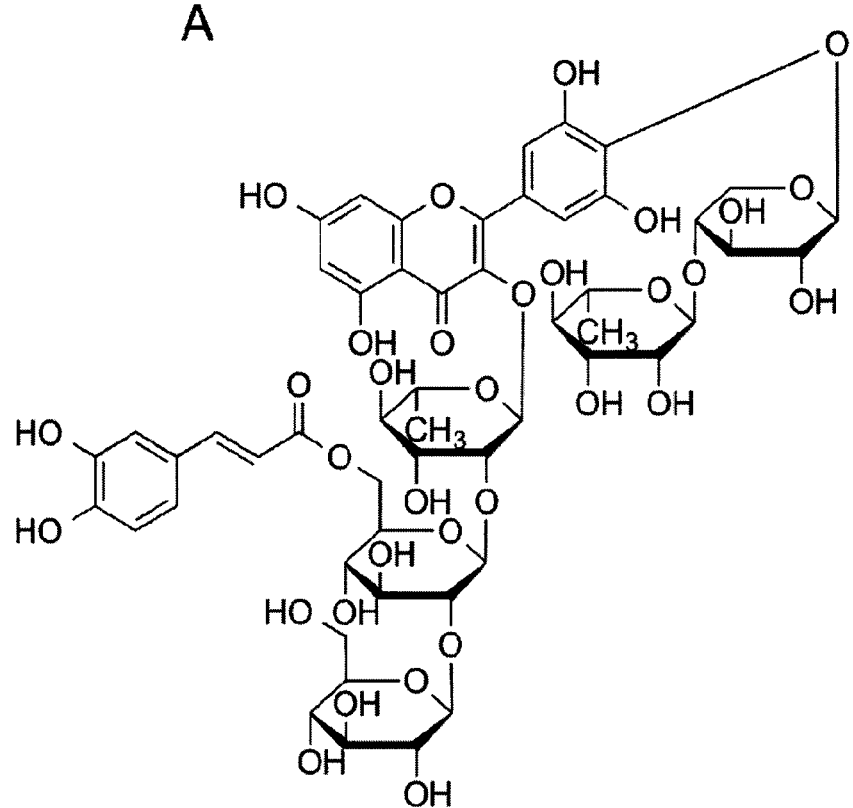
Figure 4:
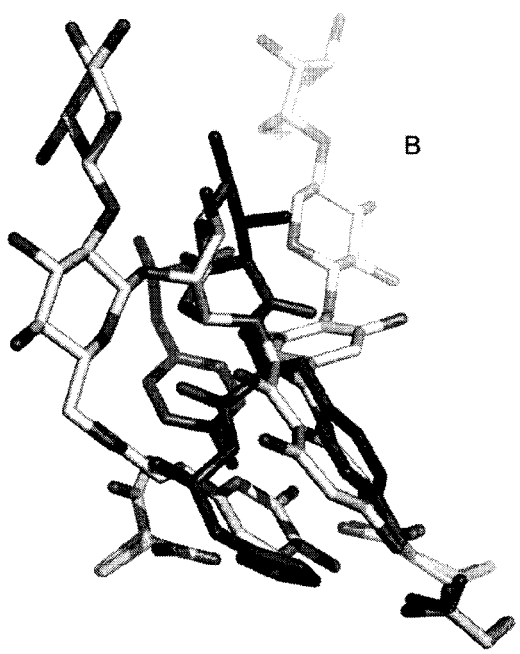

FIG. 4 shows a comparison of Helianthamide and Montbretin A as HPA inhibitors (A) Structure of Montbretin A (B) Overlay of Helianthamide's inhibitory motif with Montbretin A (PDB: 4W93).

Figure 5:
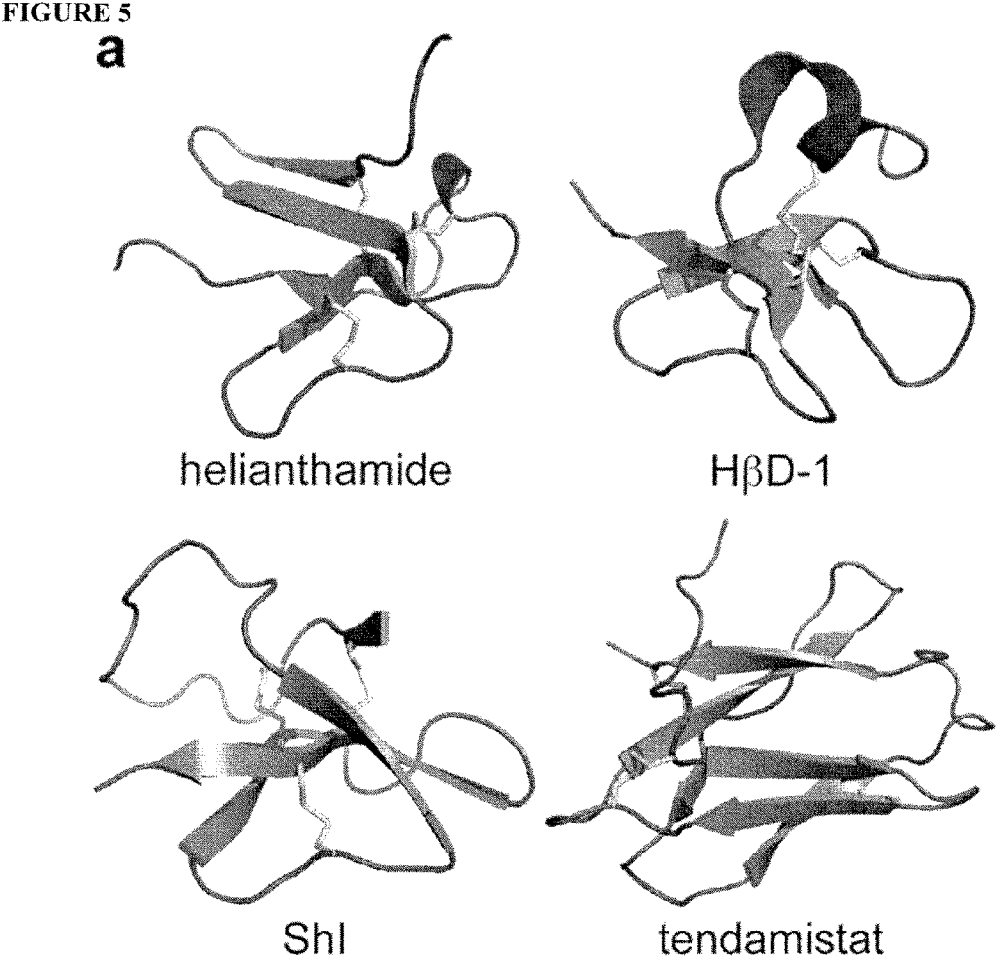

FIG. 5 shows structural and sequence comparisons of Helianthamide with other peptides, wherein (A) shows structural comparison of Helianthamide to the human β-defensins (hβD-1 and hβD-3 as representative examples), ShI, and tendamistat, with the β-sheets depicted as flat arrows, the helices as a ribbon (no arrow in Helianthamide and hβD-1 only), the loops as dark cylinders, and the disulfide bonds in as light cylinders. (B) shows a sequence alignment of Helianthamide with two 1-defensins, and comparisons to ShI, and representatives from the α-defensin and knottin families, wherein disulfide bonds are joined to bonding partners by lines.

Figure 6:
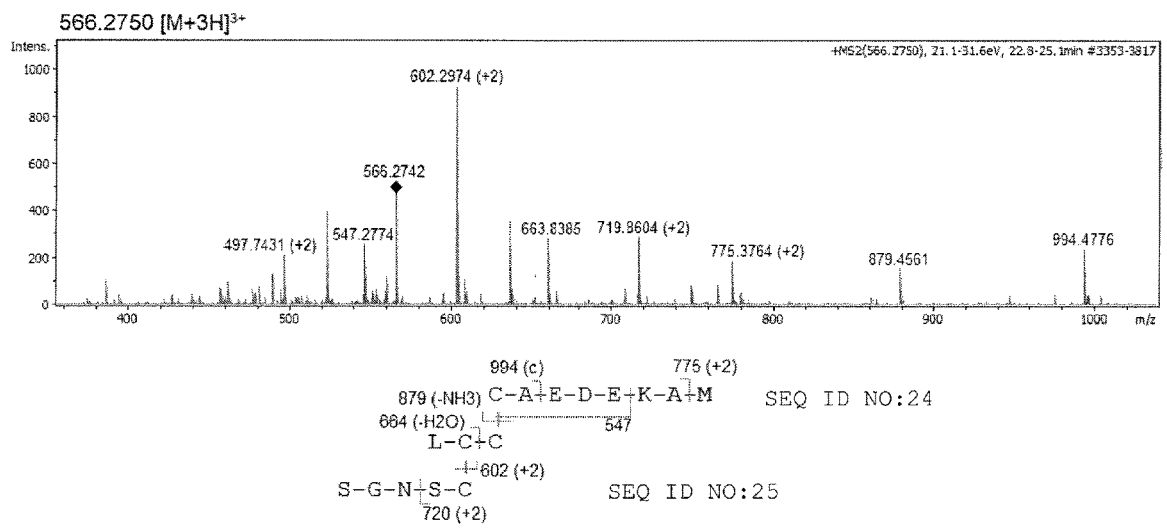
Figure 6:
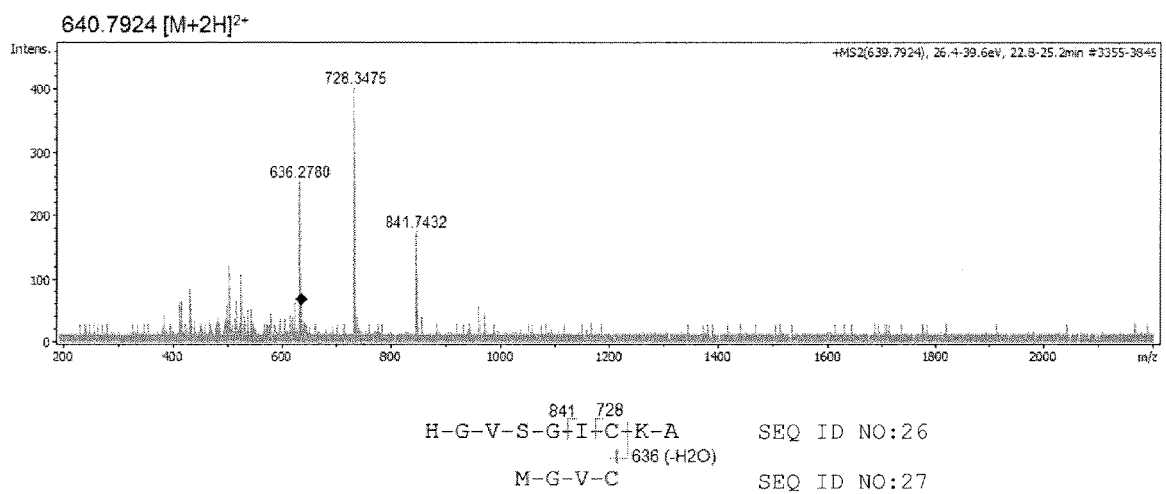

FIGS. 6A & B show MS/MS data of select peaks and their corresponding sequences for disulfide analysis of helianthamide. The data confirm the 1-5, 2-4, 3-6 connectivity seen in the crystal structure.

DETAILED DESCRIPTION

Any terms directly defined herein shall be understood to have the meanings commonly associated with them as understood within the art of the invention.

The term "enzyme" is used herein as it is normally understood to a person of ordinary skill in the art and often refers to a macromolecular biological catalyst that accelerates or catalyzes a chemical reaction. Most enzymes are usually a protein, but may also be a catalytic RNA molecule. Generally, an enzyme is a globular protein that has both a binding and a catalytic site, whereby the binding site holds and orients a substrate while the catalytic site reduces the chemical activation energy for the chemical reaction. In some cases, the enzyme itself does not interact with the substrate, but binds and orient catalytic cofactors that catalyze the reaction.

The term "glucosidases" is used herein as it is normally understood to a person of ordinary skill in the art and often refers to enzymes that hydrolyze glycosides.

The term "α-glucosidase" is used herein as it is normally understood to a person of ordinary skill in the art and often refers to an enzyme located in the brush border of the small intestine tract that acts upon 1,4-α-glycosidic bonds. Typically, an α-glucosidase, refers to a group of enzymes whose specificity is directed mainly toward the exohydrolysis of 1,4-alpha-glucosidic linkages, to hydrolyze oligosaccharides rapidly, relative to polysaccharides, which are hydrolyzed relatively slowly, or not at all. Other terms to define α-glucosidase can include, but are not limited to, glucosidase, EC 3.2.1.20, maltase, glucoinvertase, glucosidosucrase, maltase-glucoamylase, α-glucopyranosidase, glucosidoinvertase, α-D-glucosidase, α-glucoside hydrolase, α-1,4-glucosidase, or α-D-glucoside glucohydrolase.

The term "α-amylase" is used herein as it is normally understood to a person of ordinary skill in the art and often refers to a protein enzyme EC 3.2.1.1 that hydrolyses α-bonds of large, α-linked polysaccharides, wherein polysaccharides may include but are not limited to starch or glycogen and their respective enzymatic products glucose or maltose. The α-amylase enzyme is the major amylase found in the pancreatic juice or saliva of mammals.

The term "*Stichodactyla* sp." as used herein refers to a white carpet anemone living singularly on or about reefs or soft sand bottoms in the Caribbean, Indo-Pacific and the Red Sea.

The term "*Stichodactyla helianthus*" as used herein refers to an anemone of the family Stichodactylidae.

The term "bacterial host cell" as used herein refers to a bacterial cell that has been introduced with DNA, wherein the DNA may be foreign.

The term "tobacco etch virus protease" as used herein refers to a 27 kDa catalytic domain of the nuclear infusion a (NIa) protein encoded by the tobacco etch virus.

The term "tobacco etch virus" as used herein refers to a "TEV" or "a plant pathogenic virus in the genus Potyvirus and the virus family Potyviridae.

The term "*Escherichia coli*" as used herein refers to a Gram-negative, facultatively anaerobic, rod-shaped bacterium of the genus *Escherichia* that is commonly found in the lower intestine of mammals.

The term "*Pichia*" as used herein refers to a genus of yeast in the family of Saccharomycetaceae. Wherein "*Pichia pastoris*" is one member of this genus.

The term "expression vector" is used herein as it is normally understood to a person of ordinary skill in the art and often refers to an expression construct or a plasmid or virus containing the required regulatory sequence used for expression of a gene into a protein within a target cell, such as but not limited to bacterial, yeast, baculovirus, and mammalian cells as well as cell-free systems such as cell lysate or wheat-germ.

The term "barnase" as used herein refers to "bacterial ribonuclease" or "EC 3.1.27".

The term "SUMO" as used herein refers to "small uniquitin-like modifier".

The term "physiologically effective" is used herein as it is normally understood to a person of ordinary skill in the art and often refers to "having an impact on a living organism".

The term "oral administration" is used herein as it is normally understood to a person of ordinary skill in the art and often refers to intake through the mouth. Examples of oral administration include various forms, such as but not limited to, liquids such as syrups or mouth rinses, solids such as tablets or powders, pills or capsules, suspensions or gels, herbal formulations, teas, tinctures, vinegar tinctures, oil tinctures, oral topical preparations including salves, candy, chewing gum, additives to drinking water, tooth paste, or any other composition intended to be applied to the oral cavity or teeth.

The term "insulin resistance" is used herein as it is normally understood to a person of ordinary skill in the art and often refers to syndrome X or the diminished activity of a cell to respond to the action of the hormone insulin in transporting glucose from the bloodstream into muscle and other tissue. Often women with insulin resistance have a greater risk of many disorders, including diabetes, hypertension, heart disease, obesity, high cholesterol, breast cancer, and polycystic ovarian syndrome.

The term "postprandial glycemia" is used herein as it is normally understood to a person of ordinary skill in the art and refers to recurrent episodes of symptomatic hypoglycemia occurring within four hours after a high carbohydrate meal (or other glucose load) in a subject who has diabetes, also often referred to as "reactive glycemia".

The term "diabetes" is used herein as it is normally understood to a person of ordinary skill in the art and refers to "diabetes mellitus", a metabolic medical condition in which blood sugar levels are highly elevated over a prolonged time period leading to cardiovascular disease, stroke, chronic kidney failure, foot ulcers, and/or damage to the eyes. Most diabetes can be attributed to one of two types, insulin-dependent (IDDM or Type I) and non-insulin-dependent (NIDD or Type II).

The term "diabetic" is used herein as it is normally understood to a person of ordinary skill in the art and often refers to a subject having diabetes.

The term "pre-diabetic" is used herein as it is normally understood to a person of ordinary skill in the art and refers to a medical condition in which blood sugar levels are elevated, but not high enough to be classified as full-blown diabetes".

The term "obesity" is used herein as it is normally understood to a person of ordinary skill in the art and often refers to a medical condition in which excess body fat has accumulated to the extent that it may have a negative effect on health, leading to reduced life expectancy and/or increased health problems, wherein often a person with a body mass index of 30 $kg^2/m^2$ is considered obese.

The term "body mass index" is used herein as it is normally understood to a person of ordinary skill in the art and often refers to the product of the mathematical calculation of the square of the person's body weight divided by the square of the person's height.

The term "obese" is used herein as it is normally understood to a person of ordinary skill in the art and often refers to a subject with the medical condition obesity.

The term "polycystic ovary syndrome" or "PCOS" is used herein as it is normally understood to a person of ordinary skill in the art and refers to an endocrine system disorder among women of reproductive age.

The term "Non-alcoholic fatty liver disease" or "NAFLD" is used herein as it is normally understood to a person of ordinary skill in the art and refers to the accumulation of fat in the liver in non-alcoholic patients or steatosis.

The term "Middleton syndrome" is used herein as it is normally understood to a person of ordinary skill in the art and refers to primary accelerated gastric emptying in patients with normal gastric anatomy.

The term "motility" is used herein as it is normally understood to a person of ordinary skill in the art and refers to the contraction of the muscles that mix and propel contents in the gastrointestinal tract. The gastrointestinal tract is divided into four distinct parts that are separated by sphincter muscles. These four regions have distinctly different functions to perform and different patterns of motility: (1) esophagus, (2) stomach, (3) small intestine and (4) large intestine or colon. The term motility disorder of the gastrointestinal tract is used herein as it is normally understood to a person of ordinary skill in the art and often refers to abnormal motility or sensitivity in any part of the gastrointestinal tract (40), such as e.g. gastroesophageal reflux disease.

The term "gastric bypass" as used herein refers to a surgical procedure in which the stomach is divided into a small upper pouch and a larger lower remnant pouch, wherein the small intestine is rearranged to connect to both.

The term "gastrectomy" as used herein refers to the surgical removal of a part of the stomach (partial gastrectomy) or the whole stomach (total gastrectomy). Depending on the part of the stomach removed, the intestine may need to be re-connected to the remaining stomach (in case of a partial gastrectomy) or to the esophagus (in case of the total gastrectomy). Reasons for a gastrectomy may be morbid obesity or malignancy.

The term "postprandial reactive hypoglycemia" as used herein refers to the deficiency of glucose in the bloodstream within four hours or less after eating a meal.

The term "postprandial syndrome" or "Idiopathic postprandial syndrome" as used herein refers to recurrent episodes of altered mood and cognitive efficiency, often accompanied by weakness and adrenergic symptoms such as shakiness. The episodes typically occur a few hours after a meal, rather than after many hours of fasting. The principal treatments recommended are extra small meals or snacks and avoidance of excessive simple sugars.

The term "irritable bowel syndrome" or "IBS" as used herein refers to a disorder that affects the large intestine (colon) commonly causing cramping, abdominal pain, bloating, gas, diarrhea and constipation.

The term "dumping syndrome" as used herein refers to the medical condition, in which the contents of the stomach empty too quickly into the small intestine. The precipitous emptying of hyper-osmolar, carbohydrate-containing solutions from the stomach into the upper small bowel causes a rapid fluid shift into the lumen of the small bowel resulting in hypovolaemia, rapid glucose absorption, hyperglycaemia and reactive hypoglycaemia often resulting in nausea, cramping, diarrhea, sweating, faintness or palpitations. In the infant age group, the "infant dumping syndrome" is a severe complication which has proven difficult to treat. As used herein, "infant" refers to young children between birth and 2 years of age.

The term "antiviral" as used herein refers to a substance for the treatment of viral infections. Wherein the viral infection may be, for example, human immunodeficiency virus (HIV) or hepatitis B (HBV).

The term "pharmaceutical composition" as used herein refers to the preparation of a therapeutic agent for use on or in the body to prevent, diagnose, mitigate, alleviate, treat, or cure disease in animals or humans.

The term "crude" as used herein refers to a natural or raw state, not yet processed or refined.

The term "substantially purified" as used herein with regards to the peptides is meant to encompass a naturally occurring peptide that is present in any form that is at a level of purity greater than that of said in a naturally occurring product peptide on a per weight basis, wherein the naturally occurring product may be the tissue of an organism in nature and "naturally occurring product" is not meant to include peptides obtained from the cells of an expression system engineered to produce the peptide. Substantially purified may mean a peptide that is 100% pure, 99% pure, 98% pure, 97% pure, 96% pure, 95% pure, 94% pure, 93% pure, 92% pure, 91% pure, 90% pure, 85% pure, 80% pure, 75% pure, 70% pure, 65% pure, 60% pure, 55% pure, 50% pure, 45% pure, 40% pure, 35% pure, 30% pure, 25% pure, 20% pure, 15% pure or 10% pure, when measured on a per weight basis with any biological material that is not the peptide of interest.

The term "helianthamide" is used herein as it is normally understood to a person of ordinary skill in the art and often refers to a substantially purified peptide having the amino acid sequence $H_2N$-ESGNSCYIYHGSGICKASCAE-DEKAMAGMGVCEGHLCCYKTPW-COOH (SEQ ID NO:1).

Helianthamide as isolated from the Caribbean sea anemone *Stichodactyla helianthus*, is a highly potent and specific HPA inhibitor ($K_i$=10 pM) and a homologue to β-defensins. Soluble helianthamide may be produced through recombinant expression in *Escherichia coli* via a barnase-based fusion system, which offers benefits over the more commonly used SUMO-based fusions for the expression of disulfide rich peptides (4). This structure represents a novel class of glycosidase inhibitor and provides a new example for the β-defensin fold, ordinarily an antimicrobial agent (5). Helianthamide represents a new class of α-amylase inhibitor due to both its structural homology to the β-defensins and its active YIYH (SEQ ID NO: 28) inhibitory motif. This peptide exhibits amylase inhibitory potency at the highest level observed in nature, and is specific for mammalian α-amylase over other glycosidases. Helianthamide demonstrates impressive stability due to its tightly knotted disulfide-rich core, which makes it stable against hydrolases in the digestive system (38). The inherently low bioavailability of large disulfide linked peptides minimizes unwanted side effects associated with systemic absorption, such as abdominal bloating, gas, and diarrhea. In addition, its high stability permits tolerance to oral consumption, one of the most convenient ways of drug administration. The high stability and inhibitory specificity of helianthamide make it a good candidate therapeutic agent for the control of blood glucose levels in diabetic patients, as it should exhibit reduced side effects compared to other known α-glycosidase inhibitors. Helianthamide adopts a β-defensin type fold with three disulfide bonds and binds into and across the HPA active site with tyrosine and histidine residues interacting with HPA catalytic residues. Its inhibition constant of 10 pM places helianthamide among the most potent amylase inhibitors known.

Although one aspect of the present invention is the specificity with which helianthamide inhibits HPA, human α-glucosidases in general and especially hyperactive α-glucosidase have been associated with a variety of medical conditions (42). Inhibitors of α-glucosidases, such as acarbose, have been used for the treatment of gastrointestinal mobility such as disorders of the small intestine, large intestine, rectum and pelvic floor (40), infant dumping syndrome (43), late dumping syndrome (44), postprandial hypoglycemia e.g. after Nissen fundoplication (45) or in patients with Middleton syndrome (46). Beyond their effect on the gastrointestinal system, anti-hyperglycaemic agents have been shown to restore ovarian function in polycystic ovary syndrome (PCOS) (27), to reduce fatty liver (48, 49), to treat non-insulin-dependent (type 2) diabetes mellitus (50), and to lower microvascular and macrovascular complications associated with type 2 diabetes (51), such as proliferate tissue abnormalities and cancer (52). Because the outer envelope of many animal viruses comprises viral glycoproteins, which are often required for the viral life cycle and utilize cellular machinery for synthesis, α-glucosidase inhibitors can prevent fusion of HIV and secretion of hepatitis B virus (HBV) (53, 54 and 55). In another aspect of this invention helianthamide may be an inhibitor of α-glucosidases and especially hyperactive human α-glucosidase.

These and other features, aspects, and advantages of the present invention will become better understood with reference to the following description and accompanying drawings here.

"Delivery," as used herein, refers to delivery of a mammalian alpha-amylase inhibitor directly to a target site within an organism. For example, a mammalian alpha-amylase inhibitor may be delivered orally such that the inhibitor stays within the gastrointestinal tract. In particular, alpha-amylase is active in the lumen of the duodenum and thus delivery to the lumen of the duodenum may be advantageous.

As used herein, an "inhibitor" refers to an agent that restrains, retards, or otherwise causes inhibition of a physiological, chemical or enzymatic action or function. An inhibitor may cause at least 5% decrease in enzyme activity. An inhibitor may also refer to a drug, compound or agent that prevents or reduces the expression, transcription or translation of a gene or protein. An inhibitor may reduce or prevent the function of a protein, for instance by binding to and/or activating/inactivating another protein or receptor. An inhibitor may reduce or prevent the interaction of an enzyme or protein with another enzyme or protein. An inhibitor may cause degradation or clearance of a protein from a cell or from the body of a subject. For instance, an inhibitor may bind to the protein and such binding may target the protein for cellular degradation or for clearance from the body. Such inhibitors could be any polypeptide or peptide or fragment thereof as described herein. Binding of an inhibitor to the mammalian alpha-amylase protein in view may prevent it from binding its cognate receptor, could prevent other important molecular interactions, or could alter the conformation of the protein. Binding of an inhibitor to the mammalian alpha-amylase may also prevent interaction of the enzyme with starch, and would thus also inhibit the hydrolysis of starch to oligosaccharides. All such embodiments are considered within the definition of an inhibitor and are considered to be within the scope of the present invention.

The term "alpha-amylase inhibitor" or "α-amylase inhibitor" refers to any molecule that inhibit the alpha-amylase enzyme, either directly or indirectly, for example by interfering with the mammalian alpha-amylase activity, up regulating endogenous inhibitors and/or shutting down transcription of the mammalian alpha-amylase gene or translation of the mammalian alpha-amylase transcript. The term "mammalian alpha-amylase inhibitor" is used herein as it is normally understood to a person of ordinary skill in the art and often refers to any molecule that reduces or diminishes the activity of a mammalian α-amylase. In particular, as set out herein, the mammalian alpha-amylase inhibitor binds to the alpha-amylase active site (i.e. catalytic and/or binding domains).

As used herein a "subject" refers to an animal, such as a bird or a mammal. Specific animals include rat, mouse, dog, cat, cow, sheep, horse, pig or primate. A subject may further be a human, alternatively referred to as a patient. A subject may further be a transgenic animal. A subject may further be a rodent, such as a mouse or a rat.

The terms "peptide" and "polypeptide" may be used interchangeably, and as used herein refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

Examples of modifications to peptides may include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties*, $2^{nd}$ ed., T. E. Creighton, W. H. Freeman and Company, New York, 1993 and Wold F, *Posttranslational Protein Modifications: Perspectives and Prospects*, pgs. 1-12 in *Posttranslational Covalent Modification of Proteins*, B. C. Johnson, ed., Academic Press, New York, 1983; Sezfter et al., *Analysis for protein modifications and nonprotein cofactors, Meth. Enzymol.* (1990) 182: 626-646 and Rattan et al. (1992), *Protein Synthesis: Posttranslational Modifications and Aging,"* Ann NY Acad Sci 663: 48-62.

A "substantially similar sequence" refers to an amino acid sequence that differs from a reference sequence only by one or more substitutions, but which may, for example, be functionally homologous to another substantially similar sequence. It will be appreciated by a person of skill in the art the aspects of the individual amino acids in a peptide of the invention that may be substituted. In particular, the substitutions may take the form of one or more of the consensus amino acid sequences setout herein (for example, SEQ ID NOs: 3, 7 and 9-15). Alternatively, a peptide may be at least 20% identical to the helianthamide amino acid sequence. Alternatively, a peptide may be at least 30% identical to the helianthamide amino acid sequence. Alternatively, a peptide may be at least 40% identical to the helianthamide amino acid sequence. Alternatively, a peptide may be at least 50% identical to the helianthamide amino acid sequence. Alternatively, a peptide may be at least 60% identical to the helianthamide amino acid sequence. Alternatively, a peptide may be at least 70% identical to the helianthamide amino acid sequence. Alternatively, a peptide may be at least 80% identical to the helianthamide amino acid sequence. Alternatively, a peptide may be at least 85% identical to the helianthamide amino acid sequence. Alternatively, a peptide may be at least 90% identical to the helianthamide amino acid sequence. Alternatively, a peptide may be at least 91% identical to the helianthamide amino acid sequence. Alternatively, a peptide may be at least 92% identical to the helianthamide amino acid sequence. Alternatively, a peptide may be at least 93% identical to the helianthamide amino acid sequence. Alternatively, a peptide may be at least 94% identical to the helianthamide amino acid sequence. Alternatively, a peptide may be at least 95% identical to the helianthamide amino acid sequence.

The helianthamide amino acid sequence may be

```
                                            (SEQ ID NO: 1)
ESGNSCYIYHGVSGICKASCAEDEKAMAGMGVCEGHLCCYKTPW.
```

Functionally, the "substantially similar sequence" should still act as an inhibitor or mammalian alpha-amylase.

Amino acid sequence similarity or identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, *J Mol. Biol.* 215: 403-410 and ALTSCHUL et al. (1997), *Nucleic Acids Res.* 25: 3389-3402.

Amino acids may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide.

Nomenclature used to describe the peptide compounds of the present invention follows the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the trivial name of the amino acid, in accordance with TABLE 1.

TABLE 1

Nomenclature and abbreviations of the 20 standard L-amino acids commonly found in naturally occurring peptides.

| Full name | Three-letter abbreviation | One-letter abbreviation |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

The hydropathy index of an amino acid is a scale indicating the tendency of an amino acid to seek out an aqueous environment (negative value) or a hydrophobic environment (positive value) (KYTE & DOOLITTLE 1982. *J Mol Biol* 157:105-132). Hydropathy indices of the standard amino acids include alanine (1.8), arginine (−4.5), asparagine (−3.5), aspartic acid (−3.5), cysteine (2.5), glutamine (−3.5), glutamic acid (−3.5), glycine (−0.4), histidine (−3.2), isoleucine (4.5), leucine (3.8), lysine (−3.9), methionine (1.9), phenylalanine (2.8), proline (−1.6), serine (−0.8), threonine (−0.7), tryptophan (−0.9), tyrosine (−1.3), and valine (4.2). Amino acids with similar hydropathy indices may be substitutable for each other in a peptide.

In order to further exemplify what is meant by a conservative amino acid substitution, the examples set out in Groups A-F are listed below. The replacement of one member of the following groups by another member of the same group is considered to be a conservative substitution, whereby the characteristics of the overall polypeptide and the substituted amino acid are conserved follow the substitution.

Group A includes leucine, isoleucine, valine, methionine, phenylalanine, serine, cysteine, threonine, and modified amino acids having the following side chains: ethyl, iso-butyl, —CH$_2$CH$_2$OH, —CH$_2$CH$_2$CH$_2$OH, —CH$_2$CHOHCH$_3$ and CH$_2$SCH$_3$.

Group B includes glycine, alanine, valine, serine, cysteine, threonine, and a modified amino acid having an ethyl side chain.

Group C includes phenylalanine, phenylglycine, tyrosine, tryptophan, cyclohexylmethyl, and modified amino residues having substituted benzyl or phenyl side chains.

Group D includes glutamic acid, aspartic acid, a substituted or unsubstituted aliphatic, aromatic or benzylic ester of glutamic or aspartic acid (e.g., methyl, ethyl, n-propyl, iso-propyl, cyclohexyl, benzyl, or substituted benzyl), glutamine, asparagine, CO—NH-alkylated glutamine or asparagine (e.g., methyl, ethyl, n-propyl, and iso-propyl), and modified amino acids having the side chain —(CH$_2$)$_3$COOH, an ester thereof (substituted or unsubstituted aliphatic, aromatic, or benzylic ester), an amide thereof, and a substituted or unsubstituted N-alkylated amide thereof.

Group E includes histidine, lysine, arginine, N-nitroarginine, p-cycloarginine, g-hydroxyarginine, N-amidinocitruline, 2-amino guanidinobutanoic acid, homologs of lysine, homologs of arginine, and ornithine.

Group F includes serine, threonine, cysteine, and modified amino acids having Cl-C5 straight or branched alkyl side chains substituted with —OH or —SH.

Groups A-F are exemplary and are not intended to limit the invention.

Peptides or peptide analogues can be synthesised by chemical techniques known in the art, for example, by automated synthesis using solution or solid phase synthesis methodology. Automated peptide synthesisers are commercially available and use techniques well known in the art. Peptides and peptide analogues can also be prepared using recombinant DNA technology using methods such as those described in, for example, SAMBROOK J. AND RUSSELL D. (2000) Molecular Cloning: A Laboratory Manual (Third Edition) Cold Spring Harbor Laboratory, Cold Spring Harbor Laboratory Press, Cold Spring Harbor, N.Y.) or AUSUBEL et al. (Current Protocols in Molecular Biology, John Wiley & Sons, 1994).

A "peptidomimetic" is a compound comprising non-peptidic structural elements that mimics the biological action of a parent peptide. A peptidomimetic may not have classical peptide characteristics such as an enzymatically scissile peptidic bond. A parent peptide may initially be identified as a binding sequence or phosphorylation site on a protein of interest, or may be a naturally occurring peptide, for example a peptide hormone. Assays to identify peptidomimetics may include a parent peptide as a positive control for comparison purposes, when screening a library, such as a peptidomimetic library. A peptidomimetic library is a library of compounds that may have biological activity similar to that of a parent peptide.

Amino acids contained within the peptides described herein are generally understood to be in the L-configuration. However, peptides and peptidomimetics of the present invention, D-amino acids may be substitutable for L-amino acids in some circumstances. Amino acids contained within the peptides of the present invention, and particularly at the carboxy- or amino-terminus, may be modified by methylation, amidation, acetylation or substitution with other chemical groups which may change the circulating half-life of the peptide without adversely affecting their biological activity. Additionally, a disulfide linkage may be present or absent in the peptides of the invention and it is possible that the disulfide bridges may form after administration. Another approach for modification of an existing sequence is to synthesize the corresponding retro-inverso version. A retro-inverso peptide is one in which the sequence is reversed ie. reversal of the N to C terminal and synthesized using D-amino acids. Retro inverso analogs of L peptides when aligned alongside each other from N to C and C to N have all side chains in the same orientation, however the peptide bonds are reversed and sterically unavailable for cleavage by proteases. Nair et. al. 2003 *J. Immunol.* 170:1362-1373.

Based on the structure of the Helianthamide polypeptide and the particular interactions it is believed to have with mammalian alpha-amylases, various consensus sequences were developed particular features of the Helianthamide polypeptide and its predicted interactions with PPA based on the crystal structure thereof. In particular the various disulfide bridges that are formed; the hydrogen bonds formed with PPA; the interactions with catalytic residues of PPA; the interactions with hydrophobic ridges surrounding the amylase active site of PPA; and the lack of charged residues which are believed to distinguish the Helianthamide from the human beta-defensins. Accordingly, the consensus amino acid sequences setout herein and various preferred amino acid substitutions are set out in TABLE 2 below were determined.

TABLE 2

Amino Acids Substitutions.

| Original Amino Acid Residue | Exemplary Substitutions | Alternative Substitution |
|---|---|---|
| Alanine (A) | V, I or L | V |
| Aspartic acid (D) | E | E |
| Glutamic acid (E) | D | D |
| Phenylalanine (F) | L, V, I, A or Y | L |
| Glycine (G) | A | A |
| Histidine (H) | K or R | K or R |
| Isoleucine (I) | V, A or L | L |
| Lysine (K) | H or R | H or R |
| Leucine (L) | V, A or I | I |
| Methionine (M) | L, F or I | L |
| Asparagine (N) | Q | Q |
| Proline (P) | A or G | G |
| Arginine (R) | K or H | K or H |
| Serine (S) | T | T |
| Threonine (T) | S | S |
| Valine (V) | A, I or L | L |
| Tryptophan (W) | Y or F | Y |
| Tyrosine | S | S |

Note:
no substitution suggested for Cysteine (Cys); or Glutamine (Gln).

Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-imino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

The mammalian alpha-amylase inhibitors described herein may be in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term "medicament" as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term "pharmaceutically acceptable excipient" may include any and all solvents, dispersion media, coatings, antibacterial, antimicrobial or antifungal agents, isotonic and absorption delaying agents, and the like that are physiologically compatible. Furthermore, an excipient may include a "pharmaceutically acceptable carrier" as set out below. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

Mammalian alpha-amylase inhibitors described herein may be administered in any of a variety of known routes. Examples of methods that may be suitable for the administration of mammalian alpha-amylase inhibitors described herein include orally, intravenously, by inhalation, intramuscularly, subcutaneously, topically, intraperitoneally, intrarectally or intra-vaginally, sublingually, and the like. Mammalian alpha-amylase inhibitors described herein may be administered as a sterile aqueous solution, or may be administered in a fat-soluble excipient, or in another solution, suspension, patch, tablet or paste format as is appropriate. A composition comprising the mammalian alpha-amylase inhibitors described herein may be formulated for administration by inhalation. For instance, a mammalian alpha-amylase inhibitor described herein may be combined with an excipient to allow dispersion in an aerosol. Examples of inhalation formulations will be known to those skilled in the art. Other agents may be included in combination with the mammalian alpha-amylase inhibitors described herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of mammalian alpha-amylase inhibitors described herein may vary depending on the route of administration (oral, intravenous, inhalation, or the like) and the form in which the composition or compound is administered (solution, controlled release or the like). Determination of appropriate dosages is within the ability of one of skill in the art. As used herein, an "effective amount", a "therapeutically effective amount", or a "pharmacologically effective amount" of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the mammalian alpha-amylase inhibitors described herein to the target tissue or cell in which inhibition of mammalian alpha-amylase is desired. It is also understood that it may be desirable to target mammalian alpha-amylase inhibitors described herein to a desired tissue or cell type. The mammalian alpha-amylase inhibitors described herein of the invention may be coupled to a cell uptake moiety. The targeting moiety may also function as the cell uptake moiety.

Delivery of bioactive molecules such as peptides, to a cell or cells in a reasonably efficient manner may require more than just the 'dumping' of the naked peptide onto the cell, or administering the naked peptide into the patient or test subject. Agents that enable delivery of bioactive molecules into cells in a suitable manner so as to provide an effective amount are known as "pharmaceutically acceptable carriers", such as a pharmacologically effective amount are known in the art, and are described in, for example, DIETZ et al 2004. *Mol Cell. Neurosci* 27:85-131. Examples of such agents include liposomes, lipid particles, antibodies or receptor ligands that may be coupled to the bioactive molecule, viral vectors, and protein transduction domains (PTD). Examples of PTDs include Antennapedia homeodomain (PEREZ et al 1992 *J. Cell Sci* 102:717-722), transportan (POOGA et al 1998 *FASEB J* 12: 67-77), the translocation domains of diphtheria toxin (STENMARK et al 1991 *J Cell Biol* 113:1025-1032; WIEDLOCHA et al 1994 *Cell* 76:1039-1051), anthrax toxin (BALLARD et al 1998 *Infect. Immun* 66:615-619; BLANKE et al 1996 *Proc Natl Acad Sci* 93: 8437-8442) and *Pseudomonas* exotoxin A (PRIOR et al 1992 *Biochemistry* 31:3555-3559), protegrin derivatives such as dermaseptin S4 (HARITON-GAZAL et al 2002 *Biochemistry* 41:9208-9214), HSV-1 VP22 (DILBER et al 1999 *Gene Ther.* 6:12-21), PEP-1 (MORRIS et al 2000 *Nature Biotechnol* 19:1173-1176), basic peptides such as poly-L and poly-D-lysine (WOLFERT et al 1996 *Gene Ther.* 3:269-273; RYSER et al 1980 *Cancer* 45:1207-1211; SHEN et at 1978 *Proc Natl Acad Sci* 75:1872-1876), HSP70 (FUJIHARA et al 1999 *EMBO J* 18:411-419) and HIV-TAT (DEMARCHI et al 1996 *J Virol* 700:4427-4437). Other examples and related details of such protein transduction domains are described in DIETZ, supra and references therein.

Materials and Methods

The procedures described herein are given for the purposes of example and illustration only and should not be considered to limit the spirit or scope of the invention.

Collection and Extraction of Animal Material

*Stichodactyla helianthus* was collected by hand at a depth of 2-3 meters at Cape Capucin, Island of Dominica. Specimens were immediately frozen and transported to Vancouver, British Columbia. Prior to analysis, the *S. helianthus* were exhaustively extracted with MeOH (3×300 mL).

High-Throughput Screening

Screening was performed on a Beckman Coulter Biomek FX Laboratory Automation Workstation™ (Fullerton, Calif., USA) integrated with a Beckman Coulter DTX880™ plate reader with UV/Vis capability. The screening assay was run in 384-well plates containing a 60 µL volume of 50 mM sodium phosphate 100 mM sodium chloride buffer (pH 7.0), HPA (1 ug mL$^{-1}$), and the commercially available HPA substrate 2-chloro-4-nitrophenyl-α-maltotrioside (1 mM; $K_M$=3.6 mM). TritonX-100™ (0.01%) was included to minimize detection of non-specific inhibitors. The natural product extract samples were present as DMSO solutions that contained 5 mg mL$^{-1}$ of dried methanolic extract, which were tested at a dilution of 60 µL in a final assay volume of 60 µL. HPA was found to be unaffected by the addition of this small amount of DMSO (0.1%) and Triton X-100™ (0.01%). The integrity of the assay was tested through the use of two test plates run as the first and last plate of each batch and which contained a serial dilution of the known HPA inhibitor acarbose. Validation of hits from the primary screen were further tested manually on a UV/Vis spectrophotometer. Amongst the hits examined in this secondary screen, the natural extract from the sea anemone *Stichodactyla helianthus* proved to have the highest activity against HPA. A more detailed account of the screening methodology used can be found in Tarling et al. 2008 (33).

Activity Guided Peptide Isolation

The *S. helianthus* MeOH extract from a 154 g *S. helianthus* specimen was further separated on a HP-20™ column, which was eluted with 150 mL portions of 0%, 30%, 500%, 75%, and 100% Me$_2$CO in H$_2$O. Greatest activity was traced to the 30% Me$_2$CO/H$_2$O fraction (162 mg), which was then chromatographed on an LH-20 size exclusion column (28× 710 mm) eluting with 25% MeOH/75% H$_2$O/0.1% TFA. The material (13.1 mg) was then purified using RP-HPLC with a Ca column eluting with 23% MeCN/77% H$_2$O/0.1% TFA to yield the active peptide (2.0 mg).

Peptide Sequencing

Disulfide linkages were reduced with dithiothreitol (100 mM) for 1 hour at 56° C. after which the resulting free cysteines were alkylated with iodoacetamide (100 mM) for 1 hour at 25° C. in pH 7.5 ammonium bicarbonate buffer (50 mM). MALDI-TOF analysis indicated a change in mass of 350.4 after reduction and alkylation which corresponds to approximately six alkylated cysteines. It could be deduced that the native material possessed three disulfide bonds. Peptide digestions were carried out by incubating reduced and alkylated peptide with trypsin (Promega Gold™) in pH 8.5 Tris buffer (50 mM) for 18-24 hours at 37° C., or with Glu-C (V8 protease, Roche) in pH 8.5 sodium phosphate buffer (50 mM) for 18-24 hours.

De novo sequencing: Sequencing was performed by LC-MS/MS on an LC Packings™ capillary LC system (Dionex™) coupled to a QSTAR™ Pulsar quadrupole TOF mass spectrometer (Applied Biosystems™). MS data were acquired using Analyst QS™ software (Applied Biosystems™) for information-dependant acquisition. N$_2$ was used as collision gas and the ionization tip voltage was 2200 V.

Edman sequencing: Digested peptides were separated on a Vydac™ HPLC microbore C$_{18}$ column (ODS-300, 7 µm, 1×50 mm). The peptide fractions were loaded on a precycled glass fiber filter coated with Biobrene and sequenced by the Edman degradation liquid phase method using a Procise cLC-494™ (Applied Biosystems™) equipped with an on-line 140D Phenylthiohydantoin analyser (Applied Biosystems™). The phenylthiohydantoin amino acid (PTH-aa) derivatives were determined by comparison with standards analyzed at the start of the sequence analysis.

Expression of the Helianthamide in Bacteria

A synthetic gene of the desired construct was ordered as a pUC-57 plasmid from BioBasic™ Canada. The gene was ligated into a pET-29b+ vector and transformed into electrocompetent BL21* *E. coli*, which were screened on LB-Kan50 plates. Starter cultures were made by incubating colonies containing the desired plasmid in 5 mL of LB-Kan50 overnight at 37° C. Starter cultures were added to 500 mL of LBE-5052 autoinduction media. The expression cultures were incubated at 25° C. (230 RPM) for 24 hours. The resulting culture supernatant was treated with 60% ammonium sulfate. The $(NH_4)SO_4$ solution was stirred at 4° C. for one hour before centrifugation to isolate the precipitated proteins. The proteins were re-suspended in His-trap binding buffer (20 mM sodium phosphate, 500 mM NaCl, 5 mM imidazole, pH 8) and applied to a Ni-NTA agarose column. The protein of interest was eluted over a gradient of increasing imidazole. The crude fusion was then cleaved using 100 units of TurboTEV™ protease per milligram of fusion at 30° C. for 16 hours. Helianthamide was purified from the reaction mixture by treatment with 50% methanol, leading to precipitation of TEV protease, bar', and bar'-helianthamide. For production of the fusion mutants, site-directed mutagenesis was performed via the four-primer method. The mutated genes were ligated into pET-29b+ plasmids and transformed into BL21* E. coli. Expression conditions and purification occurred as the same as the wild-type fusion.

DTNB Assay

A solution of thiol titration buffer was prepared (0.2 mM 5,5'-dithiobis-(2-nitrobenzoic acid), 6 M guanidine HCl, 20 mM HEPES, imM EDTA, pH 7.4). Helianthamide was added to the solution in final protein concentrations ranging from 2-6 μM (18). The release of 2-nitro-5-thiobenzoate was monitored at 412 nm at 25° C. over the course of 30 minutes. During each measurement, $\Delta A_{412}$ was also measured for the thiol titration buffer to take into account the rate of spontaneous hydrolysis of the DTNB reagent. The experiment was also conducted with BSA, which has one free thiol group, as a positive control.

Disulfide Assignment of Recombinant Material

Intact helianthamide was incubated in 11 M HCl at 37° C. for 4 days. The sample was diluted and neutralized before desalting by C18 reverse phase chromatography. The peptide mixture was injected into an Agilent™ 6460 QQQ LC/MS mass spectrometer. Elution and MS/MS analysis was carried out over a 40-minute period. A script was written to predict all possible fragments for the helianthamide sequence in the event of random hydrolysis and was used to analyze the resulting MS and MS/MS peaks.

Expression of Human Pancreatic α-Amylase

A detailed protocol of this expression can be found in the work done by Rydberg et al. (39) Expression was carried out in *Pichia pastoris*. Colonies were grown in 600 mL BMGY media at 30° C. 200 RPM. 20 mL of the overnight culture was added to 600 mL BMGY. After 16 hours the cells were transferred to 300 mL BMMY. After one day 2 mL of 50% methanol was added. The culture was left overnight. The culture supernatant was collected and purified via Phenyl Sepharose™ and Hitrap Q™ columns. Deglycosylation was performed with EndoF™.

Kinetic Analysis of Recombinant Material

Assays were performed on a Varian Cary 300™ UV/Vis spectrophotometer. The release of 2-chloro-nitrophenol resulting from the amylase catalyzed hydrolysis of 2-chloro-p-nitrophenyl-α-D-maltotrioside was monitored at 400 nm. Reactions were run at 30° C. in 50 mM sodium phosphate, 100 mM sodium chloride (pH 7.0). Reactions were monitored over 5 minutes to measure the initial reaction rate. For $K_i$ values less than 50 nM, inhibition constants were calculated using the Morrison equation for tight-binding inhibition. Reactions were run with a final [CNPG3]=5 mM. Typically, six different inhibitor concentrations were used for each enzyme concentration. Up to 5 different enzyme concentrations were used, ranging from 1 nM to 10 nM. $v/v_o$ was plotted against [I] for each enzyme concentration to form a series of dose response curves. These data sets were then fitted to the Morrison equation using a least mean squares method to determine a value of $K_{iapp}$ for each enzyme concentration. $K_{iapp}$ was then used to calculate $K_i$. $K_i$ values greater than 50 nM were determined by Michaelis-Menten inhibition kinetics. Details of this process can be found in the work done by Tarling et al. (33). After kinetic analysis with HPA, nine additional enzymes were tested against helianthamide. Concentrations of up to 1 μM of Helianthamide were used to assess for inhibition.

Crystallization of Synthetic Helianthamide/PPA Complex

Synthetic peptide was purchased from AnaSpec Inc.™ Porcine pancreatic α-amylase (PPA) was purchased from Sigma™ (A4268). The crystallization conditions used were based on the Hampton Research Crystal Screen™ kit. Diffraction quality crystals of PPA-helianthamide were grown by combining PPA and helianthamide in a 1:2.5 enzyme:inhibitor molar ratio. 2 μL of the enzyme inhibitor solution was mixed with 2 μL of 100 mM Tris, pH 8.5, 8% PEG-8000 (mother liquor) on siliconized microscrope slides. The slides were inverted and sealed over wells containing 500 μL of mother liquor. The crystals grew at room temperature in approximately three weeks' time. The crystals were soaked in mother liquor with 30% glycerol before flash freezing in liquid nitrogen and sent to Stanford Synchrotron Radiation Lightsource™ for remote data collection.

X-Ray Crystallographic Data Collection, Processing and Refinement

Data was collected using a MarMosaic 325 CCD™ detector on beamline 9-2 at the SSRL using a wavelength of 0.9794 Å and a 1° oscillation. The resulting data was processed using Mosflm™ and was scaled, merged and truncated using Scala™. Molecular replacement was performed using CNS. The coordinates of PPA [PDB ID: 1PIF] were used for the model from which the initial phases were derived. The coordinates for Helianthamide were built in manually into the empty density of the amylase active site using Coot based on the sequence of the peptide.

EXAMPLES

Various alternative embodiments and examples are described herein. These embodiments and examples are illustrative and should not be construed as limiting the scope of the invention.

Example 1: Screening Hit for *Stichodactyla helianthus*

Figure 1:
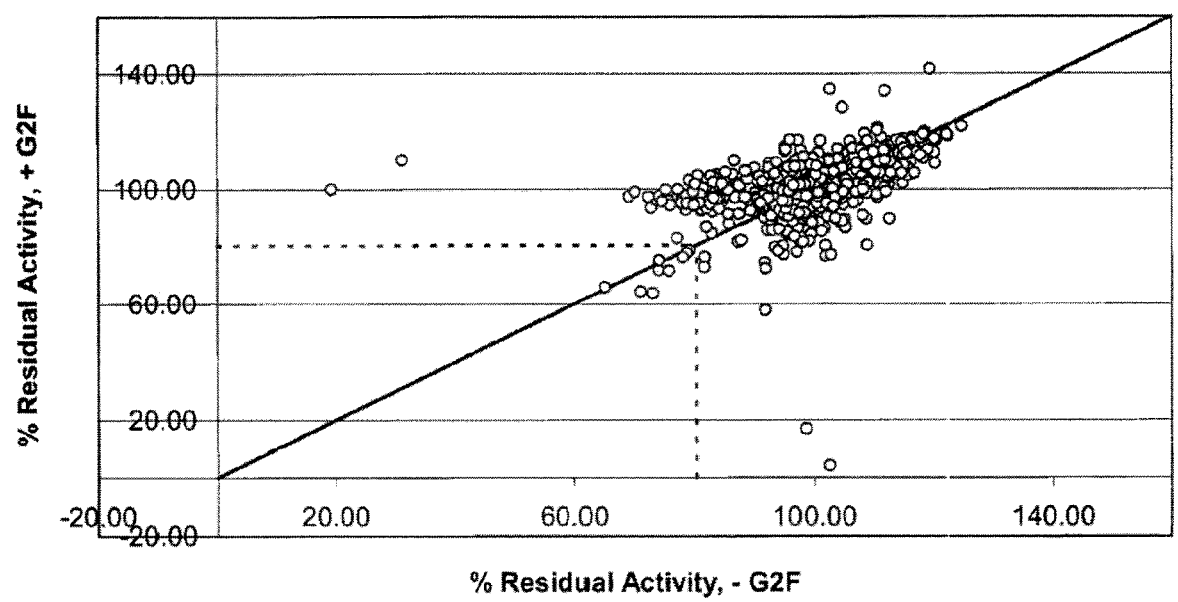
FIG. 1 shows screening data from a high throughput screen designed for the assessment of HPA inhibitors.

A high-throughput, plate-based assay based on the colorimetric α-amylase substrate, 2-chloro-4-nitrophenyl α-maltotrioside (CNP-G3), was used to screen for novel HPA inhibitors in natural product extracts. Samples were run in duplicate and results of the screen are shown as a standard two-dimensional plot (FIG. 1). Crude extracts that resulted in <80% residual activity at a concentration of 0.3 μg/60 μL, indicated by the dotted lines in the plot, were selected for further analysis. The material with the greatest inhibitory activity was the product of exhaustive methanolic extraction of the Caribbean Sea anemone, *Stichodactyla helianthus*. Activity-guided extraction and purification involving successive reverse phase and size exclusion chromatographies was performed to yield 2 mg of active material from a 154 g *S. helianthus* specimen. $^1H$ and $^{13}C$ NMR analysis indicated that the active component was proteinaceous in nature. De novo MS-MS and Edman sequencing yielded the following sequence bearing forty-four amino acids in total among them six cysteine residues: H$_2$N-ESGNSCYIYH-GVSGICKASCAEDEKAMAGMGVCEGHLCCYKTPW-COOH (SEQ ID NO: 1).

Mass spectrometric analysis before and after treatment with dithiothreitol and iodoacetamide indicated the presence of three disulfide bridges. The remaining material was used to study its inhibition of HPA. Through these preliminary tests, reversible competitive inhibition of HPA was observed and a low-nM $K_i$ was estimated. Once the original 2 mg of active material had been depleted, additional specimens of *S. helianthus* were processed in attempts to extract more peptide. Recovering more active material from these specimens was unsuccessful and no activity was detected in their extracts. It is unknown whether the production of helianthamide is regulated within the anemone in response to certain environmental/developmental stimuli, or if it is perhaps the product of an algae or microorganism associated with the original anemone sampled.

Example 2: Recombinant Expression of Helianthamide in *E. coli*

Recombinant expression was pursued in *Escherichia coli* through a barnase-based fusion system, in which Helianthamide was joined to an inactive form of the bacterial ribonuclease (bar'), through a TEV protease cleavage site. Barnase was selected for its lack of cysteines, a feature that has proven useful in the expression of small disulfide-rich peptides in the past (4, 17). Also, expression of barnase is directed through the secretory pathway, allowing to avoid the reducing conditions of the bacterial cytosol. An average yield of 15 mg/L of bar'-Helianthamide fusion could be achieved in BL21*(DE3) cells. A quick clean-up step was performed with nickel affinity chromatography before cleavage of the fusion. Release of Helianthamide from bar' could be achieved by incubation with TEV protease (100 units/mg fusion) at 30° C. for 24 hours. Treating the reaction mixture with 50% methanol provided a simple and effective means of separating Helianthamide from all other protein constituents, which precipitated out of solution upon exposure to the solvent. Simple methanolic extraction yielded Helianthamide of around go % purity. A final C-18 reverse phase column could be run to achieve complete purity.

The Helianthamide (hel) protein was characterised by circular dichroism spectroscopy (FIG. 2*b* and TABLE 3A) and the remaining material was used for preliminary inhibitory studies, in which reversible inhibition of HPA was observed with a low nanomolar inhibition constant (see FIG. 2A). In TABLE 3A, the secondary structural analysis of the CD spectra shown in FIG. 2B of the natural (extracted from *Stichodactyla helianthus*), synthetic and recombinant Helianthamide were compared. In general, the secondary structures of the three Helianthamides were quite similar, but both the synthetic and recombinant polypeptides had reduced alpha-helix formation as compared to the natural Helianthamide. Beta-sheet formation was consistent between all three polypeptides as was the number of turns estimated.

TABLE 3A

Secondary structural analysis of the CD spectra shown in FIG. 2B of the natural, synthetic and recombinant Helianthamide

| | Estimate of Proportion of each Secondary Structure | | | |
|---|---|---|---|---|
| | alpha-helix | beta-sheet | turns | other |
| Synthetic | 0.06 | 0.32 | 0.18 | 0.44 |
| Natural | 0.19 | 0.32 | 0.18 | 0.31 |
| Recombinant | 0.11 | 0.33 | 0.23 | 0.33 |

Example 3: Assessment of Free Thiols in Recombinant Helianthamide

A 5,5'-dithiobis-(2-nitrobenzoic acid) (DTNB) assay was conducted on the recombinant material to assess for the presence of free thiols as compared to bovine serum albumin (BSA) control, and consequently improper folding (18). The Helianthamide sample showed no increase in absorbance with increasing protein concentration, while the BSA positive control did and when the extinction coefficient of TNB2-(13 700 M−1 cm−1) is input into the Beer-Lambert equation, the corresponding concentration is equal to that of the BSA, indicating one free thiol.

Aliquots of Helianthamide of known concentration were incubated with DTNB, which reacts with free thiol groups to release 2-nitro-5-thiobenzoate. The liberation of 2-nitro-5-thiobenzoate can be monitored at λ=412 nm. The resulting data showed no significant release of 2-nitro-5-thiobenzoate with any concentration of Helianthamide, indicating the lack of free thiols. LC-MS/MS analysis was used to determine the connectivity of the disulfide bonds. Initially, proteolysis on the peptide should be controlled with the disulfides intact, before mass spectrometric analysis (19). Keeping all disulfides intact for MS analysis was sought after attempts at partial reduction and alkylation experiments led to evidence an all-or-nothing reduction of the disulfides (20). Unfortunately, with intact disulfides, the peptide was resistant to proteolysis by trypsin, chymotrypsin, proteinase K, and Lys-C under all conditions trialed. Random acid hydrolysis was then pursued (21). Intact peptide was incubated in 11M HCl at 37° C. for four days. These conditions led to partial digestion and after the four-day incubation a large proportion of intact peptide remained as observed by HPLC. The mixture of partially digested material was analyzed by LC-MS/MS (not shown). Some peaks of appropriate size were selected to determine the sequence and connectivity. From this data the connectivity of disulfides was confirmed to be a 1-5, 2-4, 3-6 pattern (TABLE 3B).

TABLE 3B

Select LC-MS/MS peaks and their corresponding sequences for disulfide assignment.

| M | Parent peak | Sequence | SEQ ID NO |
|---|---|---|---|
| 1198.42 | 600.21 (MH$^{2+}$) | IYHGVSGIC CE | 29 |
| 1279.58 | 640.79 (MH$^{2+}$) | HGVSGICKA MGVC | 26 27 |
| 1286.70 | 429.90 (MH$_{3+}$) | GICK KAMAGMGVC | 30 31 |
| 1311.70 | 656.85 (MH$^{2+}$) | CYIYHGV LCCC | 32 |

TABLE 3B-continued

Select LC-MS/MS peaks and their corresponding sequences for disulfide assignment.

| M | Parent peak | Sequence | SEQ ID NO |
|---|---|---|---|
| 1327.68 | 443.56 (MH$^{3+}$) | VCICKASCAECY | 33 |
| 1347.66 | 449.22 (MH$^{3+}$) | NSCYI | 34 |
| | | LCCYKC | 35 |
| 1416.68 | 709.34 (MH$^{2+}$) | GICEKAMAGMGVCE | 36 |
| 1439.60 | 480.88 (MH$^{3+}$) | SC | 37 |
| | | EGHLCCY | 38 |
| | | SCAE | |
| 1534.56 | 768.28 (MH$^{2+}$) | ESGNSC | 39 |
| | | GHLCC | 40 |
| | | SCAE | 38 |
| 1551.70 | 776.85 (MH$^{2+}$) | GNSC | 41 |
| | | GHLCCY | 42 |
| | | KASCA | 43 |
| 1606.82 | 804.41 (MH$^{2+}$) | CY | 44 |
| | | GVCEGHLC | 45 |
| | | SGICK | |
| 1631.78 | 816.89 (MH$^{2+}$) | SESGNSC | 46 |
| | | LCCYK | 35 |
| | | CAE | |
| 1698.81 | 566.27 (MH$^{3+}$) | SGNSC | 25 |
| | | LCC | 24 |
| | | CAEDEKAM | |
| 1760.80 | 881.40 (MH$^{2+}$) | GNSC | 41 |
| | | LCCYKT | 47 |
| | | SCAEDE | 48 |
| 1818.97 | 607.32 (MH$^{3+}$) | SESGNSCYIYHGCCSCA | 49 |

Example 4: Kinetic Analysis According to Morrison

Given the low-nM estimate of $K_i$ for the natural extract, kinetic analysis could not be pursued through standard Michaelis-Menten kinetics (22). In this study, inhibition constants below 50 nM were determined using the Morrison method: inhibition dose response curves at $[S]=K_M$ were constructed for varying enzyme concentrations (23, 24). The resulting data (FIG. 2A) was fit to the Morrison equation 1 to determine $K_{i,app}$, which could be converted to $K_i$ through equation 2, which is the relationship between these values for competitive inhibition.

$$v = v_0\left(1 - \frac{([E]_0 + [I] + K_{i-app}) - \sqrt{([E]_0 + [I] + K_{i-app})^2 - 4[E]_0[I]}}{2[E]_0}\right) \quad \text{Equation (1)}$$

$$K_{i-app} = K_i\left(1 + \frac{[S]}{K_M}\right) \quad \text{Equation (2)}$$

Through this method, helianthamide was determined to have a $K_i$ of 0.01 nM against HPA. Inhibition of nine other glycosidases was explored (TABLE 4). Of these nine, only porcine pancreatic α-amylase (PPA) was inhibited, with a $K_i$ of 0.1 nM. No inhibitory activity was observed, up to concentrations of 1 μM, against the other enzymes, which included three bacterial α-amylases. A $K_i$ of 0.01 nM makes helianthamide one of the most potent α-amylase inhibitors known to date. Previously, the *Streptomyces* peptide tendamistat had been the benchmark of potent α-amylase inhibitors (26-30). The $K_i$ of tendamistat has been estimated to be between 9×10$^{-12}$ and 2×10$^{-10}$ (31). Helianthamide has also displayed impressive structural stability. Its tolerance to organic solvents allowed for its original discovery in a screen designed for small molecules, and created the opportunity for a simple methanolic-based purification during its expression. Its stability to proteolytic degradation, low pH, and high temperatures also opens the possibility of oral administration in therapeutic usage.

TABLE 4

Inhibitory specificity of helianthamide.

| Enzyme | $K_i$ |
|---|---|
| Porcine pancreatic α-amylase | 0.1 nM |
| Human maltase-glucoamylase | N.I. |
| *Roseburia inulinivorans* α-amylase A | N.I. |
| *Butyrivibrio fibrisolvens* α-amylase B | N.I. |
| *Bacillus licheniformis* α-amylase | N.I. |
| Bovine liver β-galactosidase | N.I. |
| Green coffee bean α-galactosidase | N.I. |
| Jack bean α-mannosidase | N.I. |
| Brewer's yeast α-glucosidase | N.I. |
| Almond β-glucosidase | N.I. |

N.I. indicates no inhibition observed at a concentration of 1 μM.

Example 5: Solid State Structures of Helianthamide Co-Crystallized with PPA

Analysis of Helianthamide was continued through X-ray crystallography experiments. Helianthamide was co-crystallized with PPA. PPA has high sequence and structural homology to HPA, however the porcine enzyme has a more accessible active site than the human isozyme in the crystalline form, a feature that proved useful when co-crystallization of helianthamide and HPA was unsuccessful. Crystals of the helianthamide/PPA complex grew via the hanging drop method in approximately three weeks. The resulting X-ray diffraction data were processed into a structure of 2.6 Å resolution (TABLE 5A).

Helianthamide shares 13 hydrogen bonds with the enzyme (TABLE 5B), including interactions with key residues such as the catalytic nu-cleophile, D197, as well as D300 and H305. The loop from residues 306-3100 of PPA also form a hydrophobic patch that is matched by a corresponding one on Helianthamide, formed by residues Y7 and V32. Another area of hydrophobic interactions surrounds the side chain of V163 of PPA. Helianthamide surrounds this residue with the side chains of I8, V12, and Y40. L162 and L165 extend the size of this hydrophobic patch and form a β-turn that also packs against Y9, T42 and W44. The interactions with residues 162-165 help stabilize both ends of the loop that extends into the active site and interacts with the catalytic carboxylates. D197 shares 2 hydrogen bonds with the inhibitor, and D300 has one. Both hydrogen bond to H10 of Helianthamide, which is very likely protonated, creating a salt bridge that further stabilizes the loop.

One glycerol molecule is also found in the interface between Helianthamide and PPA. The glycerol forms four hydrogen bonds, three to the enzyme, and one to Helianthamide. Glycerol was added to the crystallization medium as a cryoprotectant after the crystals had formed, and thus likely displaces several ordered water molecules that would have helped stabilize inhibitor binding.

TABLE 5A

Summary of structure determination statistics.

| Data Collection Parameters | Helianthamide/PPA Inhibitor Complex |
|---|---|
| Space group | $P2_12_12_1$ |
| Unit cell dimensions (Å) | |
| a | 43.75 |
| b | 103.28 |
| c | 111.90 |
| Total no. reflections collected | 116266 (8116) |
| No. of unique reflections[a] | 16310 (1177) |
| Mean I/□I[a] | 17.3 (7.5) |
| Multiplicity[a] | 7.1 (6.8) |
| Merging R-factor (%)[a] | 10.4 (29.1) |
| Maximum resolution (Å) | 2.60 |
| Structure Refinement Values | |
| Number of reflections | 15472 |
| Resolution range (Å) | 49.19-2.6 |
| Completeness (%)[a] | 95.2 (94.7) |
| No. protein atoms | 3904 |
| No. inhibitor atoms | 322 |
| No. solvent atoms | 219 |
| Average thermal factors (Å$^2$) | |
| Protein atoms | 16.9 |
| Inhibitor atoms | 21.3 |
| Solvent atoms | 35.5 |
| Overall | 17.2 |
| Final R-free value (%)[b] | 22.6 |
| Final R-factor (%) | 18.1 |
| Structure Stereochemistry | r.m.s. deviations |
| bonds (Å) | 0.004 |
| angles (□) | 0.882 |

[a]Values in parentheses refer to the highest resolution shell: 2.73-2.6 Å.
[b]5% of the data was set aside to calculate R-free.

TABLE 5B

Hydrogen Bonds in the Helianthamide-PPA Interface

| Atoms | | |
|---|---|---|
| Helianthamide | PPA | Distance (Å) |
| S2/OG | G308/O | 3.85 |
| S5/OG | H305/O | 3.40 |
| Y9/OH | D197/OD2 | 2.38 |
| Y9/OH | Y62/O | 3.70 |
| H10/ND1 | D300/OD1 | 2.75*** |
| H10/NE2 | D197/OD1 | 2.83 |
| S13/OG | H305/O | 2.73 |
| A28/N | E149/O | 3.00 |
| W44/NE1 | V163/O | 2.93 |
| S2/O | S310/N | 3.17 |
| S5/OG | H305/ND1 | 3.24 |
| I8/O | Y151/OH | 3.78 |
| A28/O | Y151/N | 2.86 |

***indicates possible salt bridge

The resulting structure (FIG. 3) displays Helianthamide bound in a non-covalent complex with PPA. A third of Helianthamide's solvent accessible surface area is buried in contact with PPA, primarily occurring within and around the amylase active site. Helianthamide is composed of a four-stranded antiparallel β-sheet and three disulfide bonds in the same 1-5, 2-4, 3-6 disulfide topology that was determined in the LC-MS/MS analysis (FIGS. 6A & B). Within the amylase active site, three residues of Helianthamide, Y7, Y9, and H10, interact with PPA's catalytic residues. Y9 and H10 both hydrogen bond to the enzyme's nucleophilic residue, D197(2). Y9 also forms a hydrogen bond with H101, which borders the active site of the enzyme. H10 forms a second hydrogen bond to D300, a residue important for positioning water during catalysis. Sitting further back within the active site, Y7 also hydrogen bonds to D300.

Example 6: Mutants of Helianthamide

Y7A, Y9A, and H10A mutants of Helianthamide were expressed and tested as inhibitors against HPA in their bar'-Helianthamide fusion form. The bar'-Helianthamide fusion inhibited HPA with a $K_i$ of 0.9 nM, and this higher baseline was desirable to establish significant differences between the mutants. The results of this kinetic survey are summarized in TABLE 6. Mutating Y9 had the largest impact on inhibition, leading to a 50-fold decrease in potency. Outside the amylase active site, there were relatively few hydrogen bonds or ionic interactions between Helianthamide and PPA. Rather, there is a hydrophobic interface between the proteins near the amylase active site. Pancreatic α-amylase contains hydrophobic patches around the active site cleft which are used to stabilize the positioning of amylose substrate (25). Helianthamide is able to interact with these patches through its own hydrophobic residues, one of them being I8, which orients its side chain in the opposite direction from the adjacent residues, Y7 and Y9. I8, along with V12, contributes to the hydrophobic surface area, which appears to form a pocket around V163 of the enzyme. A T163R HPA mutant was expressed in order to disrupt this interface and was used to confirm the trends observed for the Helianthamide mutant kinetics. There was no change in $k_{cat}$ or $K_M$ for this HPA mutant with the CNPG3 substrate. The T163R mutation led to a 20-fold decrease in Helianthamide potency, a trend that remained when tested against the Y7A, Y9A, and H10A mutants (TABLE 6). It was reassuring to see the trend in mutants remain at higher $K_i$ values, which could be tested by the Michaelis-Menten model, as it helps to validate the previous method of $K_i$ determination for the nM and sub-nM values, as these can be notoriously difficult to determine with accuracy and precision.

TABLE 6

Results of kinetic survey of bar'-helianthamide fusion form mutants.

| Helianthamide Type | HPA $K_i$ (nM) | T163R HPA $K_i$ (nM) |
|---|---|---|
| Bar'-helianthamide | 0.9 | 20 |
| Bar'-Y7A | 5 | 107 |
| Bar'-Y9A | 47 | 960 |
| Bar'-H10A | 15 | 321 |

Example 7: Structural Comparison of Helianthamide with Montbretin A

The YIYH inhibitory motif of Helianthamide is unique in glycosidase inhibitors (30, 32). Aromatic residues tyrosine and histidine are solely responsible for binding within the active site. The orientation of the isoleucine allows for interaction with the surrounding hydrophobic area. The phenolic-rich inhibitory motif of Helianthamide mirrors another recently discovered HPA inhibitor (FIG. 4). Montbretin A (MbA), a complex flavonol derivative, was discovered in a parallel screen of biological extracts to that of Helianthamide (33). It has a $K_i$ of 8 nM against HPA. MbA's inhibitory activity was traced to the myricetin and caffeic acid moieties, which are linked by a disaccharide. An overlay of MbA (PDB: 4W93) with the inhibitory motif of Helianthamide reveals a strikingly similar orientation of the inhibitory moieties. Y9 of Helianthamide aligns with MbA's A-ring; their hydroxyl groups line up to interact with D197 of the enzyme. H10 is found nearby the caffeic ester moiety, though in a somewhat perpendicular orientation, with D300 orienting its side chain inwards to interact with the imidazole ring.

Example 8: Structural Comparison of Helianthamide with β-Defensins Peptides

Sequence and structural BLAST searches were conducted for Helianthamide. While there were no homologous sequences identified, Helianthamide was found to be structurally homologous to β-defensins (FIG. 5). The β-defensins are a family mammalian and avian antimicrobial peptides characterized by their cationic and amphipathic nature, 1-5, 2-4, 3-6 disulfide topology, and anti-parallel β-sheet core (34-36). While rare, structural homologues of the β-defensins have been uncovered in the past. All known homologues are potent toxins, which exert their effects on $N^+$ or $K^+$ channels (5). One in particular, ShI, was also isolated from *Stichodactyla helianthus*. This peptide is a neurotoxin and interacts with voltage-gated $Na^+$ channels through positively and negatively charged clusters on its surface (37). In the case of the β-defensins and the previously described structural relatives, charge distribution on the peptide surface is required for their fatal activities. Helianthamide does not emulate its cousins in this regard. Rather, it is Helianthamide's neutral residues that predominantly account for the activities described in this work.

Example 9: Expression of the Helianthamide in Yeast

The ppic9-SUMOhel plasmid was linearized with SacI, purified by BuOH precipitation, and transformed into electrocompetent GS115 *P. pastoris*. The transformed cells were plated onto MD (minimal dextrose) plates and incubated at 30 deg for two days. Thirty transformants were selected and screened on MM (minimal methanol), YPD, and MD plates. Colonies that grew well on all plates were selected for trial expressions. Twenty colonies were grown in 3 mL BMGY (buffered glycerol-complex medium) for two days at 30 degrees. The cells were washed and induced with 1 mL of BMMY (buffered methanol-complex medium) for four days, adding 0.5% methanol each day. Culture supernatants were collected at 2 and 4 days and 10 µL of each was run on an SDS-PAGE gel. Test expressions were carried out for four of these clones, of which two representatives of SUMO-helianthamide expression in 3 mL test expressions were tested in a sample gel, wherein samples from culture supernatant of two transformants. 500 mL of overnight cultures were induced with 100 mL of BMMY. The cultures were induced 2× with 0.5% MeOH each day. The cells were harvested after four days at 30 deg. The SUMO-helianthamide fusion could be purified from the culture supernatant (concentrated in an Amicon™ cell with to kDa filter) through nickel affinity chromatography. The resulting fusion could then be cleaved with ULP1 SUMO protease to release helianthamide which could be separated from the reaction mixture by treatment with MeOH and subsequently purified to homogeneity by RP-HPLC.

Example 10: Activity of Truncated Helianthamide Peptides and Fusion Peptides Numerous truncated peptides based around the N-terminal motif "YIYH" were also tested for mammalian alpha-amylase inhibitory activity as shown in TABLE 7, wherein Ac represents the acetyl functional group.

TABLE 7

Inhibitory Activity of truncated peptides

| Truncated Peptide (SEQ ID NO) | Inhibitory Activity |
|---|---|
| Ac-YIYH-$NH_2$ (SEQ ID NO: 6) | no inhibition detected |
| Ac-YIYHGVSGI-$NH_2$ (SEQ ID NO: 4) | 25 μM |
| Ac-CYIYHGVSGIC-$NH_2$ (SEQ ID NO: 8) | 30 μM |
| Ac-CYIYHGVSGIC-$NH_2$ (disulfide bridge) (SEQ ID NO: 8) | 12 μM |

The motif YIYH (SEQ ID NO: 28) alone did not have detectable mammalian alpha-amylase inhibitory activity, but slightly longer peptides did show reasonable inhibitory activity. Furthermore, the addition of a disulfide bridge improved the inhibitory activity.

Numerous fusion peptides prepared for recombinant expression of Helianthamide as described herein (SEQ ID NOs:16-17), having considerable amino acid sequences at the N-terminus of the peptide also showed mammalian alpha-amylase inhibitory activity before cleavage to release the Helianthamide polypeptide (data not shown).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

The reference to any prior art in this specification is not, and should not be taken as, an acknowledgement or any form of suggestion that that prior art forms part of the common general knowledge in Canada or any other country.

Patent Documents

L. Teik N G, C.-H. Sun, M.-N. Lai (Kang Jia Biotech Corp. Ltd, TW). Alpha-glucosidase inhibitor. US Patent Application 2013 0165679 A1; Mar. 21, 2012.

S. Withers, A. C. Tarling, R. Andersen, G. D. Brayer, K. Woods (The University of British Columbia, Calif.). Alpha-amylase inhibitors: the montbretins and uses thereof. U.S. Pat. No. 8,431,541 B2; Apr. 30, 2013.

M. A. Murray, J. B. Roufs, A. Roh-Schmidt (Access Business Group International LLC, US). Nutritional supplement containing alpha-glucosidase and alpha-amylase inhibitors. U.S. Pat. No. 7,354,606 B2; Apr. 8, 2008.

Other Publications

1. Brayer G D, Luo Y, & Withers S G (1995) The structure of human pancreatic alpha-amylase at 1.8 A resolution and comparisons with related enzymes. *Protein Sci* 4(9): 1730-1742.
2. Rydberg E H, et al. (2002) Mechanistic analyses of catalysis in human pancreatic alpha-amylase: detailed kinetic and structural studies of mutants of three conserved carboxylic acids. *Biochemistry* 41(13):4492-4502.
3. Numao S, et al. (2004) In situ extension as an approach for identifying novel alpha-amylase inhibitors. *J Biol Chem* 279(46):48282-48291.
4. Schmoldt H-U, Wentzel A, Becker S, & Kolmar H (2005) A fusion protein system for the recombinant production of short disulfide bond rich cystine knot peptides using barnase as a purification handle pp 82-89.
5. Torres A M & Kuchel P W (2004) The beta-defensin-fold family of polypeptides. *Toxicon* 44(6):581-588.
6. Adeghate E, Schattner P, & Dunn E (2006) An update on the etiology and epidemiology of diabetes mellitus. *Ann N Y Acad Sci* 1084:1-29.
7. Aye T & Levitsky L L (2003) Type 2 diabetes: an epidemic disease in childhood. *Curr Opin Pediatr* 15(4):411-415.
8. Smyth S & Heron A (20006) Diabetes and obesity: the twin epidemics. *Nat Med* 12(1):75-80.
9. Lee Y, et al. (2014) Hyperglycemia in rodent models of type 2 diabetes requires insulin-resistant alpha cells. *Proc Natl Acad Sci USA* 111(36):13217-13222.
10. Inzucchi S E, et al. (2015) Management of hyperglycaemia in type 2 diabetes, 2015: a patient-centred approach. Update to a position statement of the American Diabetes Association and the European Association for the Study of Diabetes. *Diabetologia* 58(3):429-442.
11. Beyuo T, et al. (2015) Metformin versus Insulin in the Management of Pre-Gestational Diabetes Mellitus in Pregnancy and Gestational Diabetes Mellitus at the Korle Bu Teaching Hospital: A Randomized Clinical Trial. *PLoS One* 10(5):e0125712.
12. Ramasubbu N, Paloth V, Luo Y, Brayer G D, & Levine M J (1996) Structure of human salivary alpha-amylase at 1.6 A resolution: implications for its role in the oral cavity. *Acta Crystallogr D Biol Crystallogr* 52(Pt 3):435-446.
13. Sels J P, Huijberts M S, & Wolffenbuttel B H (1999) Miglitol, a new alpha-glucosidase inhibitor. *Expert Opin Pharmacother* 1(1):149-156.
14. Li C, et al. (2005) Acarbose rearrangement mechanism implied by the kinetic and structural analysis of human pancreatic alpha-amylase in complex with analogues and their elongated counterparts. *Biochemistry* 44(9):3347-3357.
15. Hsiao S H, Liao L H, Cheng P N, & Wu T J (2006) Hepatotoxicity associated with acarbose therapy. *Ann Pharmacother* 40(1):151-154.
16. Vichayanrat A, Ploybutr S, Tunlakit M, & Watanakejorn P (2002) Efficacy and safety of voglibose in comparison with acarbose in type 2 diabetic patients. *Diabetes Res Clin Pract* 55(2):99-103.
17. Li Y (2011) Recombinant production of antimicrobial peptides in *Escherichia coli*: a review. *Protein Expr Purif* 80(2):260-267.
18. Riener C, Kada G, & Gruber H (2002) Quick measurement of protein sulfhydryls with Ellman's reagent and with 4,4'-dithiodipyridine. (Anal Bioanal Chem.), pp 266-276.
19. Tang Y Q & Selsted M E (1993) Characterization of the disulfide motif in BNBD-12, an antimicrobial beta-defensin peptide from bovine neutrophils. *J Biol Chem* 268(9):6649-6653.
20. Schroeder B O, et al. (2011) Reduction of disulphide bonds unmasks potent antimicrobial activity of human β-defensin 1. *Nature* 469(7330):419-423.
21. Bauer M, Sun Y, Degenhardt C, & Kozikowski B (1993) Assignment of all four disulfide bridges in echistatin. *J Protein Chem* 12(6):759-764.
22. Copeland R A (2002) *Enzymes: A Practical Introduction to Structure, Mechanism, and Data Analysis* 2nd Ed.
23. Morrison J F (1969) Kinetics of the reversible inhibition of enzyme-catalysed reactions by tight-binding inhibitors. *Biochim Biophys Acta* 185(2):269-286.
24. Murphy D J (2004) Determination of accurate KI values for tight-binding enzyme inhibitors: an in silico study of experimental error and assay design. (Analytical Biochemistry), pp 61-67.
25. Qian M, Spinelli S, Driguez H, & Payan F (1997) Structure of a pancreatic alpha-amylase bound to a substrate analogue at 2.03 A resolution. *Protein Sci* 6(11): 2285-2296.
26. Sokočvić A, Han S, & Engels J W (2011) Biophysical characterization of α-amylase inhibitor Parvulustat (Z-2685) and comparison with Tendamistat (HOE-467). *Biochim Biophys Acta* 1814(10):1383-1393.
27. König V, Vértesy L, & Schneider T R (2003) Structure of the alpha-amlase inhibitor tendamistat at 0.93 A. *Acta Crystallogr D Biol Crystallogr* 59(Pt 10):1737-1743.
28. Meyer B H, Miiller F O, Grigoleit H G, Esterhuysen A J, & Clur B K (1984) Effects of tendamistate on postprandial plasma glucose, free fatty acid and triglyceride levels. *S Afr Med J* 66(6):224-225.
29. Meyer B H, Müller F O, Kruger J B, Clur B K, & Grigoleit H G (1984) Effects of tendamistate (an alpha-amylase inactivator), guar and placebo on starch metabolism. *S Afr Med J* 66(6):222-223.
30. Svensson B, Fukuda K, Nielsen P K, & Bensager B C (2004) Proteinaceous alpha-amylase inhibitors. *Biochim Biophys Acta* 1696(2):145-156.
31. Vértesy L, Oeding V, Bender R, Zepf K, & Nesemann G (1984) Tendamistat (HOE 467), a tight-binding alpha-amylase inhibitor from *Streptomyces tendae* 4158. Isolation, biochemical properties. *Eur J Biochem* 141(3):505-512.
32. Franco O L, Rigden D J, Melo F R, & Grossi-De-Sá M F (2002) Plant alpha-amylase inhibitors and their interaction with insect alpha-amylases. *Eur J Biochem* 269(2): 397-412.
33. Tarling C A, et al. (2008) The search for novel human pancreatic alpha-amylase inhibitors: high-throughput screening of terrestrial and marine natural product extracts. *Chembiochem* 9(3):433-438.
34. White S H, Wimley W C, & Selsted M E (1995) Structure, function, and membrane integration of defensins. *Curr Opin Struct Biol* 5(4):521-527.
35. Ganz T (2003) Defensins: antimicrobial peptides of innate immunity. *Nat Rev Immunol* 3(9):710-720.

36. Ganz T (2004) Defensins: antimicrobial peptides of vertebrates. *C R Biol* 327(6):539-549.
37. Kem W R, Parten B, Pennington M W, Price D A, & Dunn B M (1989) Isolation, characterization, and amino acid sequence of a polypeptide neurotoxin occurring in the sea anemone *Stichodactyla helianthus*. *Biochemistry* 28(8):3483-3489.
38. Kaspar A A & Reichert J M (2013) Future directions for peptide therapeutics development. *Drug Discov Today* 18(17-18):807-817.
39. Rydberg E H, et al. (1999) Cloning, mutagenesis, and structural analysis of human pancreatic alpha-amylase expressed in *Pichia pastoris*. *Protein Sci* 8(3):635-643.
40. Whitehead W E (2001) Gastrointestinal motility disorder of the small intestine, large intestine, rectum, and pelvic floor. *International Foundation for Functional Gastointestinal Disorders*, Paper 162 (IFFGD Fact Sheet No. 162).
41. Tysoe C. et al. (2016) Potent human α-amylase inhibition by the ϕ-defensin-like protein helianthamide. *ACS Cent. Sci.* 2: 154-161.
42. Borges de Melo E, da Silveira Gomes A & Carvalho, I (2006) α- and β-glucosidase inhibitors: chemical structure and biological activity. Tetrahedron 62: 10277-10302.
43. Zung A & Zadik Z (2003) Acarbose treatment of infant dumping syndrome: extensive study of glucose dynamics and long-term follow-up. *J Pediatric Endocrinol & Metabolism* 16: 907-915.
44. Hasegawa T et al. (1998) Long-term effect of α-glucosidase inhibitor on late dumping syndrome. *J Gastroenterol Hepatol* 13: 1201-1206.
45. Ng D D et al. (2001) Acarbose treatment of postprandial hypoglycemia in children after Nissen fundoplication. *J Pediatr* 139: 877-879.
46. Playford R J, Pither C, Gao R & Middleton S J (2013) Use of alpha-glucosidase inhibitor acarbose in patients with 'Middleton syndrome': normal gastric anatomy but with accelerated gastric emptying causing postprandial reactive hypoglycemia and diarrhea. *Can J Gastroenterol* 27 (7): 403-404.
47. Palomba S, Falbo A, Zullo F & Orio F Jr. (2009) Evidence-based and potential benefits of metformin in the polycystic ovary syndrome: a comprehensive review. *Endocrine Rev* 30 (1): 1-50.
48. Inui Y et al. (1990): Inhibitory effect of a new α-glucosidase inhibitor on fatty liver in Zucker fatty rats. *J. Hepatol.* (10) 62-68.
49. Okada K et al. (2009): The α-glucosidase inhibitor acarbose prevents obesity and simple steatosis in sequestosome 1/A170/p62 deficient mice. *Hepatol. Res.* (39) 490-500.
50. Lefebvre P J & Scheen A J (1992) Management of non-insulin-dependent diabetes mellitus. *Drugs* 44 (Suppl. 3): 29-38.
51. Viollet B et al. (2012) Cellular and molecular mechanisms of metformin: an overview. *Clin. Sci.* (122) 253-270.
52. DeCensi A & Gennari A (2011) Insulin breast cancer connection: confirmatory data set the stage for better care. *J. Clin. Oncol.* (1) 7-10
53. Lazar C et al. (2007) Treatment of hepatitis B virus-infected cells with α-glucosidase inhibitors results in production of virions with altered molecular composition and infectivity. *Antiviral Res* 76: 30-37.
54. Mehta A et al. (1998) α-Glucosidase inhibitors as potential broad based antiviral agents. *FEBS Lett* 430: 17-22.
56. Ratner L, vander Heyden N & Dedera D (1991) Inhibition of HIV and SIV infectivity by blockade of α-glucosidase activity. *Virology* 181: 180-192.

```
INFORMAL SEQUENCE LISTING
                                                          SEQ ID NO: 1
ESGNSCYIYHGVSGICKASCAEDEKAMAGMGVCEGHLCCYKTPW

SEQ ID NO: 2
SESGNSCYIYHGVSGICKASCAEDEKAMAGMGVCEGHLCCYKTPW

SEQ ID NO: 3
Xaa.1a-Xaa.1b-Xaa.2-Xaa.3-Xaa.4-Xaa.5-C-Y-I-Y-H-

Xaa.6-Xaa.7-Xaa.8-Xaa.9-Xaa.10a-Xaa.10b-Xaa.11-Xaa.12-Xaa.13a-

Xaa.13b-Xaa.14-Xaa.15-Xaa.16-Xaa.17-Xaa.18-Xaa.19-Xaa.20-Xaa.21-

Xaa.22-Xaa.23-Xaa.24-Xaa.25a-Xaa.25b-Xaa.26-Xaa.27-Xaa.28-Xaa.29a-

Xaa.29b-Xaa.29c-Xaa.30-Xaa.31-Xaa.32a-Xaa.32b-Xaa.33 wherein Xaa.1a is Ser (S) or Thr (T) or absent, Xaa.1b is Asp(D) or

Glu (E) or absent, Xaa.2 is Ser (S) or Thr
(T) or absent, Xaa.3 is Gly (G) or Ala (A) or absent, Xaa.4 is Asn (N) or Gln
(Q) or absent, Xaa.5 is Ser (S) or Thr (T) or absent, Xaa.6 is Gly (G) or Ala (A) or absent, Xaa.7 is Val (V), Ala (A), Ile (I) or Leu
(L) or absent, Xaa.8 is Ser (S) or Thr (T) or absent, Xaa.9 is Gly (G) or Ala (A) or absent, Xaa.10a is Val (V), Ala (A), Ile (I) or Leu (L) or absent, Xaa.10b is Cys (C) or absent, Xaa.11 is Lys (K), Arg (R) or His
(H) or
```

-continued absent, Xaa.12 is Val (V), Ala (A), Ile (I) or Leu (L) or absent, Xaa.13a is Ser (S) or Thr (T) or absent, Xaa.13b is Cys (C) or absent, Xaa.14 is Val (V), Ala (A), Ile (I) or Leu (L) or absent, Xaa.15 is Asp(D) or Glu (E) or absent, Xaa.16 is Asp(D) or Glu (E) or absent, Xaa.17 is Asp(D) or Glu (E) or absent, Xaa.18 is Lys (K), Arg (R) or His (H) or absent, Xaa.19 is Val (V), Ala (A), Ile (I) or Leu (L) or absent, Xaa.20 is Met (M) or Leu (L) or absent, Xaa.21 is Val (V), Ala (A), Ile (I) or Leu (L) or absent, Xaa.22 is Gly (G) or Ala (A) or absent, Xaa.23 is Met (M) or Leu (L) or absent, Xaa.24 is Gly (G) or Ala (A) or absent, Xaa.25a is Val (V), Ala (A), Ile (I) or Leu (L) or absent, Xaa.25b is Cys (C) or absent, Xaa.26 is Asp(D) or Glu (E) or absent, Xaa.27 is Gly (G) or Ala (A) or absent, Xaa.28 is Lys (K), Arg (R) or His (H) or absent, Xaa.29a is Val (V), Ala (A), Ile (I) or Leu (L) or absent, Xaa.29b is Cys (C) or absent, Xaa.29c is Cys (C) or absent, Xaa.30 is Tyr (Y) or Phe (F) or absent, Xaa.31 is Lys (K), Arg (R) or His (H) or absent, Xaa.32a is Ser (S) or Thr (T) or absent, Xaa.32b is Pro (P) or absent, and Xaa.33 is Trp (W) or Tyr (Y) or absent.

SEQ ID NO: 4
YIYHGVSGI

SEQ ID NO: 5
YIYHGV

SEQ ID NO: 6
YIYH

SEQ ID NO: 7
CYIYH-Xaa.6-Xaa.7-Xaa.8-Xaa.9-Xaa.10 wherein Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A) and Xaa.10 is Val (V), Ala (A), Ile (I) or Leu (L).

SEQ ID NO: 8
CYIYHGVSGIC

SEQ ID NO: 9
Xaa.1a-Xaa.1b-Xaa.2-Xaa.3-Xaa.4-Xaa.5-C-Y-I-Y-H-Xaa.6-Xaa.7-Xaa.8-Xaa.9-Xaa.10 wherein Xaa.1a is Ser (S) or Thr (T) or absent, Xaa.1b is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S) or Thr (T), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A) and Xaa.10 is Val (V), Ala (A), Ile (I) or Leu (L).

-continued

SEQ ID NO: 10
Xaa.1-Xaa.2-Xaa.3-Xaa.4-Xaa.5-C-Y-I-Y-H-Xaa.6-

Xaa.7-Xaa.8-Xaa.9-Xaa.10-C-Xaa.11-Xaa.12-Xaa.13-C-Xaa.14-Xaa.15-

Xaa.16-Xaa.17-Xaa.18-Xaa.19-Xaa.20-Xaa.21-Xaa.22-Xaa.23-Xaa.24-Xaa.25-

C-Xaa.26-Xaa.27-Xaa.28-Xaa.29-C-C-Xaa.30-Xaa.31-Xaa.32-P-Xaa.33 wherein Xaa.1 is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S)

or Thr (T), Xaa.6 is Gly (G) or Ala (A), Xaa.7 is Val (V), Ala (A),

Ile (I) or Leu (L), Xaa.8 is Ser (S) or Thr (T), Xaa.9 is Gly (G) or

Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.13 is Ser (S) or Thr (T), Xaa.14 is Val (V), Ala (A), Ile (I)

or Leu (L), Xaa.15 is Asp(D) or Glu (E), Xaa.16 is Asp(D) or Glu (E),

Xaa.17 is Asp(D) or Glu (E), Xaa.18 is Lys (K), Arg (R) or His (H),

Xaa.19 is Val (V), Ala (A), Ile (I) or Leu (L), Xaa.20 is Met (M) or

Leu (L), Xaa.21 is Val (V), Ala (A), Ile (I) or Leu (L), Xaa.22 is Gly (G) or Ala (A), Xaa.23 is Met (M) or Leu (L), Xaa.24 is Gly (G) or Ala (A), Xaa.25 is Val (V), Ala (A), Ile (I) or Leu (L), Xaa.26 is Asp (D)

or Glu (E), Xaa.27 is Gly (G) or Ala (A), Xaa.28 is Lys (K), Arg (R)

or His (H), Xaa.29 is Val (V), Ala (A), Ile (I) or Leu (L), Xaa.30 is

Tyr (Y) or Phe (F), Xaa.31 is Lys (K), Arg (R) or His (H), Xaa.32 is

Ser (S) or Thr (T) and Xaa.33 is Trp (W) or Tyr (Y).

SEQ ID NO: 11
Xaa.1-Xaa.2-Xaa.3-Xaa.4-Xaa.5-C-Y-I-Y-H-Xaa.6-

Xaa.7-Xaa.8-Xaa.9-Xaa.10-C-Xaa.11-Xaa.12-Xaa.13-C-Xaa.14-Xaa.15-

Xaa.16-Xaa.17-Xaa.18-Xaa.19-Xaa.20-Xaa.21-Xaa.22-Xaa.23-Xaa.24-Xaa.25-

C-Xaa.26-Xaa.27-Xaa.28-Xaa.29-C-C-Xaa.30-Xaa.31-Xaa.32-P-Xaa.33 (SEQ

ID NO: 11)

wherein Xaa.1 is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S)

or Thr (T), Xaa.6 is Gly (G) or Ala (A), Xaa.7 is Val (V), Ala (A),

Ile (I) or Leu (L), Xaa.8 is Ser (S) or Thr (T), Xaa.9 is Gly (G) or

Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.13 is Ser (S) or Thr (T), Xaa.14 is Val (V), Ala (A), Ile (I)

or Leu (L), Xaa.15 is Asp(D) or Glu (E), Xaa.16 is Asp(D) or Glu (E),

Xaa.17 is Asp(D) or Glu (E), Xaa.18 is Lys (K), Arg (R) or His (H), Xaa.19 is Val (V), Ala (A), Ile (I) or Leu (L), Xaa.20 is Met (M) or Leu (L), Xaa.21 is Val (V), Ala (A), Ile (I) or Leu (L), Xaa.22 is Gly (G) or Ala (A), Xaa.23 is Met (M) or Leu (L), Xaa.24 is Gly (G) or Ala (A), Xaa.25 is Val (V), Ala (A), Ile (I) or Leu (L), Xaa.26 is Asp (D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), Xaa.32 is Ser (S) or Thr (T) and Xaa.33 is Trp (W) or Tyr (Y).

SEQ ID NO: 12

Xaa.1-S-Xaa.3-Xaa.4-S-C-Y-I-Y-H-Xaa.6-Xaa.7-Xaa.8-Xaa.9-Xaa.10-C-Xaa.11-Xaa.12-S-C-Xaa.14-Xaa.15-Xaa.16-Xaa.17-Xaa.18-Xaa.19-M-Xaa.21-Xaa.22-M-Xaa.24-Xaa.25-C-Xaa.26-Xaa.27-Xaa.28-Xaa.29-C-C-Xaa.30-Xaa.31-Xaa.32-P-W wherein Xaa.1 is Asp(D) or Glu (E), Xaa.3 is Gly (G) or Ala (A), Xaa.4 is Asn (N) or Gln (Q), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.21 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), and Xaa.32 is Ser (S) or Thr (T).

SEQ ID NO: 13

Xaa.1-S-Xaa.3-Xaa.4-S-C-Y-I-Y-H-Xaa.6-V-S-Xaa.9-Xaa.10-C-Xaa.11-Xaa.12-S-C-Xaa.14-Xaa.15-Xaa.16-Xaa.17-Xaa.18-Xaa.19-M-A-Xaa.22-M-Xaa.24-Xaa.25-C-Xaa.26-Xaa.27-Xaa.28-Xaa.29-C-C-Xaa.30-Xaa.31-Xaa.32-P-W wherein Xaa.1 is Asp(D) or Glu (E), Xaa.3 is Gly (G) or Ala (A), Xaa.4 is Asn (N) or Gln (Q), Xaa.6 is Gly (G) or Ala (A), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), and Xaa.32 is Ser (S) or Thr (T).

SEQ ID NO: 14
E-S-Xaa.3-Xaa.4-S-C-Y-I-Y-H-Xaa.6-V-S-Xaa.9-Xaa.10-C-K-Xaa.12-S-C-Xaa.14-E-D-E-K-Xaa.19-M-A-Xaa.22-M-Xaa.24-Xaa.25-C-E-Xaa.27-H-Xaa.29-C-C-Xaa.30-K-Xaa.32-P-W wherein Xaa.3 is Gly (G) or Ala (A), Xaa.4 is Asn (N) or Gln (Q), Xaa.6 is Gly (G) or Ala (A), Xaa.9 is Gly (G) or Ala (A), Xaa.10 is Val (V), Ala (A), Ile (I) or Leu (L), Xaa.12 is Val (V), Ala (A), Ile (I) or Leu (L), Xaa.14 is Val (V), Ala (A), Ile (I) or Leu (L), Xaa.19 is Val (V), Ala (A), Ile (I) or Leu (L), Xaa.21 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.27 is Gly (G) or Ala (A), Xaa.29 is Val (V), Ala (A), Ile (I) or Leu (L), Xaa.30 is Tyr (Y) or Phe (F), and Xaa.32 is Ser (S) or Thr (T).

SEQ ID NO: 15
E-S-Xaa.3-Xaa.4-S-C-Y-I-Y-H-Xaa.6-V-S-Xaa.9-Xaa.10-C-K-Xaa.12-S-C-Xaa.14-E-D-E-K-Xaa.19-M-A-Xaa.22-M-Xaa.24-Xaa.25-C-E-Xaa.27-H-Xaa.29-C-C-Y-K-Xaa.32-P-W (SEQ ID NO: 15)

wherein Xaa.3 is Gly (G) or Ala (A), Xaa.4 is Asn (N) or Gln (Q), Xaa.6 is Gly (G) or Ala (A), Xaa.9 is Gly (G) or Ala (A), Xaa.10 is Ile (I) or Leu (L), Xaa.12 is Ile (I) or Leu (L), Xaa.14 is Ile (I) or Leu (L), Xaa.19 is Ile (I) or Leu (L), Xaa.21 is Ile (I) or Leu (L), Xaa.22 is Gly (G) or Ala (A), Xaa.24 is Gly (G) or Ala (A), Xaa.25 is Ile (I) or Leu (L), Xaa.27 is Gly (G) or Ala (A), Xaa.29 is Ile (I) or Leu (L), and Xaa.32 is Ser (S) or Thr (T).

-continued

Sequence of the barnase'-helianthamide gene optimized for expression in *E. coli*.

SEQ ID NO: 16

MRFPSIFTAVLFAASSALAAPVNTTTEDETAQIPAEAVIGYSDLEGDFDVAVLPFSNSTNNGLLF

INTTIASIAAKEEGVSLEKREAEAYVEF*DYKDDDDK*G

HHHHHHGGSDSEVNQEAKPEVKPEVKPETHINL

KVSDGSSEIFFKIKKTTPLRRLMEAFAKRQGKEMDSLTFLYDGIEIQADQTPEDLDMEDN-
DIIEAHREQI

GGESGNSCYIYHGVSGICKASCAEDEKAMAGMGVCEGHLCCYKTPW

SEQ ID NO: 17

EAEAYVEF*DYKDDDDK*GHHHHHHGGSDSEVNQEAKPEVKPEVKPETHINLKVSDGSSEIFFKIKK

TTPLRRLMEAFAKRQGKEMDSLTFLYDGIEIQADQTPEDLDMEDNDIIEAHREQIGG
ESGNSCYIYHGVS

GICKASCAEDEKAMAGMGVCEGHLCCYKTPW

AMF SIGNAL; HELIANTHAMIDE; HIS-TAG HHHHHHHH; *FLAG TAG*; SUMO

SEQ ID NO: 18

ATG AAA CAA TCC ACC ATC GCA CTG GCC CTG CTG CCG CTG CTG

TTC ACG CCG GTT ACA AAG CCG CTG GTG CAT CAT CAT CAT CAT

CAC TCG AGT GGC GCA CAG GTT ATT AAC ACC TTT GAT GGT GTT

GCT GAC TAT CTG CAA ACG TAC CAT AAA CTG CCG GAT AAT TAT

ATC ACC AAA TCA GAA GCA CAG GCC CTG GGT TGG GTC GCA TCG

AAA GGT AAC CTG GCA GAT GTG GCT CCG GGC AAA AGT ATT GGC

GGT GAC ATC TTC TCC AAT CGT GAA GGT AAA CTG CCG GGC AAA

TCT GGT CGT ACC TGG CGC GAA GCG GAT ATT AAC TAT ACG TCA

GGC TTT CGT AAT TCG GAT CGC ATT CTG TAC AGC TCT GAC TGG

CTG ATC TAT AAA ACC ACG GAC GCC TAC CAA ACC TTC ACG AAA

ATT CGT ATC GAA GGC CGC GAA AGT GGT AAC TCC TGC TAT ATT

TAC CAC GGC GTT AGC GGT ATC TGC AAA GCG TCT TGT GCC GAA

GAT GAA AAA GCA ATG GCA GGC ATG GGC GTG TGT GAA GGT CAT

CTG TGT TGT TAC AAA ACC CCG TGG TGA TAG

---

What is claimed is:

1. A composition comprising: (a) a peptide consisting of a contiguous stretch of amino acids having the consensus amino acid sequence (SEQ ID NO: 3)
Xaa.1a-Xaa.1b-Xaa.2-Xaa.3-Xaa.4-Xaa.5-C-Y-I-Y-H-

Xaa.6-Xaa.7-Xaa.8-Xaa.9-Xaa.10a-Xaa.10b-Xaa.11-

Xaa.12-Xaa.13a-Xaa.13b-Xaa.14-Xaa.15-Xaa.16-

Xaa.17-Xaa.18-Xaa.19-Xaa.20-Xaa.21-Xaa.22-Xaa.23-

Xaa.24-Xaa.25a-Xaa.25b-Xaa.26-Xaa.27-Xaa.28-

Xaa.29a-Xaa.29b-Xaa.29c-Xaa.30-Xaa.31-Xaa.32a-

Xaa.32b-Xaa.33 wherein the peptide is up to 45 amino acids in length, and wherein Xaa.1a is Ser (S) or Thr (T) or absent, Xaa.1b is Asp(D) or Glu (E) or absent, Xaa.2 is Ser (S) or Thr (T) or absent, Xaa.3 is Gly (G) or Ala (A) or absent, Xaa.4 is Asn (N) or Gln (Q) or absent, Xaa.5 is Ser (S) or Thr (T) or absent, Xaa.6 is Gly (G) or Ala (A) or absent, Xaa.7 is Val (V), Ala (A), Ile (I) or Leu (L) or absent, Xaa.8 is Ser (S) or Thr (T) or absent, Xaa.9 is Gly (G) or Ala (A) or absent, Xaa.10a is Val (V), Ala (A), Ile (I) or Leu (L) or absent, Xaa.10b is Cys (C) or absent, Xaa.11 is Lys (K), Arg (R) or His (H) or absent, Xaa.12 is Val (V), Ala (A), Ile (I) or Leu (L) or absent, Xaa.13a is Ser (S) or Thr (T) or absent, Xaa.13b is Cys (C) or absent, Xaa.14 is Val (V), Ala (A), Ile (I) or Leu (L) or absent, Xaa.15 is Asp(D) or Glu (E) or absent, Xaa.16 is Asp(D) or Glu (E) or absent, Xaa.17 is Asp(D) or Glu (E) or absent, Xaa.18 is Lys (K), Arg (R) or His (H) or absent, Xaa.19 is Val (V), Ala (A), Ile (I) or Leu (L) or absent, Xaa.20 is Met (M) or Leu (L) or absent, Xaa.21 is Val (V), Ala (A), Ile (I) or Leu (L) or absent, Xaa.22 is Gly (G) or Ala (A) or absent, Xaa.23 is Met (M) or Leu (L) or absent, Xaa.24 is Gly (G) or Ala (A) or absent, Xaa.25a is Val (V), Ala (A), Ile (I) or Leu (L) or absent, Xaa.25b is Cys (C) or absent, Xaa.26 is Asp(D) or Glu (E) or absent, Xaa.27 is Gly (G) or Ala (A) or absent, Xaa.28 is Lys (K), Arg (R) or His (H) or absent, Xaa.29a is Val (V), Ala (A), Ile (I) or Leu (L) or absent, Xaa.29b is Cys (C) or absent, Xaa.29c is Cys (C) or absent, Xaa.30 is Tyr (Y) or Phe (F) or absent, Xaa.31 is Lys (K), Arg (R) or His (H) or absent, Xaa.32a is Ser (S) or Thr (T) or absent, Xaa.32b is Pro (P) or absent, and Xaa.33 is Trp (W) or Tyr (Y) or absent;

and (b) a pharmaceutically acceptable excipient;

wherein the peptide has one or more modified amino acids and wherein the peptide has alpha-amylase inhibitory activity.

2. The composition of claim 1, wherein the peptide consists of the amino acid sequence:

(SEQ ID NO: 7)
C-Y-I-Y-H-Xaa.6-Xaa.7-Xaa.8-Xaa.9-Xaa.10 wherein the peptide is up to 10 amino acids in length, and wherein Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A) and Xaa.10 is Val (V), Ala (A), Ile (I) or Leu (L) wherein the peptide has one or more modified amino acids and wherein the peptide has alpha-amylase inhibitory activity.

3. The composition of claim 1, wherein the peptide consists of the amino acid sequence:

(SEQ ID NO: 9)
Xaa.1a-Xaa.1b-Xaa.2-Xaa.3-Xaa.4-Xaa.5-C-Y-I-

Y-H-Xaa.6-Xaa.7-Xaa.8-Xaa.9-Xaa.10 wherein the peptide is up to 16 amino acids in length, and wherein Xaa.1a is Ser (S) or Thr (T) or absent, Xaa.1b is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S) or Thr (T), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A) and Xaa.10 is Val (V), Ala (A), Ile (I) or Leu (L) wherein the peptide has one or more modified amino acids and wherein the peptide has alpha-amylase inhibitory activity.

4. The composition of claim 1, wherein the peptide consists of the amino acid sequence:

(SEQ ID NO: 10)
Xaa.1-Xaa.2-Xaa.3-Xaa.4-Xaa.5-C-Y-I-Y-H-Xaa.6-

Xaa.7-Xaa.8-Xaa.9-Xaa.10-C-Xaa.11-Xaa.12-Xaa.13-

C-Xaa.14-Xaa.15-Xaa.16-Xaa.17-Xaa.18-Xaa.19-

Xaa.20-Xaa.21-Xaa.22-Xaa.23-Xaa.24-Xaa.25-C-

Xaa.26-Xaa.27-Xaa.28-Xaa.29-C-C-Xaa.30-Xaa.31-

Xaa.32-P-Xaa.33 wherein the peptide is up to 44 amino acids in length, and wherein Xaa.1 is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S) or Thr (T), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.13 is Ser (S) or Thr (T), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.20 is Met (M) or Leu (L), Xaa.21 is Val (V), Ala (A), Ile (I) or Leu (L), Xaa.22 is Gly (G) or Ala (A), Xaa.23 is Met (M) or Leu (L), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), Xaa.32 is Ser (S) or Thr (T) and Xaa.33 is Trp (W) or Tyr (Y) wherein the peptide has one or more modified amino acids and wherein the peptide has alpha-amylase inhibitory activity.

5. The composition of claim 1, wherein the peptide consists of the amino acid sequence:

(SEQ ID NO: 11)
Xaa.1-Xaa.2-Xaa.3-Xaa.4-Xaa.5-C-Y-I-Y-H-Xaa.6-

Xaa.7-Xaa.8-Xaa.9-Xaa.10-C-Xaa.11-Xaa.12-Xaa.13-C-

-continued

```
Xaa.14-Xaa.15-Xaa.16-Xaa.17-Xaa.18-Xaa.19-X2a.20-

Xaa.21-Xaa.22-Xaa.23-Xaa.24-Xaa.25-C-Xaa.26-

Xaa.27-Xaa.28-Xaa.29-C-C-Xaa.30-Xaa.31-Xaa.32-

P-Xaa.33
``` wherein the peptide is up to 44 amino acids in length, and wherein Xaa.1 is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S) or Thr (T), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.13 is Ser (S) or Thr (T), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.20 is Met (M) or Leu (L), Xaa.21 is Val (V), Ala (A), Ile (I) or Leu (L), Xaa.22 is Gly (G) or Ala (A), Xaa.23 is Met (M) or Leu (L), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), Xaa.32 is Ser (S) or Thr (T) and Xaa.33 is Trp (W) or Tyr (Y) wherein the peptide has one or more modified amino acids and wherein the peptide has alpha-amylase inhibitory activity.

6. The composition of claim 1, wherein the peptide consists of the amino acid sequence:

```
                                          (SEQ ID NO: 12)
Xaa.1-S-Xaa.3-Xaa.4-S-C-Y-I-Y-H-Xaa.6-Xaa.7-Xaa.8-

Xaa.9-Xaa.10-C-Xaa.11-Xaa.12-S-C-Xaa.14-Xaa.15-

Xaa.16-Xaa.17-Xaa.18-Xaa.19-M-Xaa.21-Xaa.22-M-

Xaa.24-Xaa.25-C-Xaa.26-Xaa.27-Xaa.28-Xaa.29-C-C-

Xaa.30-Xaa.31-Xaa.32-P-W
``` wherein the peptide is up to 44 amino acids in length, and wherein Xaa.1 is Asp(D) or Glu (E), Xaa.3 is Gly (G) or Ala (A), Xaa.4 is Asn (N) or Gln (Q), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.21 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), and Xaa.32 is Ser (S) or Thr (T) wherein the peptide has one or more modified amino acids and wherein the peptide has alpha-amylase inhibitory activity.

7. The composition of claim 1, wherein the peptide consists of the amino acid sequence:

```
                                          (SEQ ID NO: 13)
Xaa.1-S-Xaa.3-Xaa.4-S-C-Y-I-Y-H-Xaa.6-V-S-Xaa.9-

Xaa.10-C-Xaa.11-Xaa.12-S-C-Xaa.14-Xaa.15-Xaa.16-

Xaa.17-Xaa.18-Xaa.19-M-A-Xaa.22-M-Xaa.24-Xaa.25-

C-Xaa.26-Xaa.27-Xaa.28-Xaa.29-C-C-Xaa.30-Xaa.31-

Xaa.32-P-W
``` wherein the peptide is up to 44 amino acids in length, and wherein Xaa.1 is Asp(D) or Glu (E), Xaa.3 is Gly (G) or Ala (A), Xaa.4 is Asn (N) or Gln (Q), Xaa.6 is Gly (G) or Ala (A), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), and Xaa.32 is Ser (S) ox Thr (T) wherein the peptide has one or more modified amino acids and wherein the peptide has alpha-amylase inhibitory activity.

8. The composition of claim 1, wherein the peptide consists of the amino acid sequence:

```
                                          (SEQ ID NO: 14)
E-S-Xaa.3-Xaa.4-S-C-Y-I-Y-H-Xaa.6-V-S-Xaa.9-

Xaa.10-C-K-Xaa.12-S-C-Xaa.14-E-D-E-K-Xaa.19-M-A-

Xaa.22-M-Xaa.24-Xaa.25-C-E-Xaa.27-H-Xaa.29-C-C-

Xaa.30-K-Xaa.32-P-W
``` wherein the peptide is up to 44 amino acids in length, and wherein Xaa.3 is Gly (G) or Ala (A), Xaa.4 is Asn (N) or Gln (Q), Xaa.6 is Gly (G) or Ala (A), Xaa.9 is Gly (G) or Ala (A), Xaa.10 is Val (V), Ala (A), Ile (I) or Leu (L), Xaa.12 is Val (V), Ala (A), Ile (I) or Leu (L), Xaa.14 is Val (V), Ala (A), Ile (I) or Leu (L), Xaa.19 is Val (V), Ala (A), Ile (I) or Leu (L), Xaa.21 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.27 is Gly (G) or Ala (A), Xaa.29 is Val (V), Ala (A), Ile (I) or Leu (L), Xaa.30 is Tyr (Y) or Phe (F), and Xaa.32 is Ser (S) or Thr (T) wherein the peptide has one or more modified amino acids and wherein the peptide has alpha-amylase inhibitory activity.

9. The composition of claim 1, wherein the peptide consists of the amino acid sequence:

```
                                                    (SEQ ID NO: 15)
E-S-Xaa.3-Xaa.4-S-C-Y-I-Y-H-Xaa.6-V-S-Xaa.9-

Xaa.10-C-K-Xaa.12-S-C-Xaa.14-E-D-E-K-Xaa.19-M-A-

Xaa.22-M-Xaa.24-Xaa.25-C-E-Xaa.27-H-Xaa.29-C-C-Y-

K-Xaa.32-P-W
``` wherein the peptide is up to 44 amino acids in length, and wherein Xaa.3 is Gly (G) or Ala (A), Xaa.4 is Asn (N) or Gln (Q), Xaa.6 is Gly (G) or Ala (A), Xaa.9 is Gly (G) or Ala (A), Xaa.10 is Ile (I) or Leu (L), Xaa.12 is Ile (I) or Leu (L), Xaa.14 is Ile (I) or Leu (L), Xaa.19 is Ile (I) or Leu (L), Xaa.21 is Ile (I) or Leu (L), Xaa.22 is Gly (G) or Ala (A), Xaa.24 is Gly (G) or Ala (A), Xaa.25 is Ile (I) or Leu (L), Xaa.27 is Gly (G) or Ala (A), Xaa.29 is Ile (I) or Leu (L), and Xaa.32 is Ser (S) or Thr (T) wherein the peptide has one or more modified amino acids and wherein the peptide has alpha-amylase inhibitory activity.

10. The composition of claim 1, wherein the peptide comprises a contiguous stretch of amino acids consisting of the amino acid sequence:

```
                                                    (SEQ ID NO: 2)
SESGNSCYIYHGVSGICKASCAEDEKAMAGMGVCEGHLCCYKTPW
``` wherein the peptide has one or more modified amino acids and wherein the peptide has alpha-amylase inhibitory activity.

11. The composition of claim 1, wherein Cys (C) form a disulfide bridge.

12. The composition of claim 1, wherein C6 and C38 form a disulfide bridge, C16 and C33 form a disulfide bridge and C20 and C39 form a disulfide bridge.

13. A peptide comprising a contiguous stretch of amino acids consisting of the consensus amino acid sequence
Xaa.1a-Xaa.1b-Xaa.2-Xaa.3-Xaa.4-Xaa.5-C-Y-I-Y-H-Xaa.6-Xaa.7-Xaa.8-Xaa.9- Xaa.10a-Xaa.10b-Xaa.11-Xaa.12-Xaa.13a-Xaa.13b-Xaa.14-Xaa.15-Xaa.16-Xaa.17-Xaa.18- Xaa.19-Xaa.20-Xaa.21-Xaa.22-Xaa.23.Xaa-24-Xaa.25a.Xaa.25b-Xaa.26-Xaa.27-Xaa.28- Xaa.29a-Xaa.29b-Xaa.29c-Xaa.30-Xaa.31-Xaa.32a-Xaa.32b-Xaa.33 (SEQ ID NO: 3) wherein the peptide is up to 45 amino acids in length, and wherein Xaa.1a is Ser (S) or Thr (T) or absent, Xaa.1b is Asp(D) or Glu (E) or absent, Xaa.2 is Ser (S) or Thr (T) or absent, Xaa.3 is Gly (G) or Ala (A) or absent, Xaa.4 is Asn (N) or Gln (Q) or absent, Xaa.5 is Ser (S) or Thr (T) or absent, Xaa.6 is Gly (G) or Ala (A) or absent, Xaa.7 is Val (V), Ala (A), Ile (I) or Leu (L) or absent, Xaa.8 is Ser (S) or Thr (T) or absent, Xaa.9 is Gly (G) or Ala (A) or absent, Xaa.10a is Val (V), Ala (A), Ile (I) or Leu (L) or absent, Xaa.10b is Cys (C) or absent, Xaa.11 is Lys (K), Arg (R) or His (H) or absent, Xaa.12 is Val (V), ala (A), Ile (I) or Leu (L) or absent, Xaa.13a is Ser (S) or Thr (T) or absent, Xaa.13b is Cys (C) or absent, Xaa.14 is Val (V), Ala (A), Ile (I) or Leu (L) or absent, Xaa.15 is Asp(D) or Glu (E) or absent, Xaa.16 is Asp(D) or Glu (E) or absent, Xaa.17 is Asp(D) or Glu (E) or absent, Xaa.18 is Lys (K), Arg (R) or His (H) or absent, Xaa.19 is Val (V), Ala (A), Ile (I) or Leu (L) or absent, Xaa.20 is Met (M) or Leu (L) or absent, Xaa.21 is Val (V), Ala (A), Ile (I) or Leu (L) or absent, Xaa.22 is Gly (G) or Ala (A) or absent, Xaa.23 is Met (M) or Leu (L) or absent, Xaa.24 is Gly (G) or Ala (A) or absent, Xaa.25a is Val (V), Ala (A), Ile (I) or Leu (L) or absent, Xaa.25b is Cys (C) or absent, Xaa.26 is Asp(D) or Glu (E) or absent, Xaa.27 is Gly (G) or Ala (A) or absent, Xaa.28 is Lys (K), Arg (R) or His (H) or absent, Xaa.29a is Val (V), Ala (A), Ile (I) or Leu (L) or absent, Xaa.29b is Cys (C) or absent, Xaa.29c is Cys (C) or absent, Xaa.30 is Tyr (Y) or Phe (F) or absent, Xaa.31 is Lys (K), Arg (R) or His (H) or absent, Xaa.32a is Ser (S) or Thr (T) or absent, Xaa.32b is Pro (P) or absent, and Xaa.33 is Trp (W) or Tyr (Y) or absent;
wherein the peptide has mammalian alpha-amylase inhibitory activity; and wherein the peptide has one or more modified amino acids.

14. The peptide of claim 13, wherein the peptide consists of the amino acid sequence:

```
                                                    (SEQ ID NO: 7)
C-Y-I-Y-H-Xaa.6-Xaa.7-Xaa.8-Xaa.9-Xaa.10
``` wherein the peptide is up to 10 amino acids in length, and wherein Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A) and Xaa.10 is Val (V), Ala (A), Ile (I) or Leu (L) wherein the peptide has mammalian alpha-amylase inhibitory activity; and wherein the peptide has one or more modified amino acids.

15. The peptide of claim 13, wherein the peptide consists of the amino acid sequence:

```
                                                    (SEQ ID NO: 9)
Xaa.1a-Xaa.1b-Xaa.2-Xaa.3-Xaa.4-Xaa.5-C-Y-I-Y-

H-Xaa.6-Xaa.7-Xaa.8-Xaa.9-Xaa.10
``` wherein the peptide is up to 16 amino acids in length, and wherein Xaa.1a is Ser (S) or Thr (T) or absent, Xaa.1b is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S) or, Thr (T), Xaa.6 is Gly (G) or Ala (A), Xaa.7 is Val (V), Ala (A), Ile (I) or Leu (L), Xaa.5 is Ser (S) or Thr (T), Xaa.9 is Gly (G) or Ala (A) and Xaa.10 is Val (V), Ala (A), Ile (I) or Leu (L) wherein the peptide has mammalian alpha-amylase inhibitory activity; and wherein the peptide has one or more modified amino acids.

16. The peptide of claim 13, wherein the peptide consists of the amino acid sequence:

```
                                                    (SEQ ID NO: 10)
Xaa.1-Xaa.2-Xaa.3-Xaa.4-Xaa.5-C-Y-I-Y-H-Xaa.6-

Xaa.7-Xaa.8-Xaa.9-Xaa.10-C-Xaa.11-Xaa.12-Xaa.13-

C-Xaa.14-Xaa.15-Xaa.16-Xaa.17-Xaa.18-Xaa.19-

Xaa.20-Xaa.21-Xaa.22-Xaa.23-Xaa.24-Xaa.25-C-

Xaa.26-Xaa.27-Xaa.28-Xaa.29-C-C-Xaa.30-Xaa.31-

Xaa.32-P-Xaa.33
``` wherein the peptide is up to 44 amino acids in length, and wherein Xaa.1 is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S) or Thr (T), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.13 is Ser (S) or Thr (T), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.20 is Met (M) or Leu (L), Xaa.21 is Val (V), Ala (A), Ile (I) or Leu (L), Xaa.22 is Gly (G) or Ala (A), Xaa.23 is Met (M) or Leu (L), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), Xaa.32 is Ser (S) or Thr (T) and Xaa.33 is Trp (W) or Tyr (Y) wherein the peptide has mammalian alpha-amylase inhibitory activity; and wherein the peptide has one or more modified amino acids.

17. The peptide of claim 13, wherein the peptide consists of the amino acid sequence:

```
                                           (SEQ ID NO: 11)
Xaa.1-Xaa.2-Xaa.3-Xaa.4-Xaa.5-C-Y-I-Y-H-Xaa.6-

Xaa.7-Xaa.8-Xaa.9-Xaa.10-C-Xaa.11-Xaa.12-Xaa.13-

C-Xaa.14-Xaa.15-Xaa.16-Xaa.17-Xaa.18-Xaa.19-

Xaa.20-Xaa.21-Xaa.22-Xaa.23-Xaa.24-Xaa.25-C-

Xaa.26-Xaa.27-Xaa.28-Xaa.29-C-C-Xaa.30-Xaa.31-

Xaa.32-P-Xaa.33
``` wherein the peptide is up to 44 amino acids in length, and wherein Xaa.1 is Asp(D) or Glu (E), Xaa.2 is Ser (S) or Thr (T), Xaa.3 is Gly (G) or Ala (A), Xaa.4 is Asn (N) or Gln (Q), Xaa.5 is Ser (S) or Thr (T), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.13 is Ser (S) or Thr (T), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.20 is Met (M) or Leu (L), Xaa.21 is Val (V), Ala (A), Ile (I) or Leu (L), Xaa.22 is Gly (G) or Ala (A), Xaa.23 is Met (M) or Leu (L), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), Xaa.32 is Ser (S) or Thr (T) and Xaa.33 is Trp (W) or Tyr (Y) wherein the peptide has mammalian alpha-amylase inhibitory activity; and wherein the peptide has one or more modified amino acids.

18. The peptide of claim 13, wherein the peptide consists of the amino acid sequence:
Xaa.1-S-Xaa.3-Xaa.4-S-C-Y-I-Y-H-Xaa.6-Xaa.7-Xaa.8-Xaa.9-Xaa.10-C-Xaa.11-Xaa.12-S-C-Xaa.14-Xaa.15-Xaa.16-Xaa.17-Xaa.18-Xaa.19-M-Xaa.21-Xaa.22-M-Xaa.24-Xaa.25-C-Xaa.26-Xaa.27-Xaa.28-Xaa.29-C-C-Xaa.30-Xaa.31-Xaa.32-P-W (SEQ ID NO: 12) wherein the peptide is up to 44 amino acids in length, and wherein Xaa.1 is Asp(D) or Glu (E), Xaa.3 is Gly (G) or Ala (A), Xaa.4 is Asn (N) or Gln (Q), Xaa.6 is Gly (G) or Ala (A), Xaa.7 is Val (V), Ala (A), Ile (I) or Leu (L), Xaa.8 is Ser (S) or Thr (T), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.21 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), and Xaa.32 is Ser (S) or Thr (T) wherein the peptide has mammalian alpha-amylase inhibitory activity; and wherein the peptide has one or more modified amino acids.

19. The peptide of claim 13, wherein the peptide consists of the amino acid sequence:

```
                                           (SEQ ID NO: 13)
Xaa.1-S-Xaa.3-Xaa.4-S-C-Y-I-Y-H-Xaa.6-V-S-Xaa.9-

Xaa.10-C-Xaa.11-Xaa.12-S-C-Xaa.14-Xaa.15-Xaa.16-

Xaa.17-Xaa.18-Xaa.19-M-A-Xaa.22-M-Xaa.24-Xaa.25-

C-Xaa.26-Xaa.27-Xaa.28-Xaa.29-C-C-Xaa.30-Xaa.31-

Xaa.32-P-W
``` wherein the peptide is up to 44 amino acids in length, and wherein Xaa.1 is Asp(D) or Glu (E), Xaa.3 is Gly (G) or Ala (A), Xaa.4 is Asn (N) or Gln (Q), Xaa.6 is Gly (G) or Ala (A), Xaa.9 is Gly (G) or Ala (A), Xaa.10 is Val (V), Ala (A), Ile (I) or Leu (L), Xaa.11 is Lys (K), Arg (R) or His (H), Xaa.12 is Val (V), Ala (A), Ile (I) or Leu (L), Xaa.14 is Val (V), Ala (A), Ile (I) or Leu (L), Xaa.15 is Asp(D) or Glu (E), Xaa.16 is Asp(D) or Glu (E), Xaa.17 is Asp(D) or Glu (E), Xaa.18 is Lys (K), Arg (R) or His (H), Xaa.19 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.26 is Asp(D) or Glu (E), Xaa.27 is Gly (G) or Ala (A), Xaa.28 is Lys (K), Arg (R) or His (H), Xaa.29 is Val (V), Ala (A), Ile (I) or Leu (L), Xaa.30 is Tyr (Y) or Phe (F), Xaa.31 is Lys (K), Arg (R) or His (H), and Xaa.32 is Ser (S) or Thr (T) wherein the peptide has mammalian alpha-amylase inhibitory activity; and wherein the peptide has one or more modified amino acids.

20. The peptide of claim 13, wherein the peptide consists of the amino acid sequence:

```
                                           (SEQ ID NO: 14)
E-S-Xaa.3-Xaa.4-S-C-Y-I-Y-H-Xaa.6-V-S-Xaa.9-

Xaa.10-C-K-Xaa.12-S-C-Xaa.14-E-D-E-K-Xaa.19-M-A-

Xaa.22-M-Xaa.24-Xaa.25-C-E-Xaa.27-H-Xaa.29-C-C-

Xaa.30-K-Xaa.32-P-W
``` wherein the peptide is up to 44 amino acids in length, and wherein Xaa.3 is Gly (G) or Ala (A), Xaa.4 is Asn (N)

or Gln (Q), Xaa.6 is Gly (G) or Ala (A), Xaa.9 is Gly (G) or Ala (A), Xaa.10 is Val (V), Ala (A), Ile (I) or Leu (L), Xaa.12 is Val (V), Ala (A), Ile (I) or Leu (L), Xaa.14 is Val (V), Ala (A), Ile (I) or Leu (L), Xaa.19 is Val (V), Ala (A), Ile (I) or Leu (L), Xaa.21 is Val (V), Ala (A), Ile (I) or Leu (L), Xaa.22 is Gly (G) or Ala (A), Xaa.24 is Gly (G) or Ala (A), Xaa.25 is Val (V), Ala (A), Ile (I) or Leu (L), Xaa.27 is Gly (G) or Ala (A), Xaa.29 is Val (V), Ala (A), Ile (I) or Leu (L), Xaa.30 is Tyr (Y) or Phe (F), and Xaa.32 is Ser (S) or Thr (T) wherein the peptide has mammalian alpha-amylase inhibitory activity; and wherein the peptide has one or more modified amino acids.

21. The peptide of claim 13, wherein the peptide consists of the amino acid sequence:

(SEQ ID NO: 15)
E-S-Xaa.3-Xaa.4-S-C-Y-I-Y-H-Xaa.6-V-S-Xaa.9-

Xaa.10-C-K-Xaa.12-S-C-Xaa.14-E-D-E-K-Xaa.19-M-A-

Xaa.22-M-Xaa.24-Xaa.25-C-E-Xaa.27-H-Xaa.29-C-C-Y-

K-Xaa.32-P-W wherein the peptide is up to 44 amino acids in length, and wherein Xaa.3 is Gly (G) or Ala (A), Xaa.4 is Asn (N) or Gln (Q), Xaa.6 is Gly (G) or Ala (A), Xaa.9 is Gly (G) or Ala (A), Xaa.10 is Ile (I) or Leu (L), Xaa.12 is Ile (I) or Leu (L), Xaa.14 is Ile (I) or Leu (L), Xaa.19 is Ile (I) or Leu (L), Xaa.21 is Ile (I) or Leu (L), Xaa.22 is Gly (G) or Ala (A), Xaa.24 is Gly (G) or Ala (A), Xaa.25 is Ile (I) or Leu (L), Xaa.27 is Gly (G) or Ala (A), Xaa.29 is Ile (I) or Leu (L), and Xaa.32 is Ser (S) or Thr (T) wherein the peptide has mammalian alpha-amylase inhibitory activity; and wherein the peptide has one or more modified amino acids.

22. The peptide of claim 13, wherein the peptide comprises a contiguous stretch of amino acids consisting of the amino acid sequence:

(SEQ ID NO: 2)
SESGNSCYIYHGVSGICKASCAEDEKAMAGMGVCEGHLCCYKTPW wherein the peptide has mammalian alpha-amylase inhibitory activity; and wherein the peptide has one or more modified amino acids.

23. The peptide of claim 13, wherein Cys (C) form a disulfide bridge.

24. The peptide of claim 13, wherein C6 and C38 form a disulfide bridge, C16 and C33 form a disulfide bridge and C20 and C39 form a disulfide bridge.

25. A method of inhibiting mammalian alpha-amylase activity, the method comprising: administering a peptide of claim 13 to a subject, wherein the subject is in need of alpha-amylase inhibition.

26. The method of claim 25, wherein the subject in need of alpha-amylase inhibition, has or is at risk of developing one or more of the following: Middleton syndrome; a motility disorder of the gastrointestinal tract; postprandial reactive hypoglycemia; postprandial syndrome; irritable bowel syndrome; diabetes mellitus type 1; diabetes mellitus type 2; pre-diabetes; obesity; dumping syndrome; infant dumping syndrome; polycystic ovary syndrome; steatohepatitis; and viral infection.

27. The method of claim 26, wherein the motility disorder is gastroesophageal reflux disease or gastroparesis.

28. The method of claim 26, wherein the viral infection is HIV infection or hepatitis B infection.

29. The method of claim 26, wherein the steatohepatitis is non-alcoholic fatty liver disease.

30. The method of claim 25, wherein the subject in need of alpha-amylase inhibition has had a gastric bypass or a gastrectomy.

31. The composition of claim 1, wherein the peptide consists essentially of the amino acid sequence:

(SEQ ID NO: 8)
C-Y-I-Y-H-G-V-S-G-I-C, wherein one or more of the amino acids of SEQ ID NO: 8 has been modified, and wherein the peptide has alpha-amylase inhibitory activity.

32. The composition of claim 1, wherein the peptide comprises a contiguous stretch of amino acids consisting essentially of the amino acid sequence:

(SEQ ID NO: 1)
ESGNSCYIYHGVSGICKASCAEDEKAMAGMGVCEGHLCCYKTPW, wherein one or more of the amino acids of SEQ ID NO: 1 has been modified, and wherein the peptide has alpha-amylase inhibitory activity.

33. The peptide of claim 13, wherein the peptide consists essentially of the amino acid sequence:

(SEQ ID NO: 8)
C-Y-I-Y-H-G-V-S-G-I-C, wherein one or more of the amino acids of SEQ ID NO: 8 has been modified, and wherein the peptide has alpha-amylase inhibitory activity.

34. The peptide of claim 13, wherein the peptide comprises a contiguous stretch of amino acids consisting essentially of the amino acid sequence:

(SEQ ID NO: 1)
ESGNSCYIYHGVSGICKASCAEDEKAMAGMGVCEGHLCCYKTPW, wherein one or more of the amino acids of SEQ ID NO: 1 has been modified, and wherein the peptide has alpha-amylase inhibitory activity.

35. The peptide of claim 13, wherein the peptide is a substantially purified peptide, and wherein the peptide comprises a contiguous stretch of amino acids consisting essentially of the amino acid sequence:

(SEQ ID NO: 1)
ESGNSCYIYHGVSGICKASCAEDEKAMAGMGVCEGHLCCYKTPW, wherein one or more of the amino acids of SEQ ID NO: 1 has been modified, and wherein the peptide has alpha-amylase inhibitory activity.

* * * * *

UNITED STATES PATENT AND TRADEMARK OFFICE
CERTIFICATE OF CORRECTION

PATENT NO. : 10,583,167 B2  
APPLICATION NO. : 15/740494  
DATED : March 10, 2020  
INVENTOR(S) : Stephen G. Withers et al.

Page 1 of 2

It is certified that error appears in the above-identified patent and that said Letters Patent is hereby corrected as shown below:

In the Specification

Column 3:
Line 33, "500 amino acids" should read --50 amino acids--.

Column 4:
Line 17, "Xaa.29-C-C-Xaa.3-" should read --Xaa.29-C-C-Xaa.30- --.
Line 18, "(SEQ ID NO: to)" should read --(SEQ ID NO: 10)--.
Line 21, "may be Asn (N) or Gin (Q)," should read --may be Asn (N) or Gln (Q),--.
Line 26, "Xaa.1 may be Lys (K)," should read --Xaa.11 may be Lys (K),--.
Line 36, "Ala (A), lie (I)" should read --Ala (A), Ile (I)--.

Column 5:
Line 22, "Asn (N) or Gin (Q)," should read --Asn (N) or Gln (Q),--.
Line 51, "Asn (N) or Gin (Q)," should read --Asn (N) or Gln (Q),--.

Column 6:
Line 10, "Asn (N) or Gin (Q)," should read --Asn (N) or Gln (Q),--.
Line 26, "K-Xaa2-S-C-Xaa.4-E" should read --K-Xaa.12-S-C-Xaa.14-E--.
Line 31, "(N) or Gin (Q)," should read --(N) or Gln (Q),--.
Line 64, "Asn (N) or Gin (Q) or absent," should read --Asn (N) or Gln (Q) or absent,--.

Column 7:
Line 52, "Asn (N) or Gin (Q)," should read --Asn (N) or Gln (Q),--.
Line 67, "Asn (N) or Gin (Q)," should read --Asn (N) or Gln (Q),--.

Column 8:
Line 4, "Xaa.1 may be Lys (K)," should read --Xaa.11 may be Lys (K),--.
Line 35, "Xaa.1 may be Lys (K)," should read --Xaa.11 may be Lys (K),--.

Signed and Sealed this  
Second Day of March, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,583,167 B2

Line 57, "Xaa.30-Xaa.32-P" should read --Xaa.30-Xaa.31-Xaa.32-P--.
Line 64, "Xaa.1 may be Lys (K)," should read --Xaa.11 may be Lys (K),--.

Column 9:
Line 44, "Asn (N) or Gin (Q)," should read --Asn (N) or Gln (Q),--.

Column 11:
Line 45, "two 1-defensins," should read --two β-defensins,--.

Column 26:
Line 59, "resulted in <80% residual" should read --resulted in ≤80% residual--.